(12) United States Patent
Dohale et al.

(10) Patent No.: US 11,214,823 B2
(45) Date of Patent: Jan. 4, 2022

(54) SAMPLE-TO-ANSWER SYSTEM FOR MICROORGANISM DETECTION FEATURING TARGET ENRICHMENT, AMPLIFICATION AND DETECTION

(71) Applicant: Canon U.S.A., Inc., Melville, NY (US)

(72) Inventors: Abhijit Dohale, Silver Spring, MD (US); Arvind Virmani, Germantown, MD (US); Brian Scrivens, Clarksburg, MD (US); Christopher Sneeder, Huntington Beach, CA (US); Denis Alias, Gainesville, VA (US); George Maltezos, Merrick, NY (US); Hanyoup Kim, Rockville, MD (US); Harini Shandilya, Bethesda, MD (US); Hongye Liang, Clarksville, MD (US); Jason Zsak, Silver Spring, MD (US); Johnathan Stuart Coursey, Rockville, MD (US); Kenton C. Hasson, Germantown, MD (US); Melissa Gosse, Jackson, NJ (US); Shulin Zeng, Silver Spring, MD (US); Yasuyuki Numajiri, Rockville, MD (US); Makoto Ogusu, Yorktown, VA (US); Yoichi Murakami, Newport News, VA (US); Kunihiro Sakai, Tokyo (JP)

(73) Assignee: Canon U.S.A., Inc., Melville, NY (US)

( * ) Notice: Subject to any disclaimer, the term of this patent is extended or adjusted under 35 U.S.C. 154(b) by 22 days.

(21) Appl. No.: 15/389,372

(22) Filed: Dec. 22, 2016

(65) Prior Publication Data

US 2017/0327867 A1    Nov. 16, 2017

Related U.S. Application Data

(60) Provisional application No. 62/270,987, filed on Dec. 22, 2015, provisional application No. 62/270,990, filed on Dec. 22, 2015, provisional application No. 62/271,001, filed on Dec. 22, 2015, provisional application No. 62/270,999, filed on Dec. 22, 2015, provisional application No. 62/270,997, filed on Dec. 22, 2015, provisional application No. 62/270,994, filed on Dec. 22, 2015, provisional application No. 62/270,992, filed on Dec. 22, 2015.

(51) Int. Cl.
*C12P 19/34*     (2006.01)
*C12Q 1/6806*    (2018.01)
*B01L 7/00*      (2006.01)
*B01L 3/00*      (2006.01)
*C12Q 1/686*     (2018.01)
*G01N 1/40*      (2006.01)

(52) U.S. Cl.
CPC ............ *C12Q 1/6806* (2013.01); *B01L 3/502* (2013.01); *B01L 3/508* (2013.01); *B01L 3/5021* (2013.01); *B01L 3/502715* (2013.01); *B01L 7/52* (2013.01); *C12Q 1/686* (2013.01); *B01L 2200/0605* (2013.01); *B01L 2200/0684* (2013.01); *B01L 2200/16* (2013.01); *B01L 2300/042* (2013.01); *B01L 2300/0654* (2013.01); *B01L 2300/0681* (2013.01); *B01L 2300/087* (2013.01); *B01L 2300/0896* (2013.01); *B01L 2300/123* (2013.01); *B01L 2300/168* (2013.01); *B01L 2300/1827* (2013.01); *B01L 2400/0478* (2013.01); *B01L 2400/0487* (2013.01); *B01L 2400/0605* (2013.01); *B01L 2400/0683* (2013.01); *B01L 2400/0688* (2013.01); *G01N 1/40* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 6,887,693 B2 | 5/2005 | McMillan et al. | |
| 7,086,666 B2 | 8/2006 | Richardson | |
| 7,629,124 B2 | 12/2009 | Hasson et al. | |
| 8,058,054 B2 | 11/2011 | Owen et al. | |
| 8,303,151 B2 | 11/2012 | Pance et al. | |
| 8,481,887 B2 | 7/2013 | Alpay et al. | |
| 8,962,252 B2 | 2/2015 | Liang et al. | |
| 9,278,321 B2 | 3/2016 | Dale et al. | |
| 2002/0010323 A1 | 1/2002 | Mitchell et al. | |
| 2002/0175079 A1* | 11/2002 | Christel | B01F 5/0403 204/601 |
| 2005/0013732 A1* | 1/2005 | Battrell | C12Q 1/686 436/17 |
| 2005/0191619 A1 | 9/2005 | Davis et al. | |
| 2007/0113880 A1 | 5/2007 | Atwood et al. | |
| 2008/0003593 A1 | 1/2008 | Hasson et al. | |
| 2010/0285490 A1 | 11/2010 | Dees et al. | |
| 2010/0291666 A1 | 11/2010 | Collier et al. | |
| 2011/0048547 A1 | 3/2011 | Hasson et al. | |

(Continued)

FOREIGN PATENT DOCUMENTS

| | | |
|---|---|---|
| GB | 2516666 A | 2/2015 |
| WO | 2011/002749 A1 | 1/2011 |
| WO | 2015/149569 A1 | 10/2015 |

OTHER PUBLICATIONS

Christopher Douglas Henry, "Nucleate Pool Boiling Characteristics From a Horizontal Microheater Array," Univ. of Maryland Dissertation, 331 pages (2005).

*Primary Examiner* — Kenneth R Horlick
(74) *Attorney, Agent, or Firm* — Rothwell, Figg, Ernst & Manbeck, P.C.

(57) ABSTRACT

The present invention relates to sample-to-answer systems, devices, cartridges, and method of using the same for detecting the presence of microorganisms in a sample, such as bacteria.

45 Claims, 85 Drawing Sheets

(56) References Cited

U.S. PATENT DOCUMENTS

| | | | |
|---|---|---|---|
| 2011/0312758 A1* | 12/2011 | Azimi | B01L 3/5027 |
| | | | 506/39 |
| 2012/0295269 A1* | 11/2012 | Pourahmadi | B01D 15/00 |
| | | | 435/6.12 |
| 2013/0217022 A1 | 8/2013 | Cao et al. | |
| 2014/0093867 A1 | 4/2014 | Burke et al. | |
| 2015/0212095 A1 | 7/2015 | Fu et al. | |

* cited by examiner

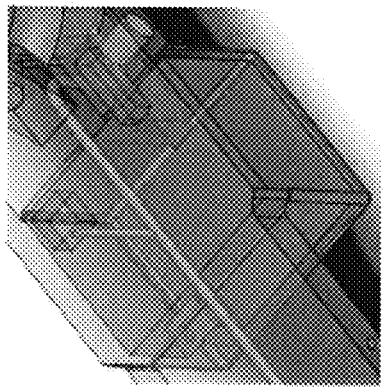
FIG. 14B
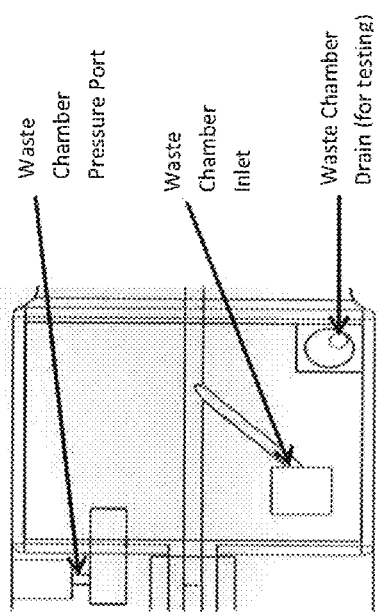
FIG. 14A
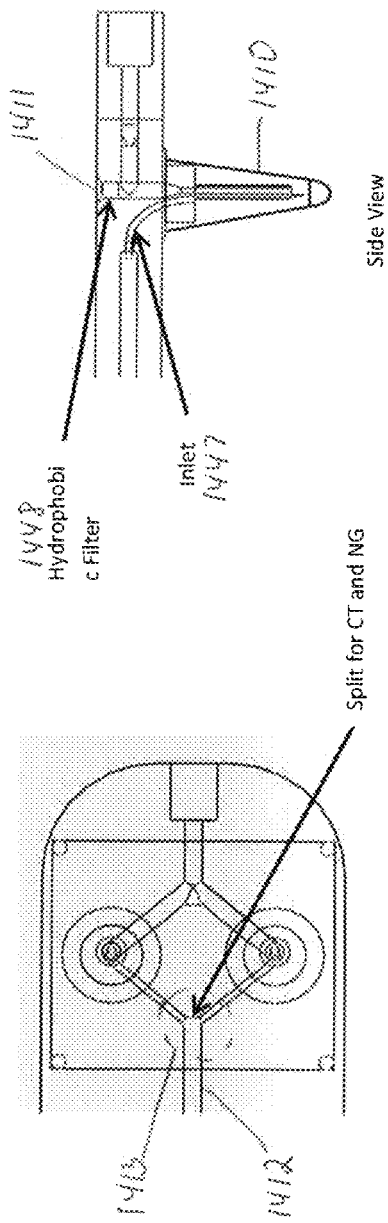
FIG. 14D
FIG. 14C

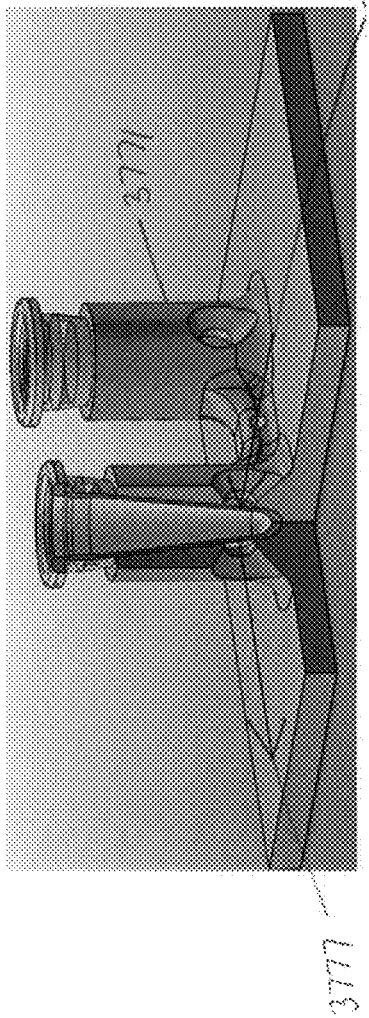
FIG. 37A
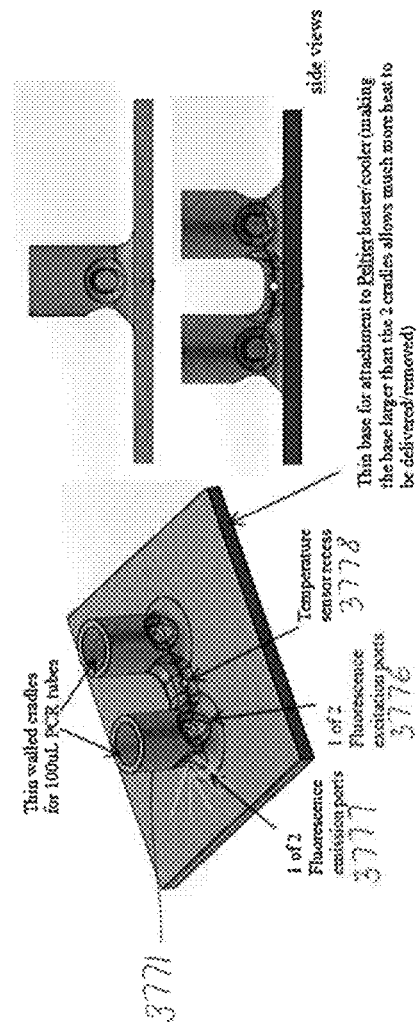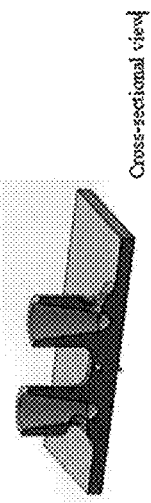
FIG. 37B

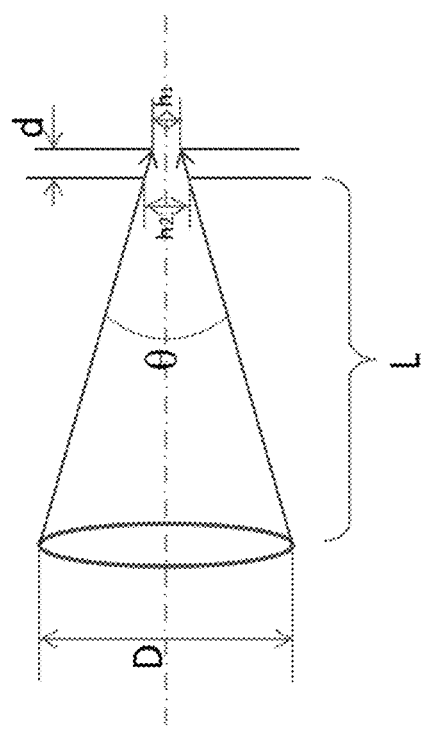
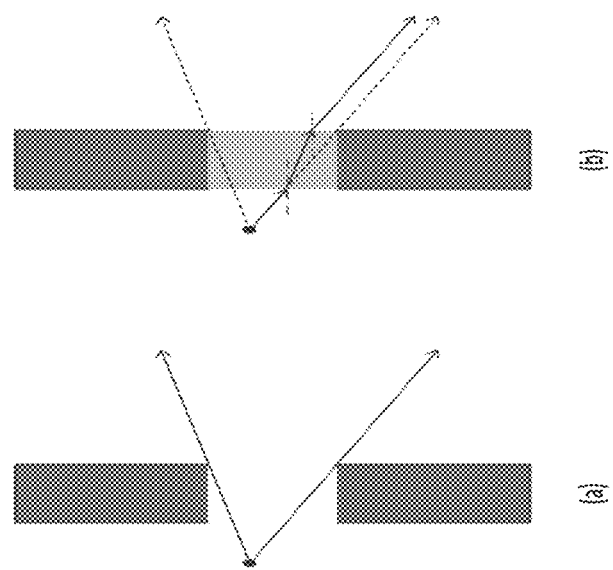
FIG. 41A
FIG. 41B

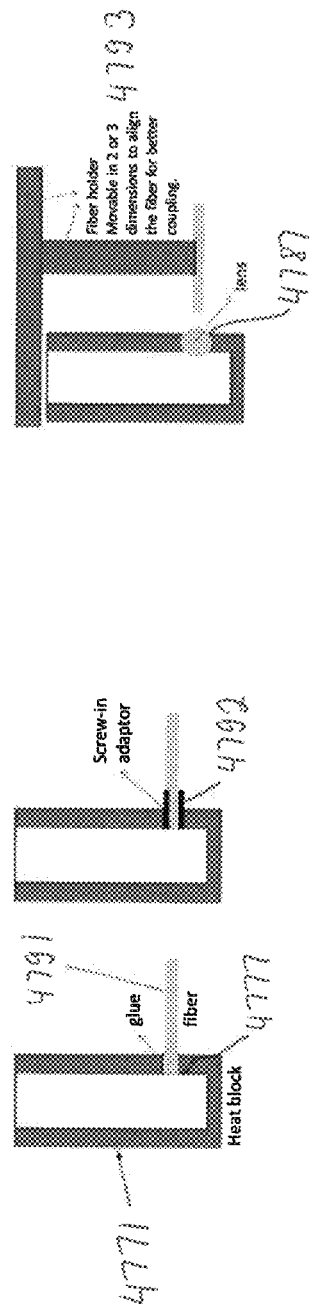

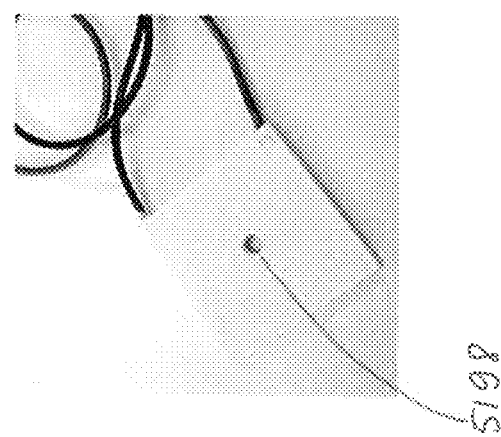
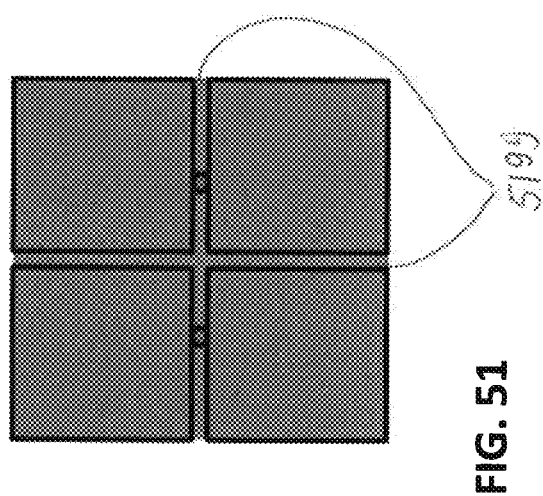
FIG. 51

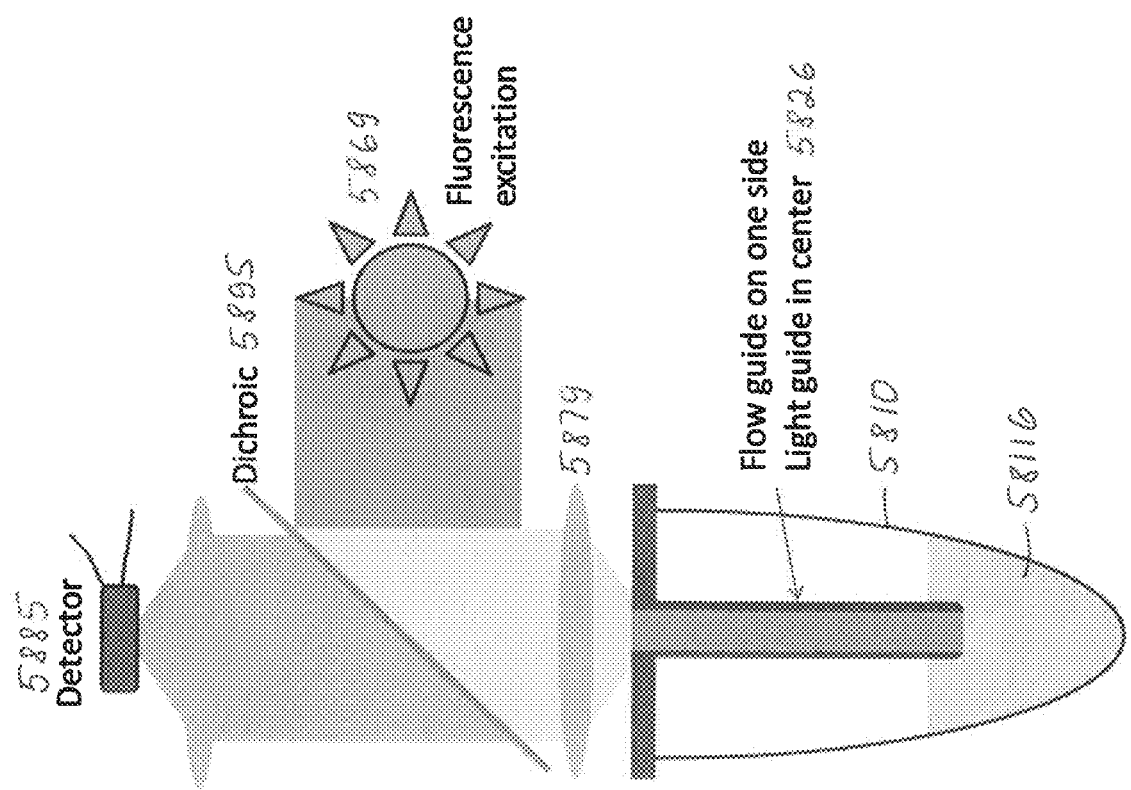

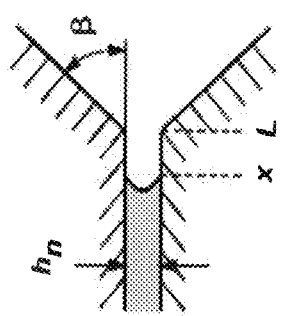
FIG. 60A
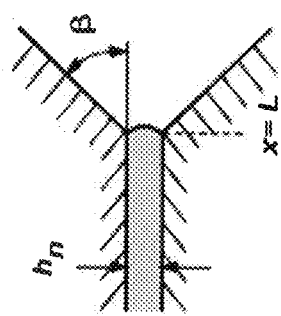
FIG. 60B
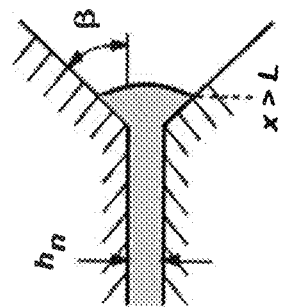
FIG. 60C
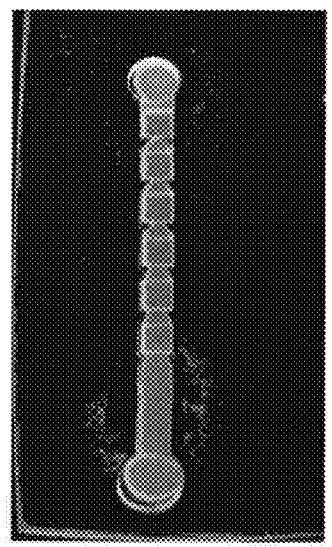
FIG. 61
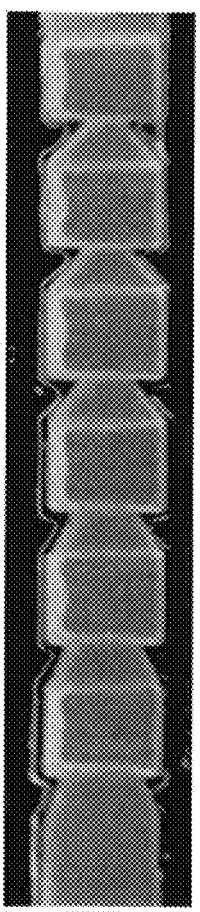

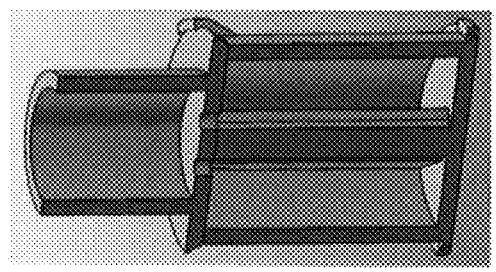
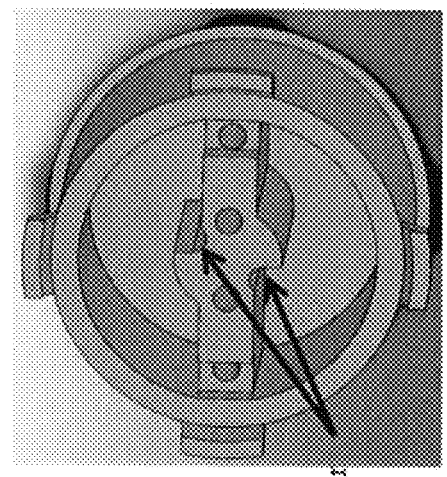
FIG. 66C

SAMPLE-TO-ANSWER SYSTEM FOR MICROORGANISM DETECTION FEATURING TARGET ENRICHMENT, AMPLIFICATION AND DETECTION

This application claims the benefit of U.S. Provisional Patent Application No. 62/270,987 filed on Dec. 22, 2015, U.S. Provisional Patent Application No. 62/270,990 filed on Dec. 22, 2015, U.S. Provisional Patent Application No. 62/271,001 filed on Dec. 22, 2015, U.S. Provisional Patent Application No. 62/270,999 filed on Dec. 22, 2015, U.S. Provisional Patent Application No. 62/270,997 filed on Dec. 22, 2015, U.S. Provisional Patent Application No. 62/270, 994 filed on Dec. 22, 2015, and U.S. Provisional Patent Application No. 62/270,992 filed on Dec. 22, 2015, each of which are incorporated herein by this reference.

FIELD OF THE INVENTION

The present invention relates to sample-to-answer systems for detecting the presence of microorganisms in a sample, cartridges for use systems for detecting the presence of microorganisms in a sample, and methods relating to the detection of microorganisms in a sample, such as bacteria.

BACKGROUND

Several simple, rapid, Point-of-Care (POC) or Point-of-Need (PON) diagnostic systems and tests exist in the market, some of which have obtained a CLIA-waiver. The benefit of these systems and tests is that they can provide diagnostic results within the timeframe of a patient visit to a medical practitioner or clinic. This can be beneficial to patient health, especially in developing countries where testing locations are a significant distance from patients, and many do not return to receive their test results.

One area in which POC and PON systems are of particular relevance is STD testing. Some STD's are asymptomatic in a number of infected individuals, and can be spread during the time between testing and result. While these POC and PON tests are rapid, many of them show poor performance for sensitivity, specificity, and positive predictive values (PPV).

Robust sample prep is generally not rapid enough for point of need/point of care. Some new methods have been developed but they are generally not fully automated. Causative microorganisms are often present in sufficient numbers in samples but generally are present at low concentration. As a result, effective POC or PON systems need to consider enrichment of target microorganisms by a process that concentrates the targets to facilitate rapid detection. When sample enrichment is used, processing time can be shortened. Since mare targets are available for amplification, the sample preparation process can be more crude and performed faster.

Filtration methods have been used for sample preparation as part of nucleic acid amplification tests such as those done using PCR. However, these methods are too often labor intensive.

Filter materials can also introduce potential amplification inhibitors such as glass fibers, dust, etc. Further, a multitude of possibly inhibitory substances exist within the samples themselves and care is required to ensure those do not end up in the lysate. In addition, if samples are filtered through a dry filter, inhibitors can be absorbed into the filter. These inhibitors may later be released during the elution step, adversely affecting amplification reactions such as PCR.

Nucleic Acid Amplification Tests (NAATs) show much higher sensitivity and specificity, but are often too complex for POC or PON systems—involving multiple manual steps, and requiring laboratory hardware such as centrifuges or biosafety hoods. There is a need for a simplified, automated NAAT test that can bring high accuracy to the POC environment.

The device simplifies and automates the processes required for Nucleic Acid Amplification Testing (NAAT), allowing it to be used in POC/CLIA-Waived applications. This simplified NAAT delivers higher sensitivity and specificity than other technologies currently being used in POC/CLIA-Waived applications.

SUMMARY OF THE INVENTION

The present invention relates to sample-to-answer systems for detecting the presence of microorganisms in a sample, cartridges, devices and systems for same.

Thus, in one aspect, the disclosure provides a method for analyzing a biological sample for the presence of a target of interest, the method comprising adding the biological sample to a sample chamber comprising a filter; enriching the biological sample; washing the sample by releasing a washing fluid into the sample chamber; drawing the washing fluid through the filter, wherein the washing fluid passed through the filter is stored in the waste chamber; releasing a lysis fluid into the sample chamber; applying heat to the filter and the biological sample to produce a lysate; moving the lysate to at least one reaction chamber; applying heat to the at least one reaction chamber; performing a reaction in the at least one reaction chamber; and monitoring the at least one reaction chamber to determine whether the target of interest is present in the biological sample.

In a second aspect, the present disclosure provides a system for analyzing a biological sample comprising a cartridge, the cartridge comprising a sample chamber, wherein the sample chamber comprises a filter; a sample wash system; a waste chamber; a lysis system; an aliquoting system, at least one reaction chamber, wherein said aliquoting system delivers at least one aliquot of fluid to each of at least one reaction chamber; and a device, the device comprising a cartridge receptacle; a sample heating system; a reaction chamber heating system; a detection system; and, a processing unit, wherein said processing unit is configured to perform an analysis of the output of the detection system, wherein said analysis provides information about the biological sample.

In a third aspect, the present disclosure provides an aliquoting module comprising a reaction chamber in fluid communication with a supply channel, and, a fluidic inlet in fluidic communication with the reaction chamber.

In a fourth aspect, the present disclosure provides an aliquoting module comprising a reaction tube in fluid communication with an inlet port, a floating object with its shape matching an inlet mouth, and a pressure port in fluid communication with the reaction tube.

In a fifth aspect, the present disclosure provides A method for aliquoting fluid comprising drawing fluid from a supply channel into a reaction tube through a fluidic inlet by applying a negative pressure to a pressure port in communication with the reaction tube, wherein the fluid starts to fill from the bottom of the reaction tube guided by a flow guide inside the reaction tube until the fluid reaches a target level in the reaction tube and fills a central column leading to a gas permeable membrane filter; wherein the filter stops the fluid flow; and wherein the flow guide breaks the continuous fluid flow coming from the fluidic inlet and isolates an aliquoted reaction volume in the reaction tube from the rest of the upstream fluid in the fluidic inlet.

In a sixth aspect, the present disclosure provides a method of controlling fluid flow comprising providing a microfluidic channel having at least one series of capillary stop valves, and introducing fluid into the microfluidic channel, wherein the capillary stop valves prevents fluid flow past the stop valves.

In a seventh aspect, the present disclosure provides a method of rapid dna/rna quantification that comprises a nanofluidic device comprising a thermally conductive substrate including thin film heaters on one side and an array of nL holes in the other side, a flexible cover initially positioned apart from said substrate by a gap, wherein said gap allows an amplification liquid to flow over the array in a loading step, and wherein subsequent to the loading step, said gap being reduced such that the substrate and cover are brought into intimate contact to seal said array in a sealing step.

In an eighth aspect, the present disclosure provides a system and device for rapid dna/rna quantification comprising a thermally conductive substrate including thin film heaters on one side and an array of nL holes in the other side, and a flexible cover used to seal said array following the introduction of an amplification liquid.

In a ninth aspect, the present disclosure provides a rotatable cartridge for analyzing a biological sample for the presence of a target of interest, the cartridge comprising a first element comprising a cap having a sample and lysis chamber containing a capture filter, wherein at least one outlet is present under the capture filter; a second element comprising a waste chamber having a center portion comprising at least two through channels disposed within a solid section, and a pneumatic port; a third element comprising at least two channels extending from the top of the third element through a top portion of the third element, at least one hydrophobic filter located on the top portion of the third element and offset from the at least two channels, and at least one reaction chamber disposed below the top portion of the third element, such that the at least two channels are in fluid communication with the least one reaction chamber; wherein, the first, second and third elements are vertically stacked and are rotatable with respect to each other around a central axis, such that the outlets, channels, chambers, and filters can be placed into and out of fluidic communication from each other by rotating one or more of the elements.

In a tenth aspect, the present disclosure provides a method of analyzing a biological sample for the presence of a target of interest comprising use of a rotatable cartridge.

In an eleventh aspect, the present disclosure provides a system for automated pre-wetting of a filter comprising a tank for holding a sample; a means for holding the sample back, preventing it from wetting the filter; a means for releasing a benign wetting fluid used to pre-wet said filter; and a means for releasing said sample, allowing it to be filtered.

In a twelfth aspect, the present disclosure provides a heat block for providing heat to an amplification vessel which features two or more optical ports in which at least one of said ports is used to excite a fluorescent dye housed within said vessel and at least one of said ports is used to detect the fluorescence generated by said dye.

In a thirteenth aspect, the present disclosure provides methods for micro machining small holes to accommodate optical detection through an opaque material.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention.

In FIG. 12A, the check valve is closed and fluid flows through the filter. In FIG. 12B, the check valve is open, creating space between the valve wall and the filter, allowing fluid to flow around the edge of the filter.

FIGS. 14A-B show a waste chamber diagram for the cartridge as provided in FIG. 5. FIGS. 14C-D show an aliquoter diagram for the cartridge as provided in FIG. 5.

FIG. 37A demonstrates an exemplary heat block in partial sectional view. Arrows show the direction of excitation light (entering) and emission light (exiting). FIG. 37B demonstrates a heat block used for thermal cycling of two thin-walled PCR tubes.

FIG. 41A shows a chamfering angle of excitation ports matching or larger than the LED cone angle ($\theta$). FIG. 41B shows the change in angle of light passed through an opening containing a filler.

FIG. 47A demonstrates a fiber tailed heat block for fluorescence detection. Fiber is directly coupled to the heat block. FIG. 47B demonstrates a fiber tailed heat block for fluorescence detection. Fiber is coupled to the heat block via a lens.

FIG. 51 demonstrates: Left: a custom Peltier designed to include holes in desired positions. Right: an array of Peltier modules assembled with gaps large enough to sample optics through the fan, heat sink, Peltier, and heat block.

FIG. 58A demonstrates a method for fluorescence detection according to one embodiment of the present invention.

FIGS. 60A-C provide stop valve diagrams.

FIG. 61 demonstrates a progressive stop valves system.

FIG. 64 (right) demonstrates progressive stop valves in the same chip after being put under stress.

FIG. 66C shows two "filter and lysis" chamber outlets aligned with waste channels.

DETAILED DESCRIPTION OF PREFERRED EMBODIMENT

Figure 1A:
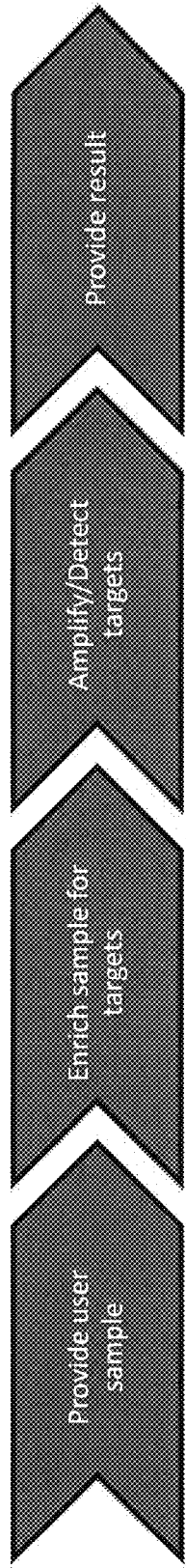
FIG. 1A is a diagram illustrating a sample-to-answer process featuring sample enrichment, amplification, and detection. Amplification and detection may be performed concurrently such as in real-time PCR.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, immunology, electrical and mechanical engineering, fluidics, and manufacturing techniques such as injection molding, which are within the skill of the art.

As used herein, "genetic material" means any nucleic acid, including DNA and RNA. Thus, genetic material may include a gene, a part of a gene, a group of genes, a fragment of many genes, a molecule of DNA or RNA, molecules of DNA or RNA, a fragment of a DNA or RNA molecule, or fragments of many DNA or RNA molecules. Genetic material can refer to anything from a small fragment of DNA or RNA to the entire genome of an organism.

It should be appreciated that any materials, volumes, times, temperatures, pressures, or the like stated within the present disclosure are exemplary and should not be interpreted as limiting the scope of the disclosure.

The present disclosure provides a sample to answer system and methods of use for analyzing a sample for the presence of one or more targets of interest. In one embodiment, as provided in FIG. 1A, the sample to answer system comprises the steps of providing a sample, enriching the sample for one or more targets of interest, amplifying and detecting the target(s) of interest, and providing as a result a determination of the presence or absence of the target(s) of interest in the sample. In one embodiment, the sample provided is a crude sample, that is, one which has not undergone any sample processing after the sample was obtained.

In one embodiment, the sample may be one or more of the following types: bronchoalveolar lavage, urine, blood, saliva, cerebrospinal fluid, endocervical, vaginal, buccal, nasal, tears, serum, plasma, biopsy sample, skin, stool, sweat, synovial fluid, wound fluid, dental scraping, and penile swabs. Samples can be a liquid, semi-solid, or a solid, for instance with respect to skin sample or biopsy.

The present disclosure includes analyzing the sample for targets of interest, including, but not limited to: microorganisms, food pathogens, infectious agents, and parasites, examples of which include bacteria, viruses, fungi, and yeast. More specific applications and targets of interest within the scope of the present disclosure include, without limitation: *Trichomonas vaginalis, Chlamydia trachomatis,* and *Neisseria gonorrhoeae,* syphylis, antibiotic resistant strains, HIV, Zika, human papillomavirus, yeast, vaginal microbiome profiling, vaginosis panel, fungi, animal health targets, listeria, *E. coli,* sepsis, herpes, HCV, RSV, CMV, HSV, Group B strep, influenza, and others known to skill in the art.

In one embodiment of the present disclosure as shown in FIG. 1A, enrichment of the target of interest may include concentrating the targets of interest within the sample. Enrichment may include separating the targets of interest from a portion of the sample by methods including filtering, centrifugation, sedimentation and other methods whereby non-target fluid and/or other sample components are removed from the targets of interest. Following enrichment of the target of interest, the target may be amplified by amplification techniques known in the art, and specifically by nucleic acid amplification reactions. Nucleic acid amplification reactions may include polymerase chain reaction (PCR), ligase chain reaction (LCR), strand displacement amplification (SDA), isothermal amplification and loop-mediated isothermal amplification, among others. Such amplification reactions amplify the quantity of the targets of interest present within a sample to a quantity suitable for detection. Monitoring and/or detection of the results of the amplification reaction can occur simultaneous to the amplification reaction occurring. For instance, quantitative PCR (qPCR) or real-time PCR may be used to monitor and/or detect the amplification reaction as it progresses in real time.

Several different real-time detection chemistries now exist to indicate the presence of amplified DNA. Most of these depend upon fluorescence indicators that change properties as a result of the PCR process. Among these detection chemistries are DNA binding dyes (such as SYBR® Green)

that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

Figure 1B:
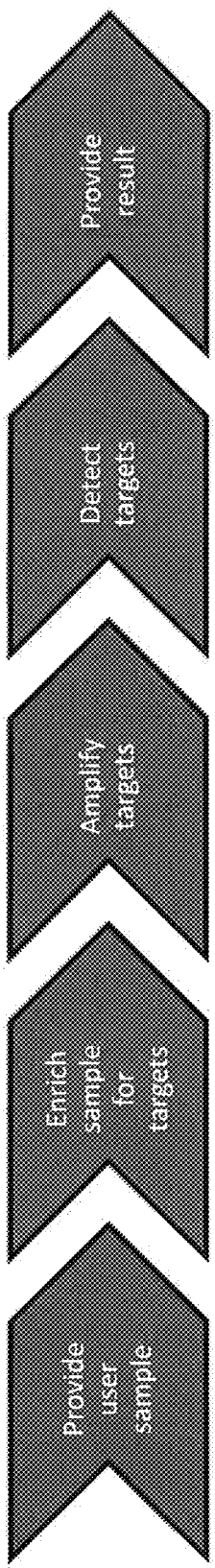
FIG. 1B is a diagram illustrating a sample-to-answer process featuring sample enrichment, amplification, and detection.

In another embodiment, as shown in FIG. 1B, detection can be performed following completion of the amplification reaction. Detection occurring following completion of the amplification reaction may include end-point detection methods such as fluorescence quantification or high-resolution thermal melt analysis (HRM). Irrespective of the timing of the monitoring/detection step, the detection of a target of interest, or the absence of the detection of a target of interest then allows for either a qualitative positive/negative result or a quantitative result to be provided.

In one embodiment, the monitoring system can be a fluorescent dye imaging system similar to that used in U.S. Pat. No. 9,278,321, which is incorporated herein by reference in its entirety. According to one embodiment of the present invention, the fluid in the reaction chamber can be excited by an excitation device and light fluoresced from the sample can be detected by a detection device. An example of one possible excitation device and detection device forming part of an imaging system is illustrated in U.S. Patent Application Publication No. 2008/0003593 and U.S. Pat. No. 7,629,124 which are incorporated herein by reference in their entirety.

To monitor an amplification process, including a PCR process, the system can include an detection system. Imaging system can include an excitation source, an image capturing device, a controller, and an image storage unit. Other aspects of a suitable imaging system in accordance with some aspects of the invention are disclosed in U.S. Pat. No. 8,058,054 to Owen et al., incorporated herein by reference in its entirety.

A detector can be implemented using a conventional digital camera, such as the Canon 5D digital SLR camera, a CMOS sensor, a photodiode, optical fiber, or a digital video camera. In one embodiment, detector is implemented using an electron multiplying charge coupled device (EMCCD). The detector can be configured and arranged to detect emissions from the reaction chamber and to output image data corresponding to the detected emissions. Other details of imaging systems that can be used in connection with the systems and methods of the present invention, as well as further details regarding their use, are described in U.S. Pat. No. 8,962,252 to Liang et al., the disclosure of which is hereby incorporated by reference.

Figure 1C:
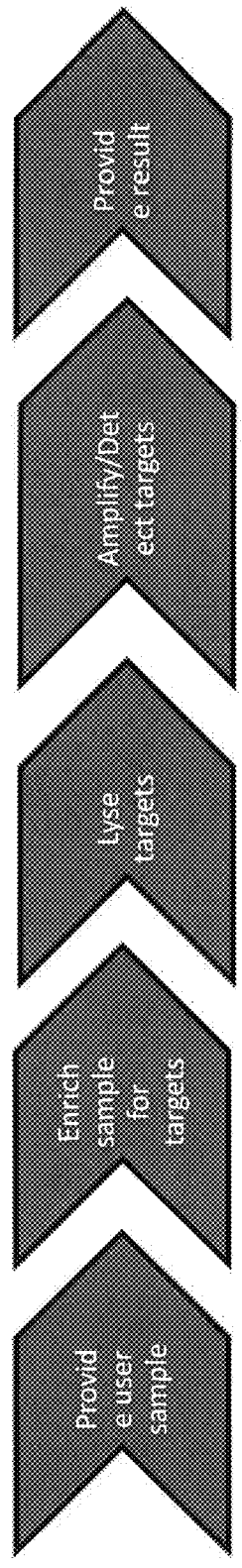
FIG. 1C is a diagram illustrating a sample-to-answer process featuring sample enrichment, lysis, amplification, and detection.

In another embodiment of the present disclosure as shown in FIG. 1C, a lysis process follows the enrichment step. The lysis process may include one or more of heat lysis, chemical lysis, or mechanical lysis. In another embodiment, the lysis process can utilize one or more of: sonication, bead-beating, micro-knives, freeze/thaw cycles, ProK, glucosydases, Prep Gem, laser/IR heating, inductive Heating, electroporation, pressure lysis, cold shock, osmotic shock, bead capture, and targeted IR with nanoparticles.

Multiple configurations of the specific components of the system, cartridge and device identified in the present disclosure are possible in order to provide the functionality described herein. Exemplary, non-limiting, configurations of these components are described with reference to the figures.

Figure 2A:
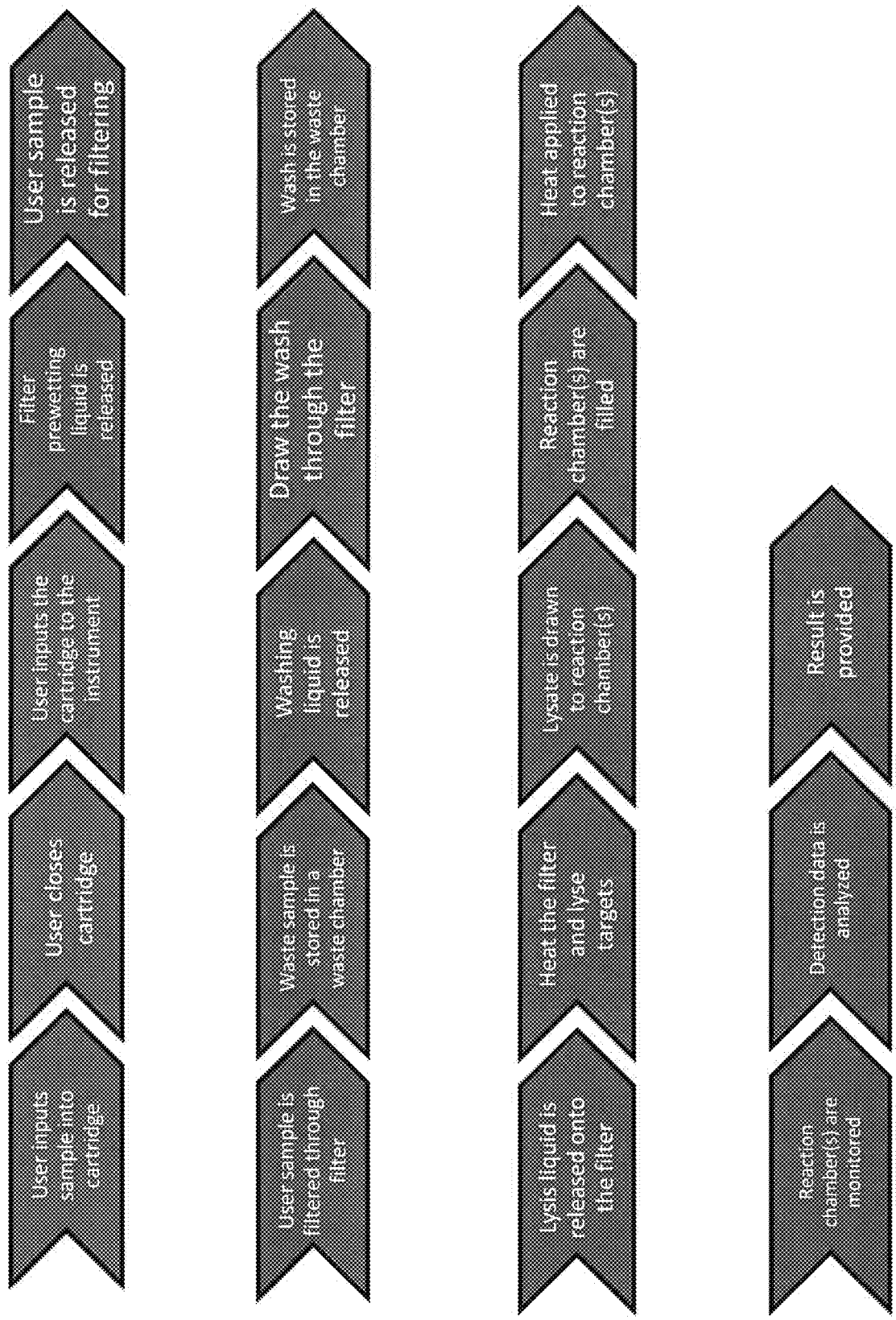
FIG. 2A is a diagram illustrating a sample-to-answer process using filtration enrichment. The heating of reaction chambers may comprise thermal cycling (such as that required for PCR).

One embodiment of the present disclosure provides a process as described in FIG. 2A. A user places a sample into the cartridge, closes the cartridge, and inserts the cartridge into the device. A prewetting fluid is optionally released onto the filter. The sample is released from the initial sample tank into the lysis chamber containing the filter. The sample is filtered through the filter, with waste material passed through the filter stored in a waste chamber. A washing fluid is optionally then released into the lysis chamber and passed through the filter. The washing fluid is then also stored in the waste chamber. A lysis fluid can then be released onto the filter, and the filter is then heated in order to lyse any targets of interest remaining on the filter. The resulting lysate is then moved to a reaction chamber. Heat is applied to the reaction chamber, and the reaction chamber is monitored for detectable properties. Such monitoring can occur simultaneous to, or subsequent to, the heat being applied to the reaction chamber. Data obtained by monitoring the detectable properties is then analyzed, and a result is presented indicating the presence or absence of a target of interest.

In one aspect of the present invention, a method and a system for analyzing a biological sample for the presence of a target of interest are provided. The biological sample is added to a sample chamber comprising a filter. Next, the biological sample is enriched and washed by releasing a washing fluid into the sample chamber. The next step is directed to drawing the washing fluid through the filter. The washing fluid passed through the filter is stored in the waste chamber. Then, a lysis fluid is released into the sample chamber. Heat is applied to the filter and the biological sample to produce a lysate. Next, the lysate is moved to at least one reaction chamber to which heat is applied. A reaction is performed in the at least one reaction chamber. The at least one reaction chamber is monitored to determine whether the target of interest is present in the biological sample.

In one embodiment, the step of enriching the sample comprises: (a) filtering the biological sample through a filter, wherein fluid passed through the filter is stored in a waste chamber and the remainder of the biological sample remains in the sample chamber; or, (b) magnetically labeling the targets of interest within the sample and subjecting the labelled sample to a magnetic field. By way of example and without limitation, a magnetic field is created using a solenoid.

In a further aspect of the invention, the step of lysing the sample comprises: (a) applying heat to the filter and the biological sample to produce a lysate; or (b) subjecting the biological sample to an electric field to cause electroporation. The electric field can be applied to a sample as it travels through a channel to the reaction chamber. Furthermore, the steps of adding a sample to a filter through obtaining a lysate can comprise using a spin column filtration configuration or a syringe based cartridge.

In one embodiment, the method additionally includes prewetting the filter comprising releasing a prewetting fluid. Washing the sample comprises releasing a washing fluid. The sample is held in a first portion of the sample chamber until prewetting the filter occurs. In yet another embodiment, the prewetting liquid is released by crushing a blister pack, or by using a plunger to burst a blister pack. By way of example, the prewetting liquid is water.

In one embodiment, a check valve is present in the sample chamber to separate the first portion of the chamber from a second portion. The second portion of the sample chamber contains the filter. By way of example, the target of interest can be selected from the group consisting of: *Trichomonas vaginalis*, *Chlamydia trachomatis*, and *Neisseria gonorrhoeae*.

Furthermore, a sample processing control is additionally provided in the sample chamber with the biological sample. The biological sample can be selected from the group consisting of: bronchoalveolar lavage, urine, blood, saliva, cerebrospinal fluid, endocervical, vaginal, buccal, nasal, tears, serum, plasma, biopsy sample, skin, stool, sweat, synovial fluid, wound fluid, dental scraping, and penile swab.

The biological sample is released for filtering by application of a negative pressure below a check valve crack pressure. The biological sample is filtered through the filter using a negative pressure from downstream of the filter or positive pressure from upstream of the filter. In one embodiment, the washing liquid is water. In one embodiment, the lysis liquid is released onto the filter by crushing a blister pack containing a frangible seal.

In yet another embodiment, resistive heaters are used to rapidly heat the filter and lyse the bacteria in the biological sample. At least one of the resistive heaters is attached to a heat block. The heat block is configured to have the same interior shape as the outer shape of the sample chamber.

In one aspect of the invention the lysate is drawn past a Y-branch separating waste from reaction channels. In yet another embodiment, the lysate is drawn past a second Y-branch separating the lysate into at least one measured portions for at least one reaction. Next, the lysate is dispensed into at least one reaction chamber.

In one embodiment, the reaction chamber contains dried reagents. To mix the dispensed lysate and the dried reagent, the reaction chamber is heated. The at least one reaction chamber fills until a hydrophobic valve is sealed, corresponding to a desired reaction volume. The reaction performed in the reaction chamber may be an amplification reaction, including PCR.

In one embodiment, a fluorescence signal is monitored during a PCR reaction using two color channels. At least one color channel is used for a control signal. A quantification cycle is determined for each color and compared to cutoffs to return results for each assay. Monitoring the reaction chamber for the sample processing control will confirm whether the sample has been captured and lysed. By way of example, the sample processing control can be selected from a dried micro-organism, a plasmid construct, or polynucleotide. In one embodiment, the sample processing control is a human cell or DNA sequence.

Figure 2B:
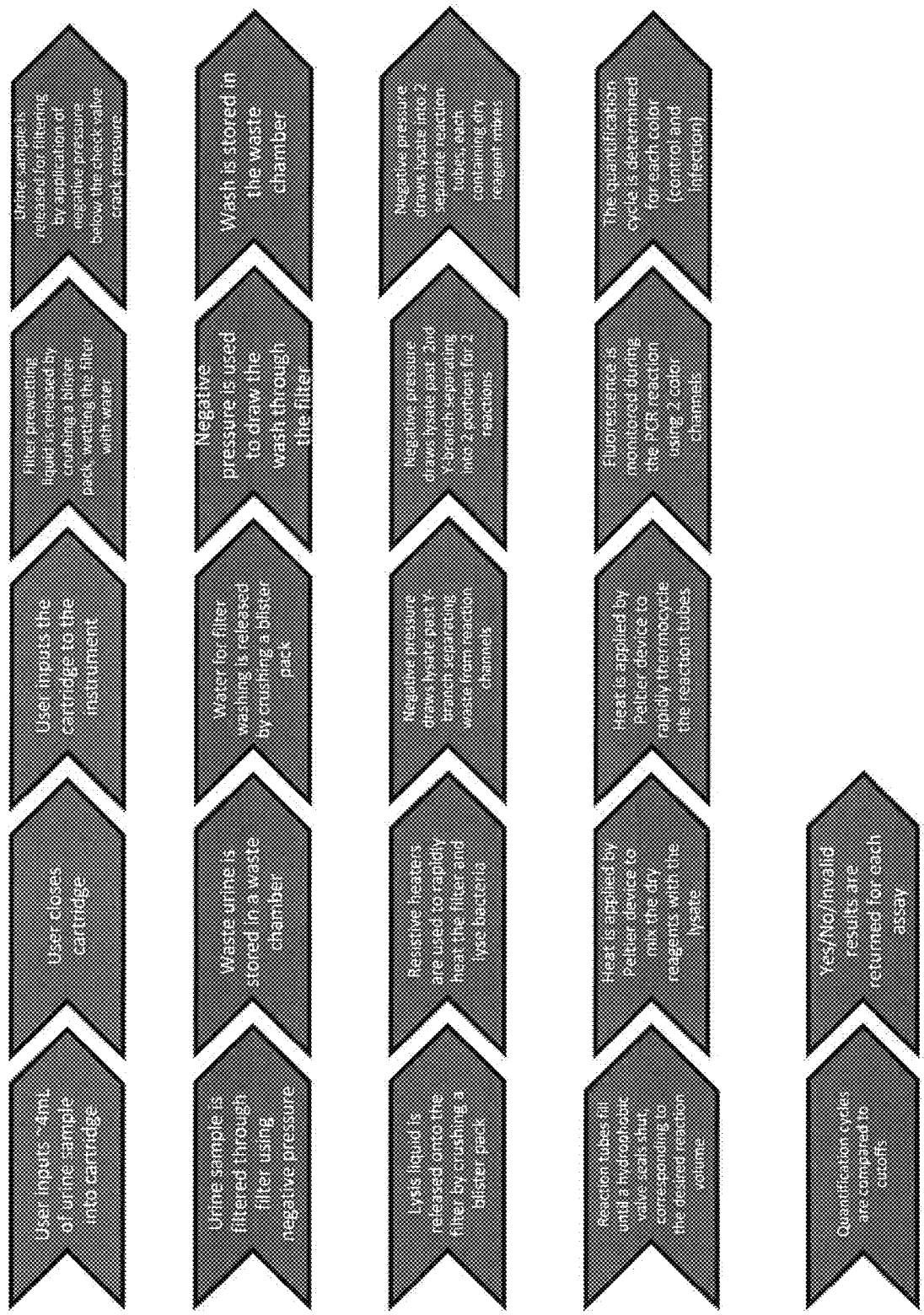
FIG. 2B demonstrates sample-to-Answer diagnostic for multiplex urine assay.

In another embodiment of the present disclosure, a process is provided according to FIG. 2B. A user places a sample such as a urine sample into the cartridge, closes the cartridge, and inserts the cartridge into the device. A prewetting fluid is optionally released onto the filter through a port. In one embodiment, release of the prewetting fluid is by means of crushing, piercing, or otherwise releasing a fluid from a blister pack. In some embodiments, the prewetting fluid released is water. The sample is released from the initial sample tank into the lysis chamber containing the filter. In one embodiment, the sample is released from the initial sample tank chamber by application of negative pressure in an amount below the check valve crack pressure amount. The sample is filtered through the filter by application of negative pressure, with the urine waste material passed through the filter stored in a waste chamber. A washing fluid is optionally then released into the sample chamber and passed through the filter by application of negative pressure. In one embodiment, release of the washing fluid is by means of crushing, piercing, or otherwise releasing a fluid from a blister pack. In some embodiments, the wash fluid released is water. The washing fluid is then also stored in the waste chamber. A lysis fluid can then be released onto the filter. In one embodiment, release of the lysis fluid is by means of crushing, piercing, or otherwise releasing a fluid from a blister pack. The filter is then heated in order to lyse any targets of interest remaining on the filter. In one embodiment, resistive heaters may be used to heat the filter. The resulting lysate is then moved to a reaction chamber. In one embodiment, movement of the lysate is caused by application of negative and/or positive and/or a combination of both positive and negative pressure which draws the lysate through a main channel past a Y-branch separating a channel leading to a waste chamber from channel(s) leading to reaction channel(s). The lysate is then moved into the reaction chamber. In some embodiments where more than one reaction chamber is present, the lysate can be moved by application of negative/positive pressure past a further Y-branch in the main channel to be separated into two or more portions of the lysate to be subjected to two or more reactions. The portions of the lysate can then be moved by application of negative pressure into the separate reaction chamber(s). In some embodiments, a combination of negative/positive pressure is used to drive the lysate into the reaction chambers. The reaction chamber(s) fill until a hydrophobic valve seals shut, such that the desired reaction volume is present in the chamber. In one embodiment, the reaction chamber(s) can contain dried reagents necessary for an amplification process. Heat is applied to the reaction chamber. In some embodiments, heat can be applied by means of a peltier device. The heat application causes the mixing of the dry reagents and the lysate. Heat can then be applied to rapidly thermocycle the reaction chamber(s). In some embodiments, the thermocycling is performed such that a PCR reaction can occur. Simultaneous to or subsequent to the thermocycling, the reaction chamber(s) is monitored for detectable properties. In one embodiment, the detectable property monitored is fluorescence emissions. In another embodiment, the fluorescence emissions are monitored using two or more color channels. Such monitoring can occur simultaneous to, or subsequent to, the heat being applied to the reaction chamber. In embodiments where two or more color channels are used for monitoring, one or more color channels can be used for the sample lysate, and one or more can be used for a control sample. Data obtained by monitoring the detectable properties is then analyzed to determine a quantification cycle for each color channel. Quantification cycles are compared to pre-determined cutoff levels, and a result is presented indicating the presence or absence of a target of interest or that the run was invalid.

In one embodiment, in a clinical setting, a sample is obtained from a patient into a standard collection device. The sample can be provided in a standard collection cup, a swab and associated transport tube, a syringe, or other means known in the art. A clinician or nurse transfers a portion of the sample, for example, via bulb pipette or medicine dropper, into the sample tank. Once the sample is inserted, the vented cap can be screwed shut to seal the cartridge, and the cartridge is inserted into the device. A prewetting liquid can enter the lysis chamber from the lysis fluid inlet to saturate the capture filter, preventing it from absorbing fluid from the sample and introducing inhibitors into the lysate. Negative pressure can then be applied to the check valve, causing it to open and release the sample from the sample tank into the lysis chamber. The sample is pulled through the capture filter and into the waste chamber, trapping any targets of interest, for example, bacterial cells, on top of and/or within the filter. A wash fluid is released from the lysis fluid inlet, and fills the lysis chamber. Any remaining sample, along with any corresponding inhibitors, for instance PCR inhibitors, is absorbed and removed when the wash fluid is drained to the waste chamber. The lysing fluid is then released into the lysis chamber. The lysing fluid and trapped targets of interest are heated, lysing the targets of interest on top of the filter. Any genetic material from the targets of interest is retained in the lysate, and the lysate is pulled through the lysis outlet and into the main channel. A reaction chamber is located below the aliquoter and can be pre-loaded with reagents. The aliquoter features draws the lysate through the main channel and dispenses a pre-determined reaction volume of lysate into the reaction chamber, which is mixed with reagents and undergoes the desired reaction.

Figure 3A:
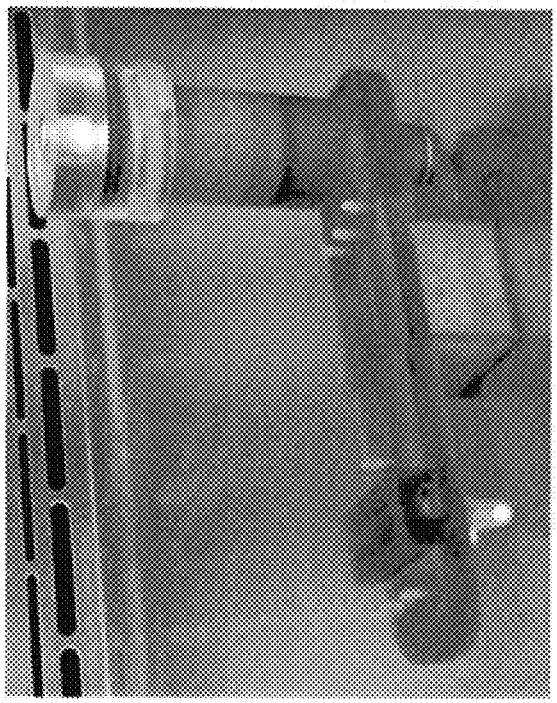
FIG. 3A demonstrates a complete 3D printed cartridge designed for urine samples.
Figure 3B:
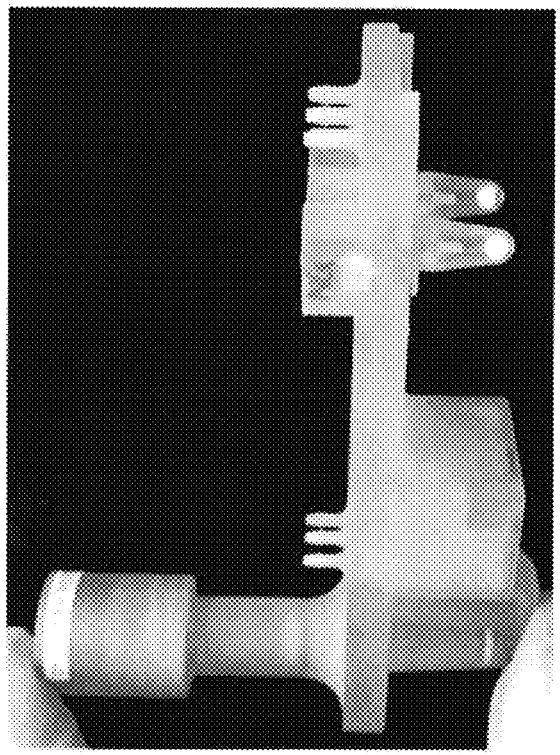
FIG. 3B demonstrates a complete 3D printed cartridge designed for swab samples.

The system provided in the present disclosure includes a cartridge and a device. The cartridge can accept a sample of multiple types, as provided herein, which may be input as a liquid, a solid, a semi-solid, or which may be introduced on a structure such as a swab. In some embodiments, there can be different cartridge configurations in order to accept different types of samples. For instance, a fluidic sample can be used in a cartridge of the type shown in FIG. 3A, while a sample obtained using a swab or similar method can be used in either the fluidic cartridge or in a separate cartridge of the type shown in FIG. 3B.

Figure 4:
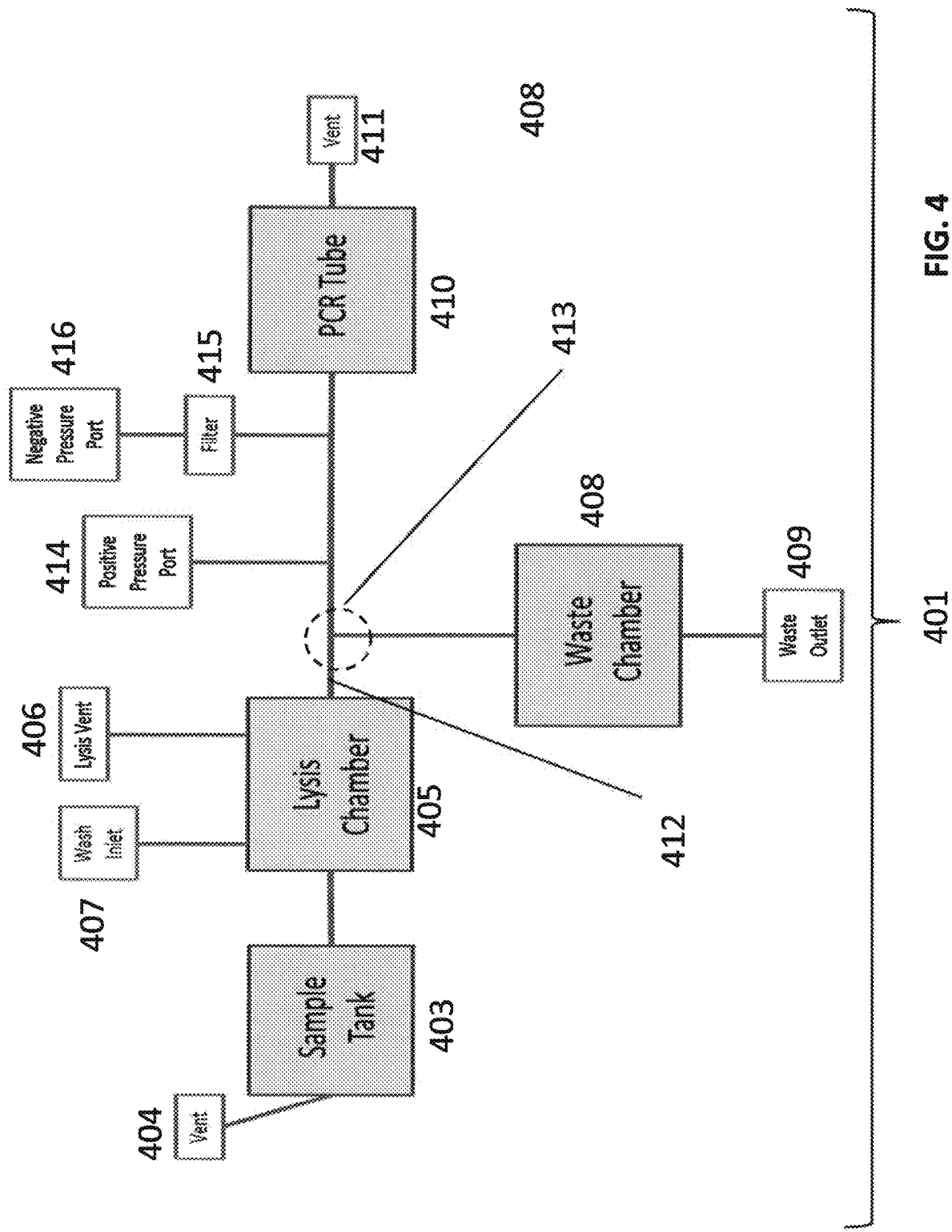
FIG. 4 demonstrates fluidic connections and functional chambers in a cartridge.

Regardless of the sample type to be inserted into the cartridge, in one embodiment the cartridge has the general layout provided in FIG. 4. The cartridge 401 has a sample tank 403 having an external vent 404. The sample tank 403 is fluidically connected to the lysis chamber 405, the lysis chamber having connected thereto an external vent 406 and a fluid inlet 407. The lysis chamber 405 is connected to both a waste chamber 408 and one or more reaction chamber(s) 410 by means of a main channel 412 that is forked, Y-branched, T-branched or has other suitable configuration 413 to allow a fluid to be selectively moved to either of the waste 409 or reaction chamber(s) 410.

Waste chamber 408 has connected thereto waste outlet port 409. The one or more reaction chamber(s) 410 is connected to an external vent 411. Main channel 412 can additionally comprise a positive pressure port 414 and/or a negative pressure port 416. Although depicted as two separate ports in FIG. 4, a single port can alternatively be used with a pressure source that can alternately provide negative and positive pressure. In one embodiment, a filter 415 can be present between main channel 412 and one or more of the ports or vents 411, 416.

Figure 5:
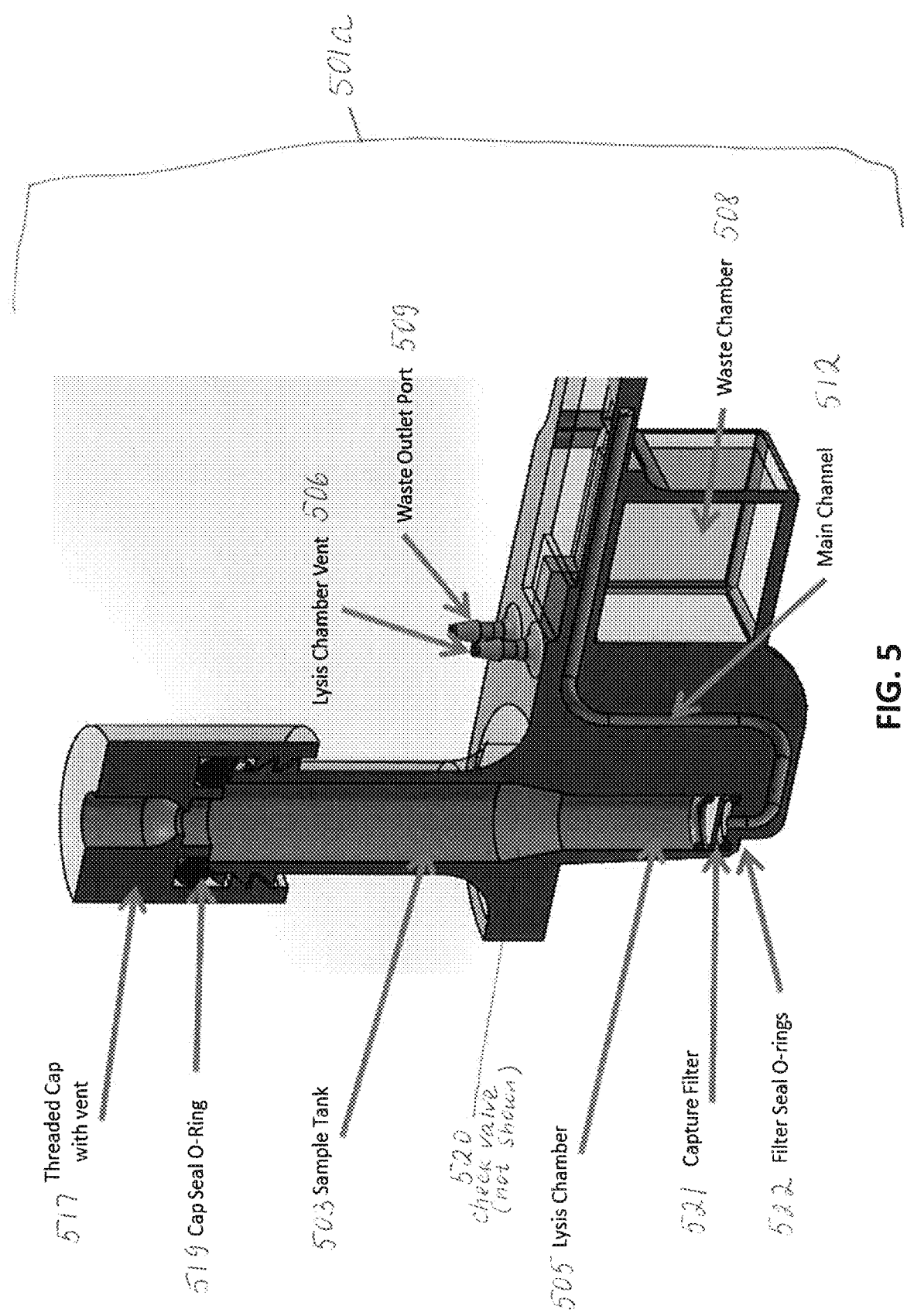
FIG. 5 demonstrates a cross-sectional view of the front half of the cartridge according to one embodiment of the present invention.

An exemplary depiction of a cross-sectional view of the front half of a cartridge 501a configured for a swab-based sample is provided in FIG. 5. Sample tank 503 is closed by means of a threaded cap 517 with a vent 518. An O-ring 519 can be used with the threaded cap 517 to prevent leakage or spillage from sample tank 503. A check valve 520 (not shown) can be located between the sample chamber 503 and the lysis chamber 505. In the embodiment shown, the sample tank 503 can be placed above the lysis chamber 505, with the check valve 520 delineating the two elements. Lysis chamber 505 has connected thereto an external vent 506. A fluid inlet (not shown) can also be connected to lysis chamber 505. A capture filter 521 can be located at the bottom of the lysis chamber 505. Filter seal o-rings 522 can be placed above and/or below the capture filter 521. Main channel 512 connects to the lysis chamber 505 below the capture filter 521 and leads to the waste chamber 508 and the reaction chamber(s) 510 (not shown). Waste chamber 508 has connected thereto a waste outlet port 509.

Figure 6:
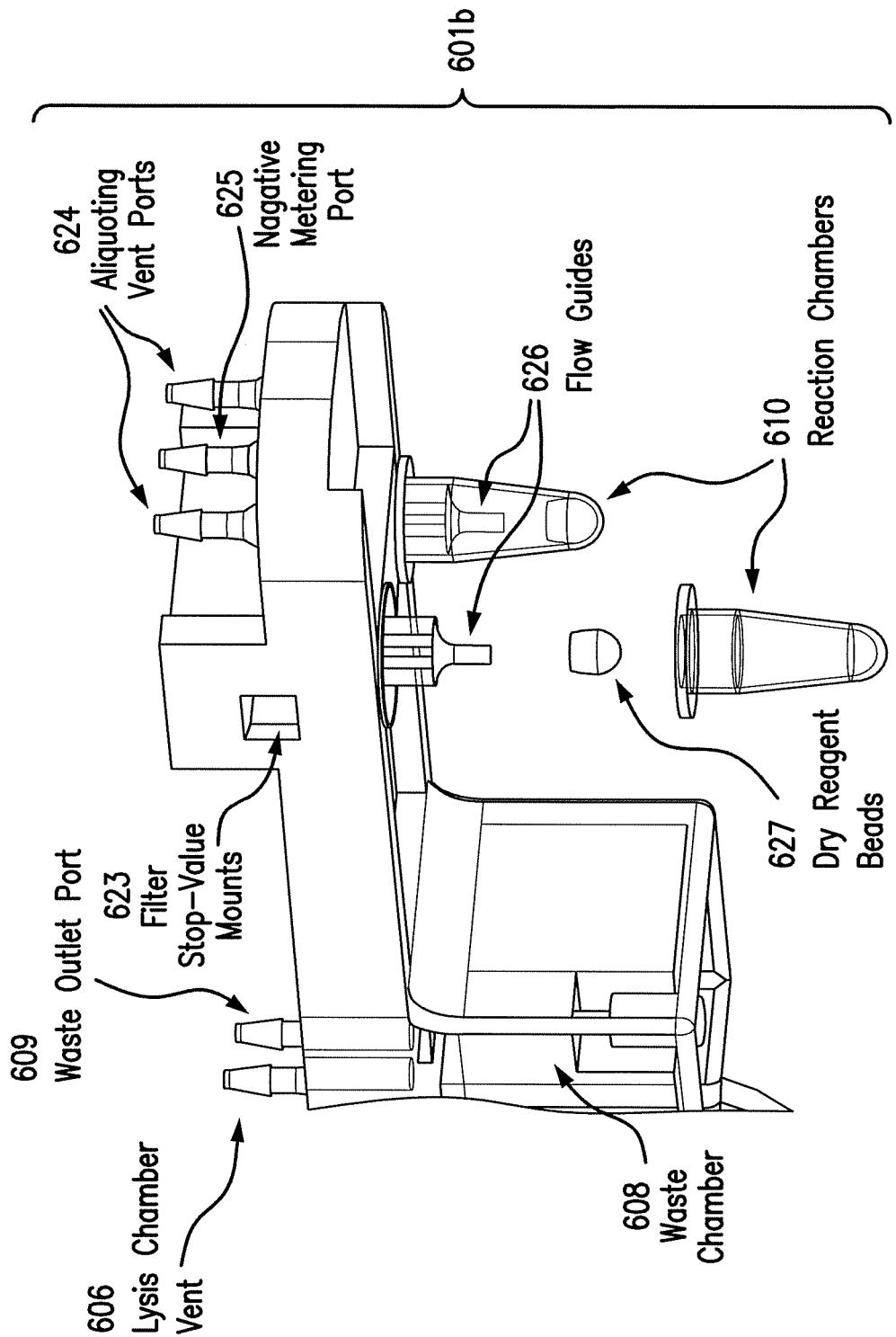
FIG. 6 demonstrates an exploded view of the back half of the cartridge of FIG. 5.

An exemplary depiction of a cross sectional view of the back half of a cartridge 601b configured for configured for a swab-based sample is provided in FIG. 6. In practice, the front half of cartridge 501a is connected to the back half of cartridge 601b to form a single cartridge. FIG. 6 depicts the waste chamber 608, lysis chamber external vent 606 and waste outlet port 609 also shown in FIG. 5 as points of reference for the alignment of the two figures to depict a single cartridge. Although the figures depict the cartridge in two halves, in practice the cartridge can be manufactured in any manner known to those of skill in the art, including, but not limited to, as a single machined, injection molded, printed or etched part, or as more than one machined, injection molded, printed or etched part that are assembled into a single cartridge.

FIG. 6 depicts the reaction chamber(s) 610, shown here as molded PCR vessels, downstream from the lysis chamber. Filter stop valve mounts 623 can be located between the metering channel (not shown) and the reaction chamber(s) 610. The filter stop-valve mounts are openings that allow insertion of a hydrophobic filter. In one embodiment, the mounts can be tapered, providing a loose initial fit for ease of insertion, and tapering to a tight fit to seal the filter to the cartridge. In another embodiment, inserting the filter stop-valve from the side improves ease of manufacture, and allows for easy removal and/or replacement. Once inserted, the mount opening can be sealed. Aliquoting vent port(s) 624 and negative metering port (625) are connected to the metering channel (not shown) downstream of the reaction chamber(s) 610. Flow guide(s) 626 can be located at the interface between the main channel and the reaction chamber(s) 610. In one embodiment, flow guides can be protrusions into the reaction chamber that help guide liquid into the reaction chamber and onto the dry reagent bead. The flow guide can be configured in any length or shape, include elongated shapes such as rectangles. In another embodiment, the flow guides minimize the presence of bubbles by guiding fluid to fill the reaction chamber from bottom to top. Each reaction chamber (610) can optionally contain necessary reagents for successful completion of the desired reaction. In one embodiment, the necessary reagents may take the form of dry reagent beads 627. In one embodiment, dry reagent beads can contain all reagents required for a PCR reaction. In another embodiment, the dry reagent beads can be inserted into the reaction chambers, which can then be assembled to the main body of the cartridge.

Figure 7:
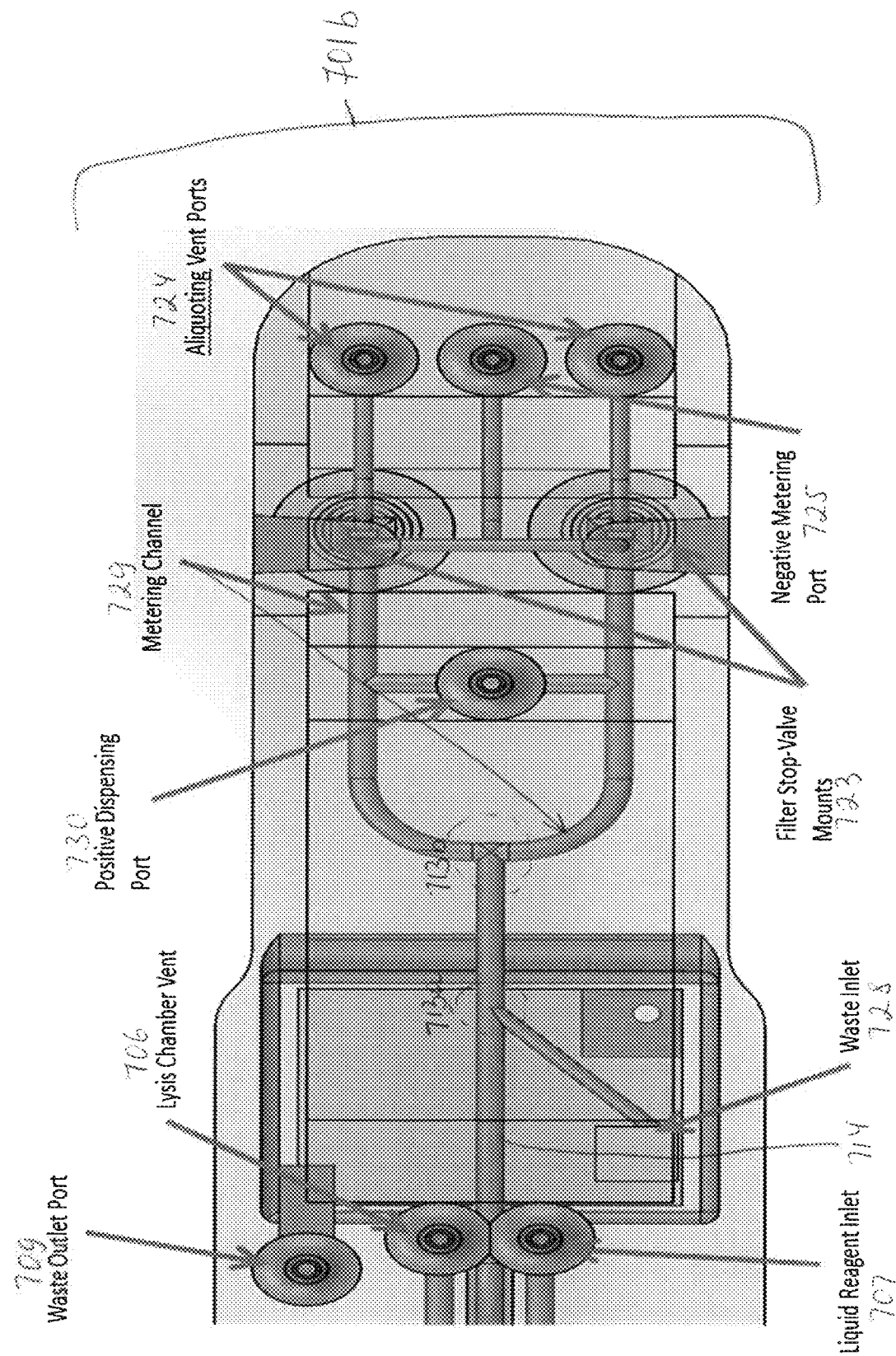
FIG. 7 demonstrates a transparent top view of the back half of the cartridge shown in FIG. 5 and FIG. 6.

FIG. 7 provides a transparent top view of the back half of a cartridge 701b, providing an exemplary depiction of the fluidic and pneumatic connections that are not visible in FIG. 6. Fluid inlet 707 and vent 706 are connected to the lysis chamber (not shown). Main channel 714 has a first Y-branch 713a that directs fluid to the waste chamber through waste inlet 728. A second Y-branch 713b connects the main channel 714 to metering channel(s) 729. A positive dispensing port 730 is connected to the meter channel(s) 729. Stop-valve filter mounts 723 are connected to each of the metering channels 729 between the Y-branch 713b and the negative metering port 725. In one embodiment, aliquoting vent ports connect to a single reaction chamber. In another embodiment, the aliquoting vent ports can have a tubing barb and can be linked to valves in the instrument. When dispensing occurs, the aliquoting vent ports can be opened to allow air to escape from the reaction chambers. Similar to other ports, they use a 1/16" ID tubing barb for ease of testing.

Figure 29:
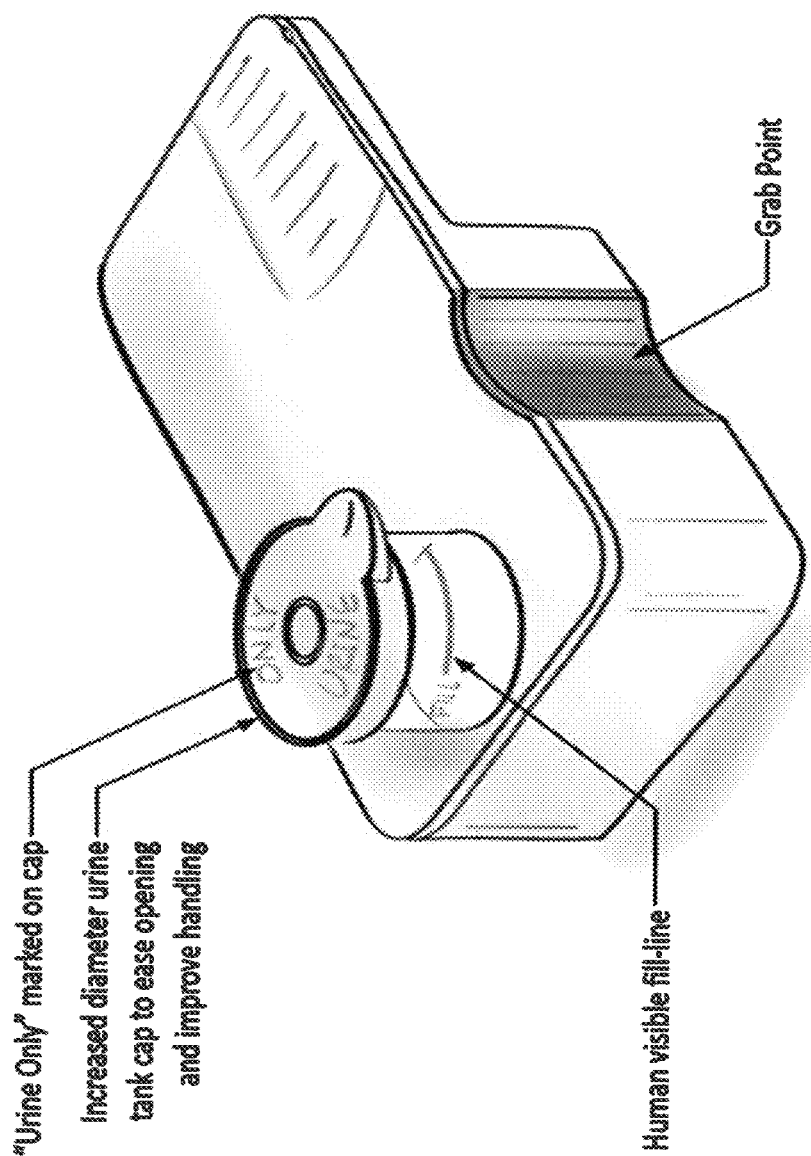
FIG. 29 demonstrates a cartridge concept with human factors considerations.

An alternative view of a non-limiting exemplary cartridge is provided in FIG. 29.

The sample tank allows a sample to be input. Samples may be fluid in nature, in which case the fluid may be poured into the sample tank prior to closing. The sample tank can include an attachment feature for securing the vented cap to the main cartridge body. This feature may comprise threads of various forms, tabs or bosses for a snap fit, compliant elements for a press-fit, ball detents, etc. The sample tank can contain a plurality of chambers, which can be cylindrical, square, rectangular or irregular in shape. These chambers may be sized to allow for overfilling (e.g., a chamber may be twice the expected sample input to allow for unintentional overfilling). The geometry of the sample tank can include a slope, ramp, taper, or other feature that allows clean drainage of patient sample through the check valve. The sample tank can include various pressure connections on the top, sides, or bottom of the tank. The sample tank can be sized to hold any desired volume of sample. In one embodiment, the sample tank can hold 0-100 mL of fluid. In another embodiment, the sample tank can hold 0-50 mL, 0-25 mL, 0-20 mL, 0-15 mL, 0-10 mL, 0-5 mL or 0-1 mL fluid.

In another embodiment, the sample tank allows for the input of a swab sample. Samples obtained via a swab or other device, including but not limited to a brush, scraper, spatula, or other similar devices known in the art may be placed into a buffer solution to allow transport of the sample material from the swab or other device into the buffer solution. In some embodiments, the swab buffer may be present in the sample tank, so that the swab or other device is placed in to the sample tank to allow transfer of the sample. The sample tank may be sized to hold any required volume of swab buffer, although usually a smaller volume of swab buffer will be used in comparison to a the total volume of a fluid sample. In one embodiment, the sample tank may hold 0-25 mL, 0-20 mL, 0-15 mL, 0-10 mL, 0-5 mL or 750 µL-1.5 mL of swab buffer. In other embodiments, the swab or other device may be placed into a swab buffer held in an external container, and following transfer the swab buffer can be placed into the sample tank.

Figure 8:
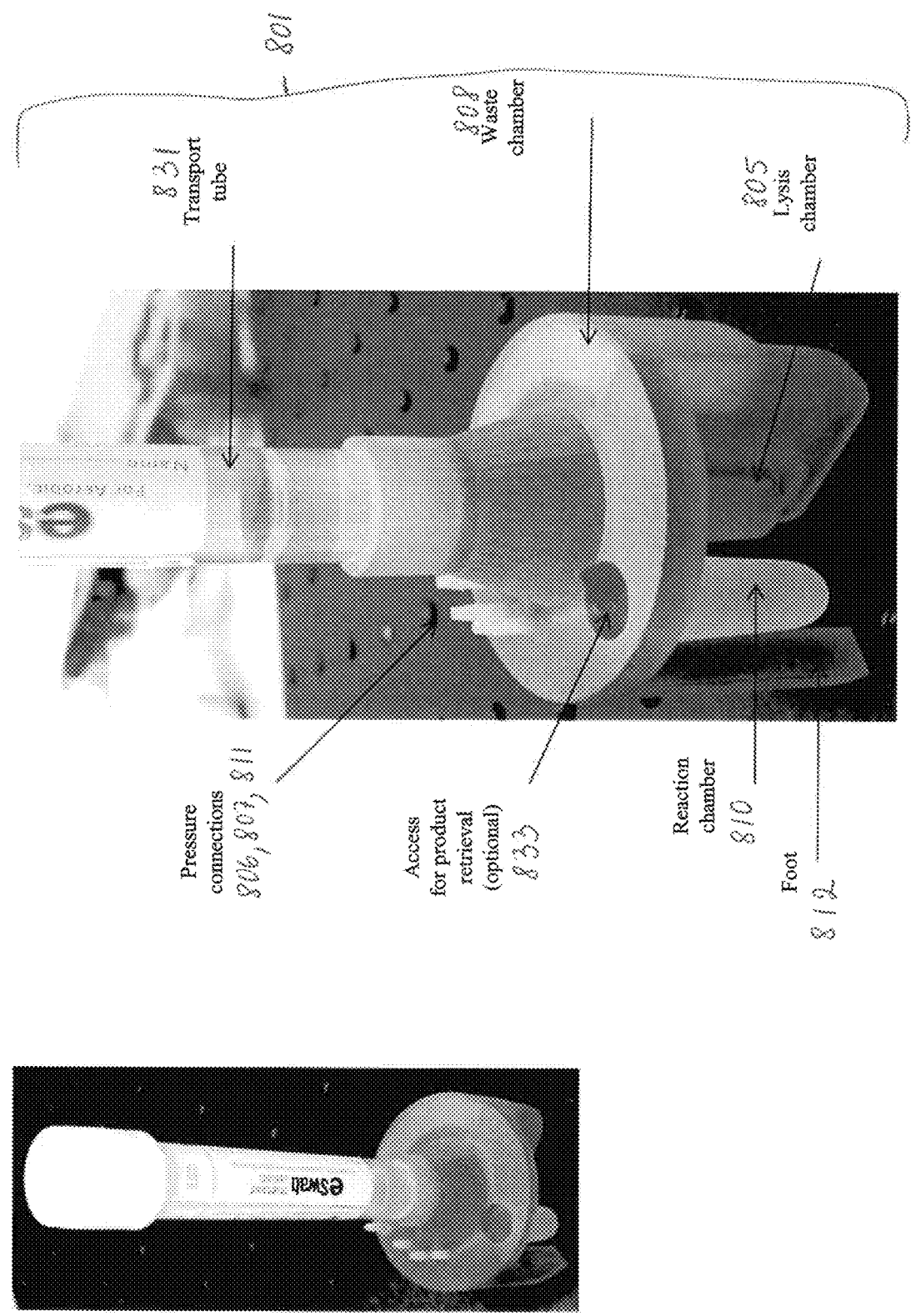
FIG. 8 demonstrates a sample transport tube directly seated in a cartridge according to one embodiment of the present invention.

In a further embodiment, the sample tank can be replaced by a configuration allowing direct connection of a sample or swab transport tube. In instances where a sample is obtained on a swab or similar device, traditional commercially available products often include a sample transport tube which may contain swab buffer, into which the swab or other device can be placed. The cartridge can be designed to directly accept a swab transport tube as a means to input the sample. As shown in FIG. 8, the sample transport tube 831 is directly seated in cartridge 801, thereby eliminating a manual step of transferring the sample from the tube to the cartridge. Connection of the sample transport tube 831 to the cartridge 801 will cause an opening in the sample transport tube 831, to allow the contents of the sample transport tube 831 to enter the cartridge 801. Cartridge 801 contains a filter (not shown) that allows filtration of the sample, with the waste products to be contained in the waste chamber 808. A lysis chamber 805 will hold the sample during lysis, before the sample is delivered to a reaction chamber 810. The sample will undergo a reaction, for instance an amplification reaction in reaction chamber 810, with the reaction results measured either simultaneous or subsequence to the reaction. For instance, measurement could be obtained by real-time PCR, end-point fluorescence, HRM, or other known detection methods. Pressure connections 806, 807, 811 allow for pneumatic control of the sample movement with the cartridge 801. Optionally, an access port 833 will allow retrieval of the sample from the reaction chamber 810. A foot 812 may be provided for stability of the cartridge 801.

The sample tank is closed by means of a cap, ensuring the sample is contained within. In some embodiments, the cap can be a vented cap. The vented cap can contain an attachment feature for affixing the cap to the main body of the cartridge. This feature can comprise threads of various forms, including fast start buttress threads, a variety of tabs or bosses for snap fits, compliant elements for a press fit, ball detents, etc. In one embodiment, a compliant element, such as an O-ring or gasket, can be included to seal the vented cap to the cartridge body. The vented cap can include grip features, such as knurls, wings, knobs, or handles to improve ease of use. The cap can include a vent, which can comprise a hole in the top, sides, or bottom of the vented cap. This hole can be covered by a filter, functioning to contain any contaminants and prevent them from escaping the cartridge, thereby providing a sealed cartridge. Inclusion of the vent in the cap allows pneumatics to be used to control the motion of fluids within the cartridge. In some embodiments, the vent is disposed on the side of the sample tank rather than in the cap. In some embodiments, the vent includes a filter designed to contain aerosols within the device, protecting the instrument's fluid handling system from risk of contamination.

In one embodiment, a cap seal O-ring fits into the threaded cap. When the cap is tightened to the cartridge, the cap seal O-ring compresses and provides a robust seal. O-rings are standardized sealing elements known in the art that are well-suited for disposable use.

A check-valve is inserted into the bottom of the sample tank between the sample tank and the lysis chamber. The check valve may contain fluid until a sufficient pressure is applied, opening the check valve. Accordingly, the inclusion of a check valve provides fluid containment within the sample tank, thereby preventing wetting of a filter element present in the lysis chamber. The fluid held back by the check valve can be a sample, or reagents in those configurations where a fluid inlet is present in the sample tank or where reagents are directly introduced into the sample tank. In instances where the sample tank is designed to accept a swab sample, the check valve will also prevent the swab sample from contacting the filter. In some embodiments, the check-valve may be used to hold back the sample in the sample tank, allowing for additional preprocessing (e.g., injecting fluid into the lysis chamber to pre-wet the filter) prior to the sample being moved through the check-valve into the lysis chamber by application of negative pressure in an amount below the check valve crack pressure amount. The check valve can contain a sealing feature, such as an O-ring or gasket, which makes a seal and prevents fluid from moving around the check valve. The cartridge can include one or more alignment features for positioning the check valve, such as a mounting flange, seating lip, or snap-fit feature.

The lysis chamber is positioned directly below the sample tank, separated by the check-valve as previously described. In one embodiment, the outside of the chamber can be tapered in order to promote a good fit between the chamber and the external heater with which the lysis chamber will come in contact with when placed in the device. External features including, but not limited to such a taper can also help ensure the correct positioning of the cartridge both within the device and with respect to an external heating element. Additional features, such as clamps or tabs, can be used to secure the lysis chamber to the external heating element. The lysis chamber can include a support feature for the outlet channel, such as a flange or web. This flange can be minimized in size to minimize heat disturbance and maximize the area available for heat transfer. In some embodiments, the lysis chamber can feature metal inserts to enhance the heat transfer to the lysis liquid. The lysis chamber can be appropriately sized for any desired volume of sample and reagents, but can typically be smaller than the initial sample tank. For example, the total volume of the lysis chamber can be 0-50 mL, 0-25 mL, 0-20 mL, 0-15 mL, 0-10 mL, 0-5 mL, 0-1 mL, 0-800 µL, 0-750 µL, 0-600 µL, 0-500 µL, 0-400 µL, 0-300 µL, 0-200 µL, or 0-100 µL. In one embodiment, the total volume can be approximately 600 µL, which allows for up to 400 µL of lysis reagent, plus additional buffer space to prevent fluid from entering any upstream channels, assuming the total volume of sample remaining in the lysis chamber is less than 200 µL.

The lysis chamber can include a filter assembly mounted to the bottom of the chamber. This filter assembly can comprise a number of components, including the capture filter, support features such as nylon or steel mesh, and sealing elements such as gaskets or O-rings. One or more outlet channels can connect to the lysis chamber, and can function to remove any liquids from the chamber and transport them to downstream processes. A plurality of inlet channels can connect to the lysis chamber and can serve a variety of functions, including reagent injection, pressure sensing, and venting of gas to atmosphere.

The filter assembly includes a capture filter designed to enrich targets of interest from a sample, including but not limited to microorganisms. The capture filter is used to isolate microorganisms that may be present in the sample by allowing the fluid components of the sample to pass through while capturing the microorganisms present. One of skill in the art will be able to appropriately select a filter size and composition based on the size of the microorganisms or other targets desired to be captured. The capture filter can be cut to a desired shape and placed at the bottom of the lysis chamber. For instance, one of skill in the art could utilize a filter material such as that found in the GE Healthcare Fusion V filter.

In another embodiment of the present disclosure, a gradient pore size depth filter can be used as the capture filter. One typical method for concentrating microorganisms, for example, a microorganism such as *Trichomonas vaginalis* (averaging 7-10 µm in size), is by filtering the organism using a pore size smaller than the target organism to ensure capture (<7 µm). Pre-filter(s) can also be used. Pre-filter(s) have a larger pore size and are placed before a smaller pore sized filter. The larger pore size filter can filter out the larger impurities in a sample and the smaller pore size is used to capture the organism of interest. Pre-filter(s) placed before a smaller pore sized filter can be used to capture multiple target organisms of different sizes, as would be required in some multiplex assays.

In one embodiment of the present disclosure, a gradient pore size depth filter is used. The depth and gradient in combination can filter out larger impurities from a sample (for instance, urine and vaginal swabs) and also capture the smaller target of interest within the same filter. The depth of the filter (thickness) and gradient pore size allows for a reduction in clogging because the impurities are able to travel inside the filter through the larger pore sizes rather than become trapped at the surface of the filter. An increased thickness of the filter also provides more paths inside the filter for the impurities to travel, which will assist in reducing clogging. The gradient of pore sizes can separate the impurities from the target organisms so the location of the target organism within the filter will be known. This known location of interest in the filter can then be the focus for downstream analysis. In addition to reduction of clogging, use of such a depth gradient filter can also reduce the time it takes to filter a sample, as well as lowering the pressure differential needed to filter a sample.

Filters of the present disclosure can be made from any material known in the art, for example, the filter can be a hydrophilic material such as glass fiber mesh or plastic such as polyester, polypropylene, polysulfone, polyvinylpolypyrrolidone (PVP) or polyethylsulfone. In those embodiments using a depth gradient filter, the pore size gradient can range from 1:10 to 1:100 in ratio.

Figure 9:
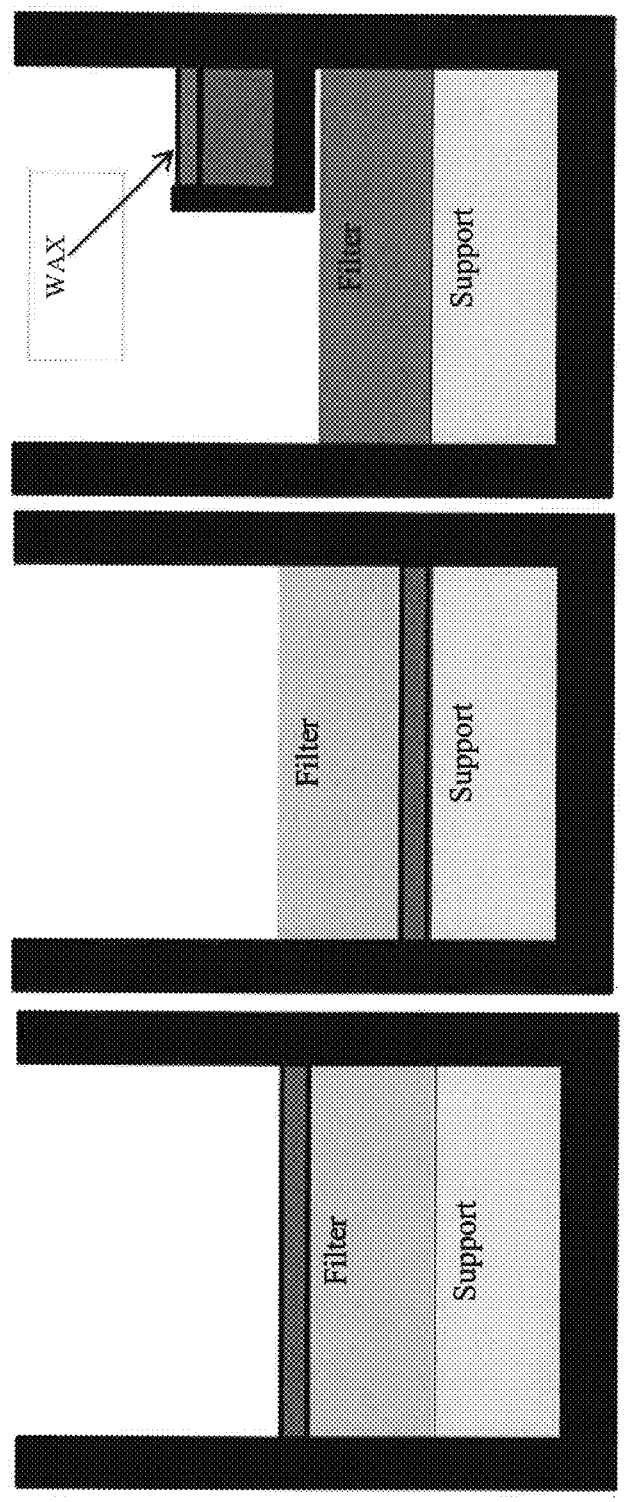
FIG. 9 demonstrates three examples of dry down lysis reagents placed in close proximity to a filter.

In another embodiment of the present disclosure, dried down reagents for cell lysis can be impregnated into the sample preparation filter (FIG. 9A), sandwiched between parts of the filtration assembly (FIG. 9B), or stored in a compartment in the lysis chamber and kept shielded from sample and washes by any technique known in the art, including a meltable wax (FIG. 9C). For instance, one option for lysis of the targets of interest includes chemical lysis, which can utilize reagents such as detergents and surfactants. Such reagents can be dried onto the filter itself, or could be dried separately and then placed on the filter, within the filtration assembly or elsewhere within the lysis chamber. Drying of the reagents can be accomplished by lyophilization or other processes known in the art.

The lysis chamber can additionally feature a fluid inlet and an external vent. The inlet may be used to inject fluids (e.g., water, including from a blister pack, wash, or lysis reagents). Water, for example, may be injected to pre-wet the filter before it is used to filter the user sample. Liquid may also be injected to wash the filter after filtering the user sample. Liquid may further be injected to provide sufficient liquid for lysis and elution steps. Other fluids known in the art can be used in place of water, for example, a wash buffer, lysis buffer, elution buffer and the like. In one embodiment, the fluid inlet can connect to the top of the lysis chamber, so that fluids and reagents can be inserted without opening the check valve. Additionally, in some embodiments, the fluid inlet is above the height of the fluid in the lysis chamber, so no liquid can contaminate the inlet. In another embodiment, the fluid inlet can use a barb. During sample workflow, the vent can be controlled by a valve. The vent can be opened during heat lysis to allow expanding gas to escape, or closed to allow negative pressure accumulation. In one embodiment, the lysis chamber vent ends in a barb, which can be mated to tubing for testing purposes.

Pre-wetting the capture filter with a benign liquid (e.g., DI water) allows the fibers of the filter to be pre-filled, preventing the absorption of crude sample and any inhibitory substances found in the sample. Following pre-wetting, the sample can be filtered (and targets concentrated) as desired. The ability to pre-wet the filter in the cartridge described herein relies on the ability to hold a sample back in the sample tank until such time as pre-wetting has been carried out, and the sample can be released into the lysis chamber that contains the capture filter.

In one embodiment, any means known in the art to prevent movement of a liquid sample can be used between the sample tank and the lysis chamber, including but not limited to, a capillary valve, meltable wax seal, a membrane filter, weir structure and a check valve, as described above. Depending on the method used to hold back the liquid sample, the cartridge can be configured to allow for the removal of release of the impediment to liquid movement. For instance, a wax seal may require the application of heat to melt the seal and allow liquid to pass. A check valve, for instance as described herein, will hold the sample back until a specified 'crack' pressure is applied. This allows the system to control when the sample is released with simple pressure control. Several configurations of the check-valve exist and are compatible with the spirit and scope of this disclosure.

Release of the benign liquid onto the sample can be by injection of the liquid through a port, integration of a liquid filled blister pack which is crushed or pierced to release its contents, and other similar means. In some embodiments, the pre-wetting liquid can be a low surface tension fluid. In another embodiment, the liquid can contain a surfactant. In a further embodiment, the liquid can contain an alcohol such as IPA. It is desirable that the pre-wetting liquid has minimal impact on the subsequent amplification or other reaction that will occur to the sample. In some embodiments, a surfactant typically used in amplification reactions such as PCR may be used in the pre-wetting step (e.g., Tween-20, Triton X, DSMO, etc.).

Although pre-wetting the filter can assist in enhancing the efficiency of the filtering process, clogging of the filter can be a concern. In particular, in some embodiments samples such as biological samples may be used that contain particulate matter such as red blood cells or bacteria, which can cause clogging of the filter. The present disclosure provides optional solutions that can be integrated into the methods, devices, and systems provided herein.

In one embodiment, there is a system and method for automated pre-wetting of a filter comprising providing a tank for holding a sample; holding the sample back, preventing it from wetting the filter, releasing a benign wetting fluid used to pre-wet said filter; and releasing said sample, allowing it to be filtered. Holding back the sample can be by means of a check-valve until application of a differential pressure greater than the crack pressure of a check-valve.

Figure 10:
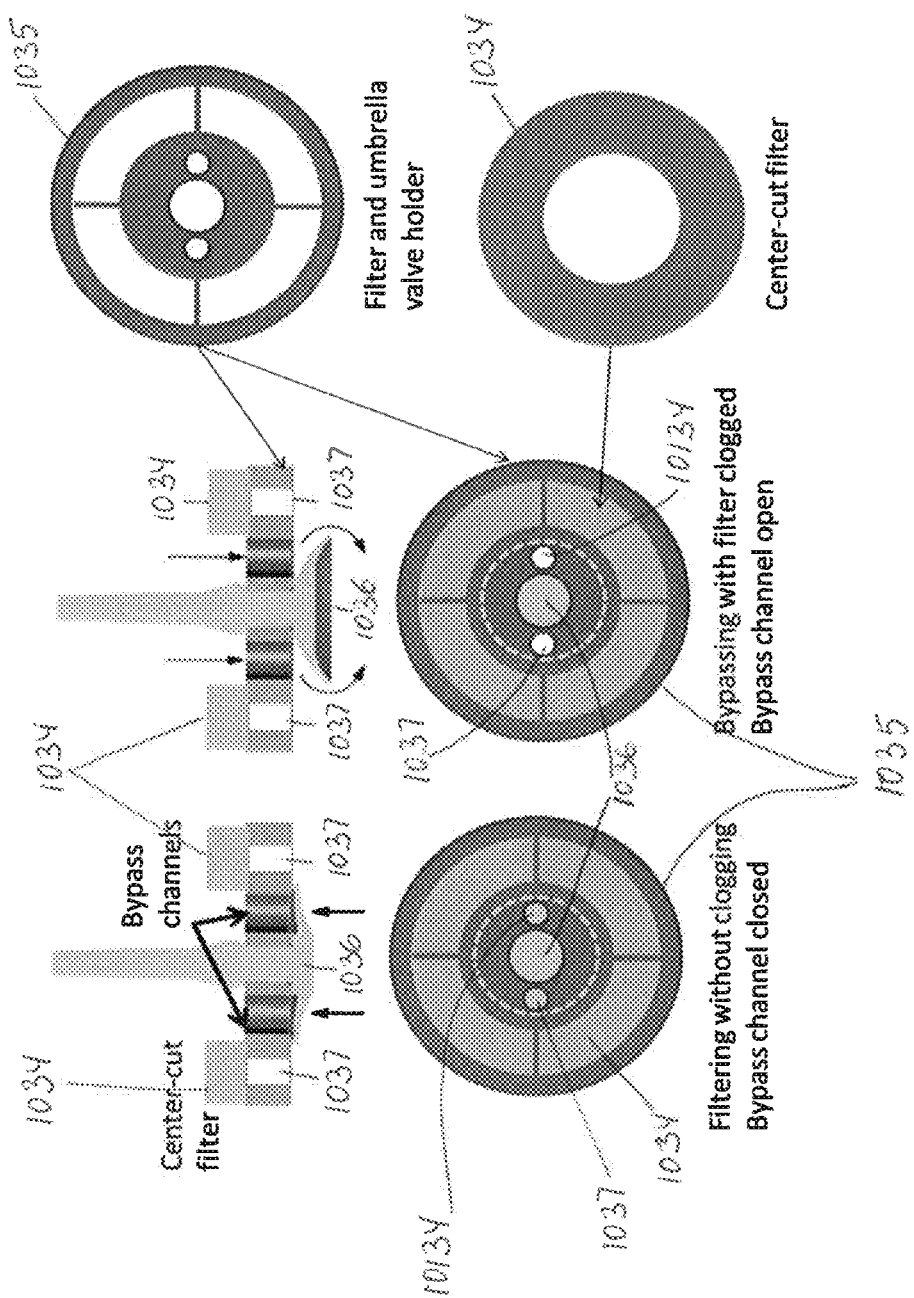
FIG. 10 demonstrates a clogging-free filter design according to one embodiment of the present invention.

In one embodiment, a clogging-free filter design is provided as shown in FIG. 10. FIG. 10 provides a filter and umbrella valve holder 1035 that has cut therein at least one bypass channel 1037 and at least one filtering channel 10134. The filter and umbrella valve holder 1035 additionally contains an umbrella valve 1036 having a sufficient diameter and being positioned such that the at least one bypass channel(s) 1037 and at least one filtering channel 10134 are normally closed by the umbrella valve 1036 during a low pressure filtering process and samples being filtered can pass through the center cut filter 1034. If the center cut filter 34 becomes clogged, a higher pressure can be applied to actuate the umbrella valve 1036 and open the bypass channel(s) 1037 and filtering channel(s) 10134. With the bypass channel(s) 1037 and filtering channel(s) 10134 open, unfiltered sample that has not been able to pass through the filter because of the clog can be drained through the bypass channel(s) 1037 and filtering channel(s) 10134, allowing downstream steps can proceed.

Figure 11B:
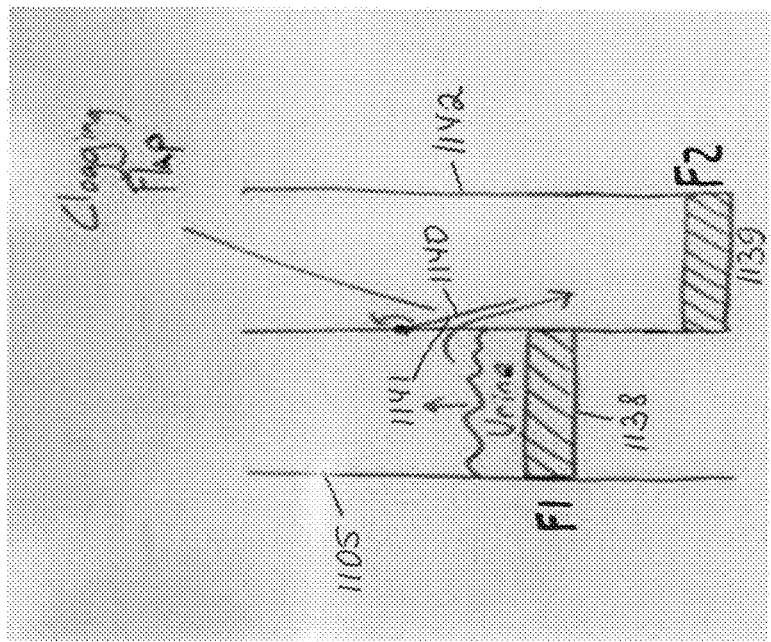
FIG. 11B demonstrates rotating filters according to another embodiment of the present invention.
Figure 11A:
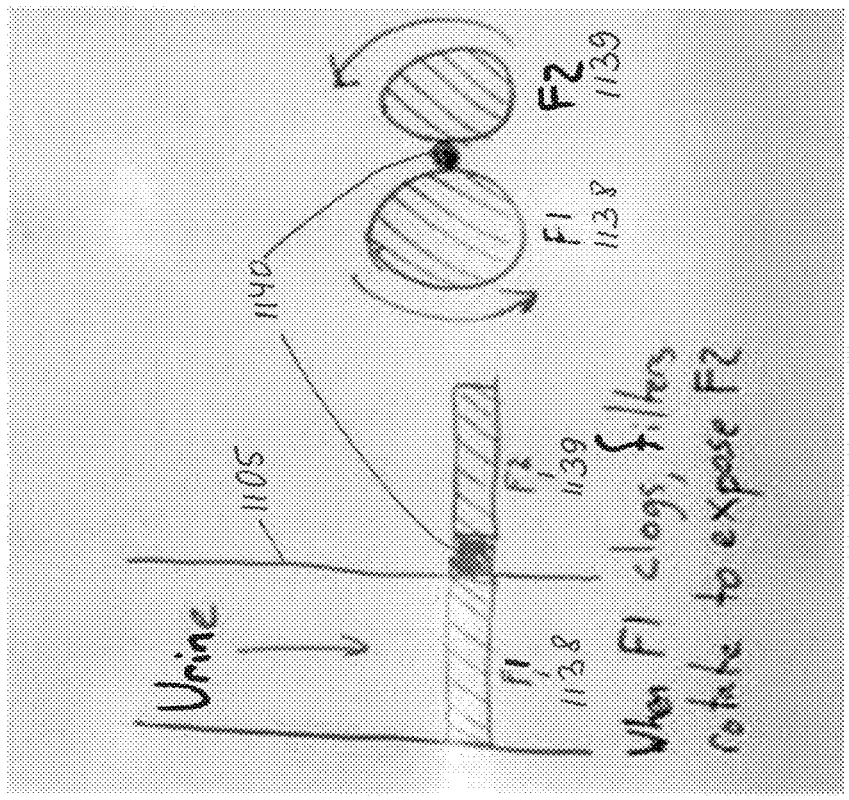
FIG. 11A demonstrates rotating filters according to one embodiment of the present invention.
Figure 11C:
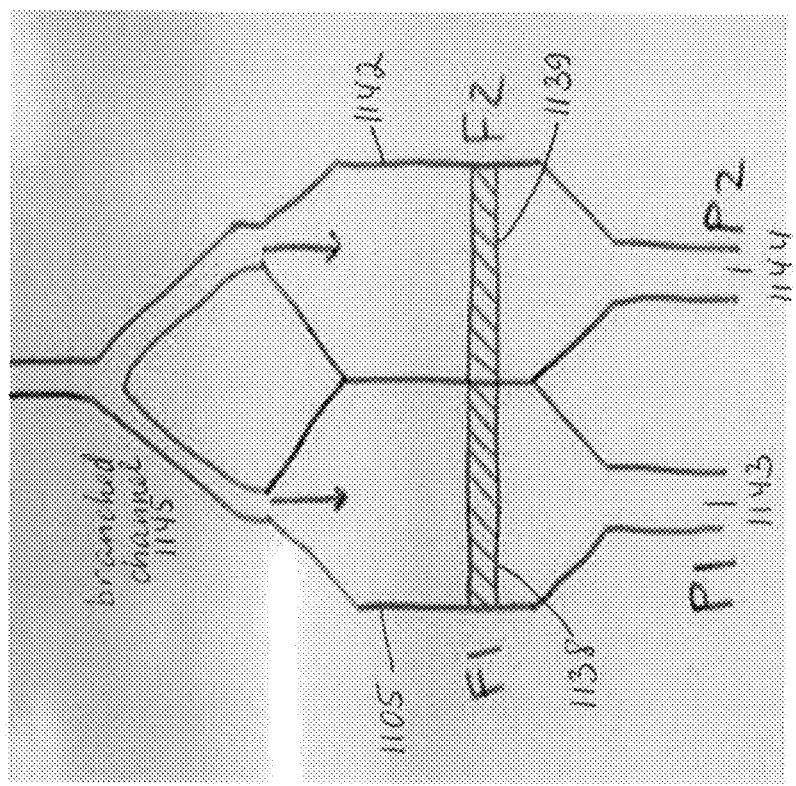
FIG. 11C demonstrates a filter having dual filter tubes.

In another embodiment, rotating filters as shown in FIG. 11A can be used. At least two filters 1138, 1139 are positioned on a filter mount 1140, which is rotatable within the lysis chamber 1105. In this manner, if the first filter 1138 become clogged, the instrument or a user can cause the filter to rotate out of the lysis chamber 1105 such that the second filter 1139 is rotated into the lysis chamber 1105. This results in a new, clean filter to be used for any further filtering of a sample.

In a further embodiment shown in FIG. 11B, the lysis chamber 1105 has two segments, the initial lysis chamber 1105 and an overflow tube 1142 with an opening 1141 between them, each segment of lysis chamber 1105 and overflow tube 1142 also containing a filter 1138, 1139. The lysis chamber 1105 and the overflow tube 1142 are fluidically connected by means of a clogging flap valve 1140 which in normal usage lies closed over the opening 1141 between the lysis chamber 1105 and the overflow tube 1142. However, should the first filter 1138 clog, such that fluid builds up on top of filter 1138 that is not able to pass through, the pressure from the fluid on the clogging flap 1140 will cause the flap to open, allowing the fluid to pass through opening 1141 and flow towards the second filter 1139 in the second segment of the lysis chamber 1105. One of skill in the art will be able to determine a desired height or volume of fluid which can build up in the lysis chamber 1105 prior to the opening of the flap valve 1140.

In another embodiment, the lysis chamber can be split into at least two portions 1105 and 1142 that are connected to a branched channel 1145. During initial sample filtering, an instrument pump can be connected to a first port P1 1143 and applies negative pressure to pull the sample through a first filter 1138 in the lysis chamber. If filter F1 experiences a clog, the instrument pump can be switched to begin to apply negative pressure to port P2 1144, thereby drawing any unfiltered sample into the second chamber 1139 and through the second filter 1139. First filter 1138 and second filter 1139 can be similar in construction in some embodiments. In other embodiments, filters 1138 and 1139 can be made of different materials or feature different pore structure to, for example, facilitate the capture of different target cells.

Figure 12A:
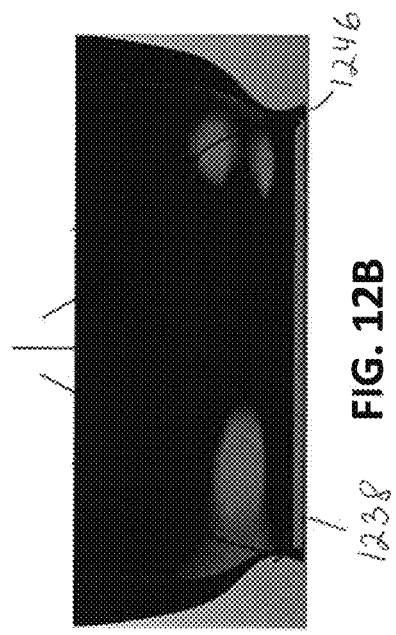
FIGS. 12A-B demonstrate a check valve designed to hold a filter of a desired size.
Figure 12B:
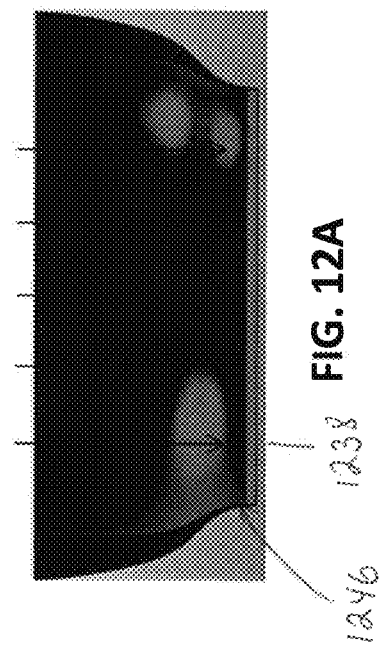

In a further embodiment, a check valve 1246 designed to fit around a filter 1238 of a desired size is provided in FIG. 12A-B. The check valve 1246 allows fluid to flow through the filter 1238 freely until a buildup of pressure below the filter 1238 (for example, from fluid flow rate or from clogging) deforms the surrounding boundary of the valve 1246, allowing fluid to bypass the filter 1238 from the edges. One of skill in the art will be aware that the material used and the geometric design of this valve 1246 will determine the crack pressure required to break the valve seal with the filter. FIG. 12A-B depicts that the filter 1238 can be placed on the bottom fitting of the check valve 1246, where it is typical that the wall thickness is much thinner when compared to the top portion of the valve. As provided herein, the deformation of this thin bottom section would provide a gap between the filter 1238 and the wall of the valve 1246 where fluid could flow around the filter 1238 after clogging.

Figure 13A:
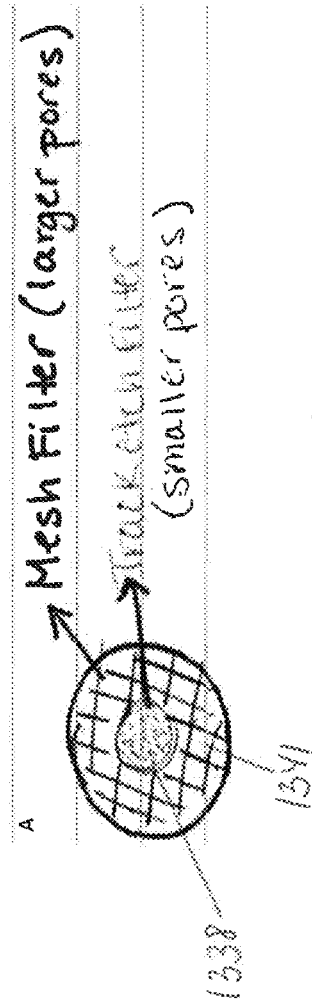
FIG. 13A Picture of the combination filter with the track etched membrane in the center and mesh filter surrounding it.
Figure 13B:
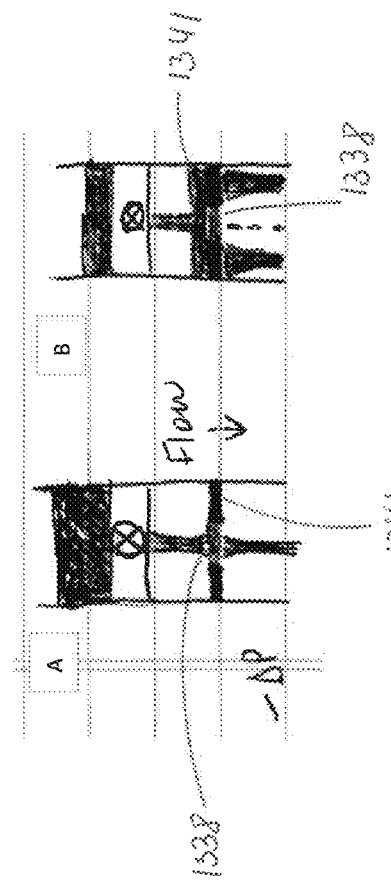
FIG. 13B demonstrates a filtering process. On the left, the sample initially flows through the center until clogged. On the right, once the center is clogged the mesh filters the remaining sample.

In a still further embodiment, there is provided the use of a combination filter. In this embodiment, two or more filters 1338, 1341 are provided in the same plane to capture particles of interest, wherein the filters 1338, 1341 are of at least two different types. For example, as seen in FIG. 13A, the filter 1338 is placed in the center of filter 1341. In one embodiment, a void may be made within filter 1341 to accommodate filter 1338. In one embodiment, the center filter 1338 can be a track etched membrane filter (e.g. polyester, polycarbonate, etc.). A filter of this type can have a defined pore size (e.g., 0.2 um) and the amount of pores within the filter is known (e.g., $3 \times 10^8$ pores/cm$^2$). The center filter 1338 can have a pore size that is small enough to capture a target of interest (e.g. a bacteria), but due to its small pore size this filter can clog because there may be other larger cells and debris in the sample. By surrounding the filter 1338 with a filter 1141, which can be of a different type, for instance a mesh filter (e.g., Fusion 5) that can have a range of pore sizes (eg. 2-11 um) which then allows more sample to pass through. In some embodiments, the sample flow can be controlled for instance by a valve and negative pressure, so that the sample first contacts the center of the combination filter 1338, so that the sample will be filtered using the smaller pore size capturing most of the target of interest from the sample that filters through (see FIG. 13B, left panel). It is understood that the center may clog, causing a slight buildup of sample above the combination filter. However, the second, outer filter 1341 would then be able to filter the remaining sample due to its larger pore size (see FIG. 13B, right panel). It will also still be able to capture some of the bacteria due to its pore size range (see FIG. 13B).

In a further embodiment of the present disclosure, the capture filter 521 can have filter seal O-rings 522 placed above and below the capture filter 521, such that a robust seal is created to ensure that no sample moves around the filter. In a further embodiment, the filter seal O-rings 522 can also provide support the filter material during filtration. Appropriately sized O-rings will be determined based on the size of the lysis chamber 505 in which the filter 521 is placed.

The lysis chamber 505 can also comprise an external vent 506 in one embodiment of the present disclosure. In one embodiment, during a sample workflow, this vent 506 will be controlled by a valve. The vent 506 can be opened during heat lysis to allow expanding gas to escape, or can be closed to allow negative pressure accumulation. In one embodiment, the external vent 506 can end in a barb, which can be directly mated to tubing for further testing.

In one embodiment, lysis chamber 505 serves a functional purpose of allowing lysis of any targets of interest that have been captured on the at least one filter. It is known that heat lysis is a rapid and effective way to lyse cells, in particular pathogenic micro-organisms of interest which can be targets of interest according to the present disclosure (for example, CT/NG/TV). In one embodiment, the cartridge and specifically the lysis chamber 505 can be subjected to Joule heating such that the sample is heated through simple thermal conduction. Thus, in one embodiment, the lysis chamber 505 is configured to closely mate with a heater within a device. As is known to those of skill in the art, temperatures as low as 60° C. can be effective. Thus, it is desired to rapidly introduce heat into the lysis chamber 505 for those applications when a heat lysis process is desired.

In some embodiments, a cartridge is in thermal communication with a temperature control system. The temperature control system can include a temperature sensor, a heater/cooler, and a temperature controller. In some embodiments, a temperature control system is interfaced with main controller so that main controller can control the temperature of the samples during biological reaction. Main controller can be connected to a display device for displaying a graphical user interface. Main controller can also be connected to user input devices, which allow a user to input data and commands into main controller.

A temperature control system can include a number of heating and/or cooling devices (e.g., a thermoelectric cooler (TEC), which is also known as a Peltier device, or other heating/cooling device), a number of temperature controllers, and a number of temperature sensors. Temperature control system can further include an infrared sensor for monitoring the temperature during amplification reaction and a source of electromagnetic radiation (e.g., a source of infrared, RF, Microwave, etc. radiation) for heating the reaction chamber. Lastly, temperature control system can include blower and/or heat sinks for cooling one or more of TEC.

In another embodiment, resistive temperature detectors (RTDs), a heater control and measurement circuit can drive RTDs with heater control signals transmitted to each RTD via an associated individual heater electrode, and sense a temperature of each RTDs. One or more heater elements can be associated with each reaction chamber.

At least one thermal generating unit, which is operable to provide heat to and/or absorb heat from at least a portion of the cartridge can be used as a thermal generating unit disclosed in U.S. Pat. No. 7,629,124 to Hasson et al., incorporated herein by reference.

In accordance with other aspects of the invention, the instrument includes a system to control the temperature inside the cartridge to effect rapid PCR cycling and to perform analysis on the PCR products. According to a non-limiting embodiment, preferred systems and methods for temperature control can be configured, implemented, and/or used in association with systems, methods, and/or apparatus for determining and controlling the temperature of integrated resistive heater elements in fluidic devices, as described in application U.S. Application Publication No. 2011/0048547, entitled "Microfluidic Systems And Methods For Thermal Control," the disclosure of which is hereby incorporated by reference in its entirety.

In another embodiment, an exothermic reaction could be used to generate the heat for heat lysis. It is within the scope of this disclosure that such an exothermic reaction would lyse any targets of interest (for instance, cells) and release genetic material (for example, DNA) for further processing, including through amplification. In one embodiment, a suitable reaction would be calcium oxide and water, which can generate a temperature of 60° C. in less than 10 minutes. Use of such a reaction requires fewer active components and less electrical power. Further, the reaction used can be selected to be non-inhibitory to downstream reactions, such that it can be included directly into the lysate without clean-up. Alternatively, the exothermic reaction could be placed in close thermal proximity to the targets to be lysed (for example, heat conduction from a neighboring reaction chamber could be used.

In one embodiment of the present invention, the outlet of the lysis chamber can be fluidically connected to downstream components. The main channel connects the bottom of the lysis chamber, for instance, underneath the capture filter, to the waste chamber and reagent chamber(s) of the cartridge.

The waste chamber can be comprised of one or more chambers designed to contain excess fluid, including fluidic samples, for example urine, wash water, or lysate. The waste chamber can also be used to collect waste from any wash steps. The waste chamber(s) are fluidically connected to the lysis chamber, with the waste chambers' inlet, for example, following a Y-branch, T-branch, or other similar configuration off of the main channel. In some embodiments, the connection can be made by having the Y-branch backwards (at an acute angle with respect to the inlet side). During filtration, negative pressure can be applied through the waste chamber to pull a sample through the filter. The waste sample flows through the main channel and into the waste chamber via the waste inlet. In one embodiment, the waste inlet is located at the top of the waste chamber, to prevent waste from re-entering the main channel. The waste chamber can comprise an outlet, which can comprise a channel connected to the waste chamber, a filter for containing contaminants, and a pressure connection port. The waste outlet port can be used to apply negative pressure during filtration. In one embodiment, there can be several 90 degree turns configured between the waste outlet and inlet, which can break up the fluid stream and prevent waste from contaminating the outlet. The waste chamber outlet port's filter can additionally contain aerosols within the device. In order to prevent jetting/wicking of fluid, the waste chamber inlet and outlet can be offset from one another. The total volume of the waste chamber can be greater than the total volume of liquid in the cartridge, for example, the total possible volume of a liquid sample, pre-wetting fluid, wash fluid, and lysis fluid can be contained within the waste chamber. For example, in one non-limiting embodiment, the waste chamber can have a total volume of 0-150 mL, 0-100 mL, 0-75 mL, 0-50 mL, 0-25 mL, 0-10 mL, or 2-8 mL. The shape of the waste chamber can be square, circular, rectangular, or irregular as it best suits the cartridge components. The waste chamber can contain a dry powder disinfecting agent in order to neutralize infectious agents in the patient sample. The waste chamber can optionally contain an absorbent substance, such as a foam pad or dry powder, to dry the waste and prevent spills or leaks.

In a further embodiment, the cartridge includes reaction chambers that are fluidically connected to the lysis chamber via the main channel. The reaction chambers can include a fluid metering feature or aliquoter designed to meter or aliquot a desired amount of lysate into the reaction chambers. In one embodiment, the aliquoter can dispense volumes of fluid from 5-200 uL, from 10-100 uL, or from 20-40 uL. As the volume dispensed depends on the configuration and size of channels and cartridge, one of skill in the art can easily adjust dimensions in order to dispense a desired volume. Reaction chamber can be molded out of polypropylene to provide optical clarity and heat resistance, and can be designed specifically to provide a snug fit for the dry reagent bead. In another embodiment, reaction chamber(s) can be sealed to the cartridge body.

In one embodiment, the aliquoter includes pathways to deliver fluid to one or more reaction chambers, which can be mounted to the cartridge body in a variety of ways, or which can be molded together with the cartridge, including press-fit, adhesive or solvent bonding, for example. Any method of mounting known in the art could alternatively be used. Each reaction chamber can be used for a different diagnostic test, can run duplicates of the same test, or could be used to provide one chamber as a control. In one embodiment, the reaction chamber(s) can comprise a thin-walled conical tube, of a material suitable for thermocycling. In another embodiment, the reaction chamber(s) can be PCR tubes. With respect to FIG. 14A-D, the aliquoter can also include a splitting feature, comprising a fluidic connection from the lysis chamber, which can contain lysate, through the main channel 1412, wherein the main channel 1412 has a branching feature 1413 that splits the sample lysate into equal portions. In one embodiment, this split 1413 can be a T- or Y-branch, or any other similar configuration, and can include a valve. The aliquoter can include an inlet 1447 extending into the reaction chamber(s) 1410, for dispensing a metered volume of lysate into the reaction chamber(s) 1410. The aliquoter can also include one or more outlet(s) 1411, which can contain a hydrophobic material 1448, such as a membrane or filter to contain contaminants or aerosols, and which one or more outlet(s) 1411 can also comprise a pressure connection that functions as a valve and prevent the flow of lysate after a target volume has been achieved in the amplification vessel. In some embodiments, multiple reaction chambers will share a pressure connection or outlet 1411 via a branch connection such as a Y- or T-.

Figure 15:
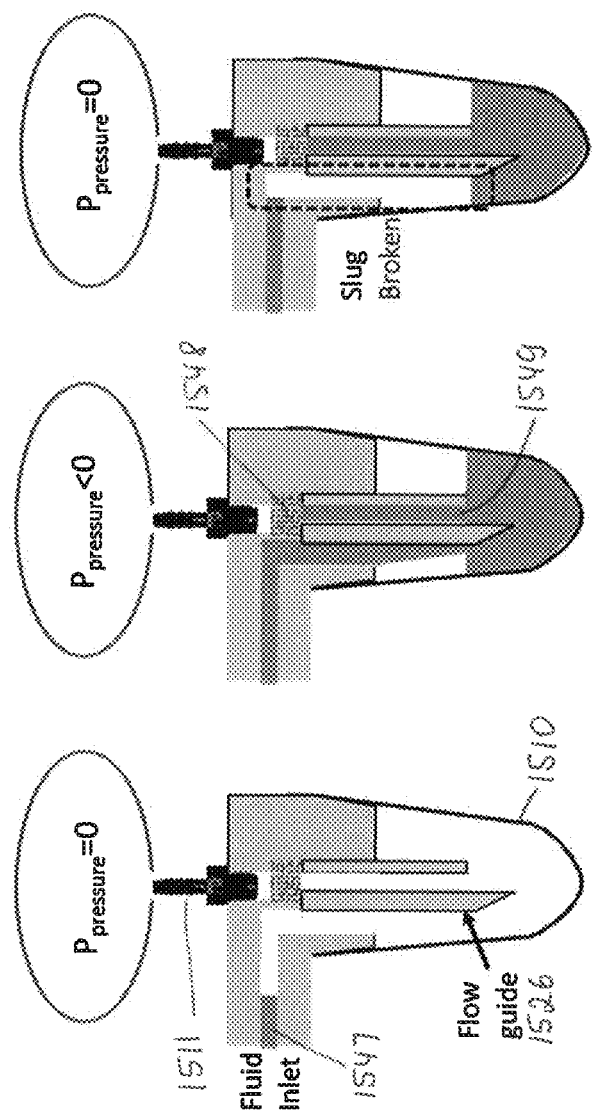
FIG. 15 demonstrates a method of precise liquid volume aliquoting according to one embodiment of the present invention.

With respect to FIG. 15, when negative pressure is applied to the pressure port 1511, a fluid is aspirated from an upstream supply chamber, for example the lysis chamber, through the inlet 1547 and the fluid starts to fill from the bottom of the reaction chamber 1510 guided by the flow guide (left panel). Once the fluid reaches the target level in the reaction chamber 1510 and then fills the central column 1549 leading to the gas permeable membrane filter 1548 (middle panel), the filter stops or significantly slows down the incoming flow. While the fluid is stopped or significantly slowed down, the "open" feature (as opposed to an "enclosed" channel or column) of the flow guide 1526 can break the incoming continuous slug and isolate the aliquoted reaction volume in the tube from the rest of the upstream supply slug (right panel). This passive slug breaking phenomenon is caused by the weight of the fluid hanging on the flow guide 1526 that outweighs the capillary force of the slug lowered by the open feature of the flow guide 1526. Therefore, the flow guide design in this invention can be one that lowers the capillary force of the slug significantly. For example, a semi-circular, flat or open rectangular shape is possible based on the desired capillary force.

In one embodiment, the slug breaking feature enables aliquoting of the desired volume required for the downstream reaction in the reaction chamber such as an amplification reaction, for instance, PCR. In another embodiment, the reaction can be executed fluidically isolated from the incoming supply slug. This fluidic isolation feature allows for the precise volume aliquoting and increases the reaction integrity since thermal cycling (as may be used in the downstream reaction) can create unintended flows between the reaction tube and the supply slug in the upstream main channel by thermal expansion and contraction of air inside the reaction tube.

Figure 16:
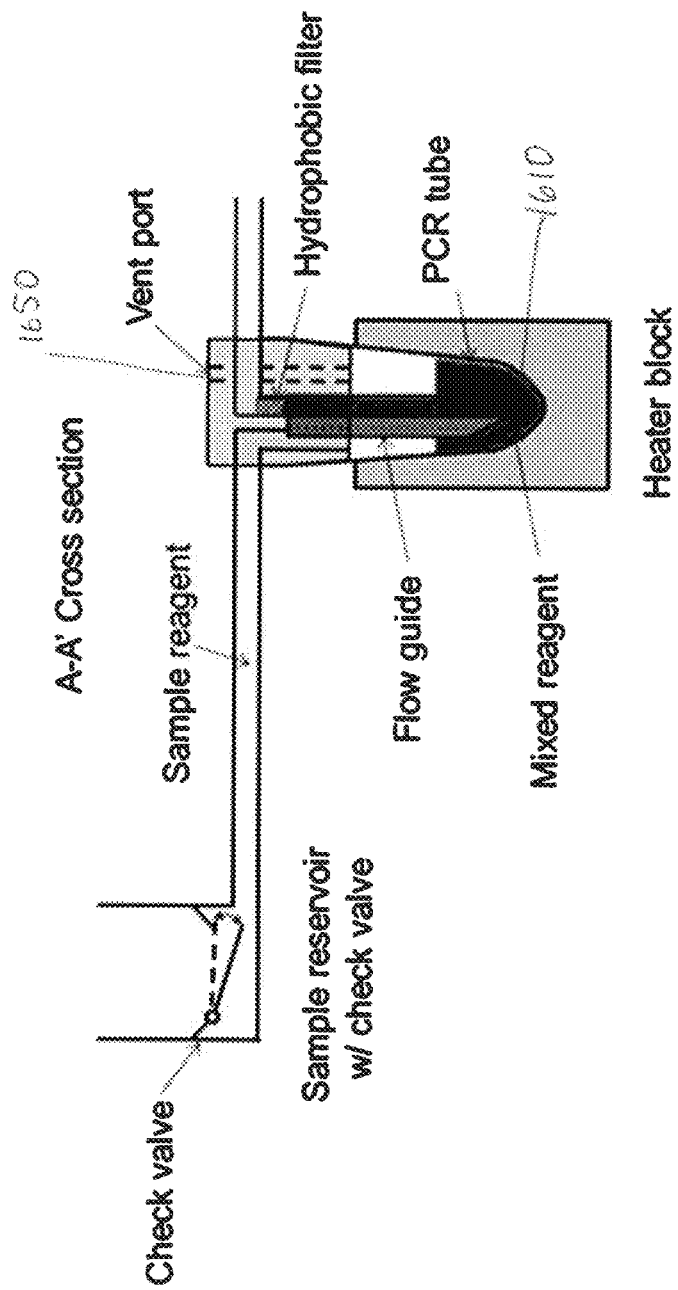
FIG. 16 demonstrates a method of precise liquid volume aliquoting using an active slug breaking according to one embodiment of the present invention.

In another embodiment, the fluidic isolation feature of the aliquoted volume can be further enhanced by having at least a second vent hole 1650 (as shown in FIG. 16) in the aliquoter design so that the remaining fluid on the inlet side after aliquoting can be cleared or pushed either back into the source chamber or into a waste chamber. This feature can be considered an active method of slug breaking in comparison to the passive method described above. In those embodiments where at least a second vent hole 1650, 1750 is used, the process shown in FIG. 17 can be used to provide active slug breaking. In the top panel, the reaction chamber 1710 has two vents, a first vent 1711 that is connected to a pump 1751 and a second vent 1750. Similarly, waste chamber 1708 has a waste outlet 1709 that is also connected to pump 1751. Both reaction chamber 1710 and waste chamber 1708 are connected by main channel 1712 by means of a T-junction, Y-junction or other similar feature 1713 to lysis chamber 1705. When vent 1750 is closed, and waste outlet 1709 is closed, pump 1751 applies negative pressure to reaction chamber outlet 1711, pulling fluid through the main channel, along the flow guide and into the reaction chamber 1710. Once the fluid makes contact with the filter in reaction chamber outlet 1711, the fluid flow is stopped.

Figure 17:
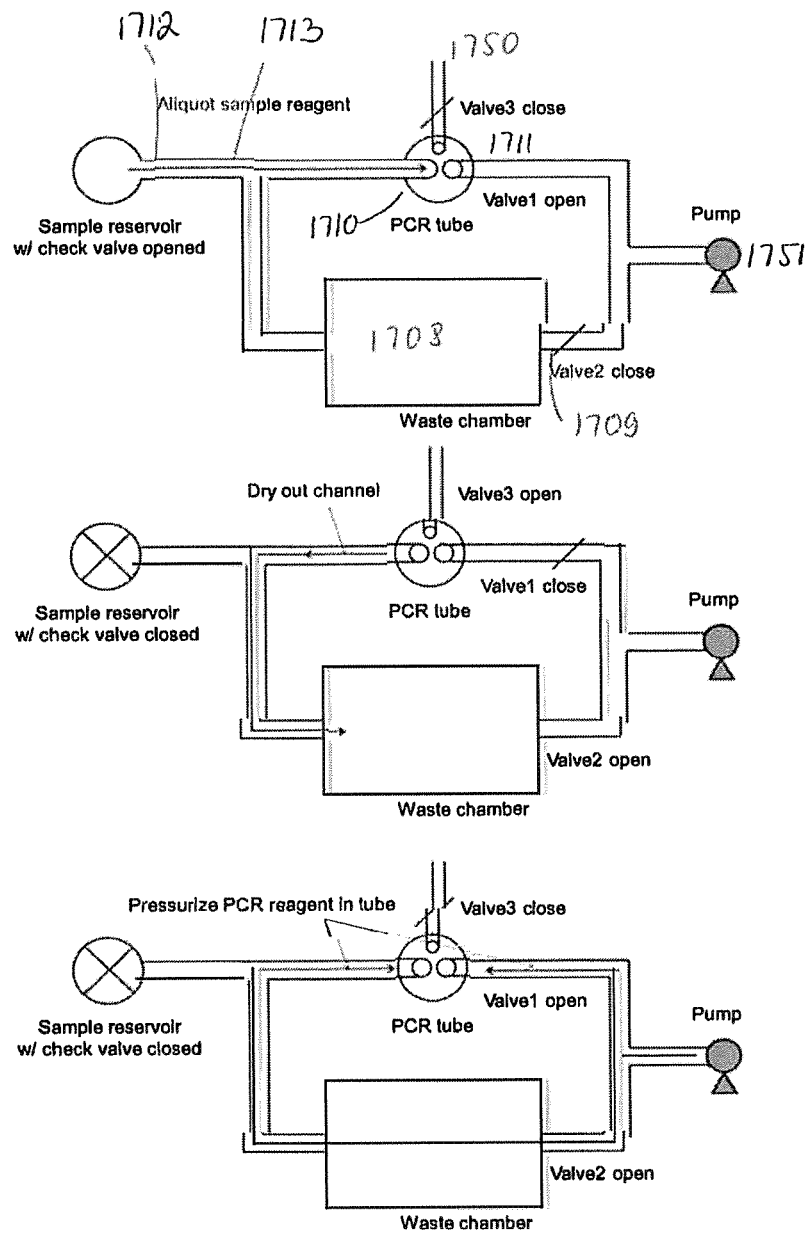
FIG. 17 demonstrates a method of precise liquid volume aliquoting using an active slug breaking according to another embodiment of the present invention.

In the middle panel of FIG. 17, the second reaction chamber vent 1750 is depicted as being opened to atmospheric pressure to create a pressure-driven flow from the reaction chamber inlet to waste chamber 1708 while the pump 1751 applies a negative pressure to waste chamber 1708 by through waste chamber outlet 1709. This dries out the channels leading to reaction chamber in order to prevent any fluid from leaking back into the channel during any necessary thermal cycles. In one embodiment, the negative pressure applied to the waste chamber needs to be low enough to keep a valve at reaction chamber outlet 1711 closed.

In the bottom panel of FIG. 17, reaction chamber outlet 1711 and waste chamber outlet 1709 are opened while pump 1751 builds a positive pressure in the entire channel network of the cartridge including the reaction chamber(s) 1710. The positive pressure built inside the cartridge suppresses the evaporation of reagents in the reaction channel(s) 1710 by increasing the fluids' boiling temperature. This can provide evaporation control during reactions, especially in locations where the boiling temperature of the reagents is lower than the hottest temperature the required by any reaction protocols. For instance, the water boiling temperature at the altitude of 2000 m is estimated to be 93° C. while the conventional denaturing temperature of PCR is 95° C. In one embodiment, the evaporation control would allow a user to run similar PCR protocols without boiling the reagents.

TABLE 1

Summarizes the pressures described in FIG. 19431-4.

|  | Pump | Valve 1 | Valve 2 | Valve 3 | Check Valve |
| --- | --- | --- | --- | --- | --- |
| (1) Aliquot | Neg P | Open | Close | Close | Open |
| (2) Dry out channel | Neg P | Close | Open | Open | Close |
| (3) Pressurize PCR reagent | Pos P | Open | Open | Close | Close |

Neg P: Negative Pressure
Pos P: Positive Pressure

In another embodiment, vent 1750 can be a pressure release port by opening it to atmospheric pressure throughout the reaction processes. In another embodiment, a groove can be made in the top sealing structure of the reaction chamber having one end is open to air space inside the PCR tube and the other end is connected to the vent port.

In a further embodiment, a passive method is provided to seal a reaction chamber and help mitigate evaporation, while still allowing expanding gas to escape the reaction chamber. The passive sealing method can make use of at least one small form-factor check valve called a duckbill valve. In one embodiment, one valve is placed upstream of the aliquoter and reaction volume, while another valve can be placed downstream of the reaction volume. Pressure can be applied from the pump and vent channel 411, causing both duckbill valves to open. Fluid enters the aliquoter and the correct volume is dispensed to the reaction chamber. Once the pump is turned off and pressure is no longer applied, the flow guide breaks the fluid stream and both duckbill valves close, sealing the reaction vessel.

During a reaction such as amplification, the air within the reaction chamber will expand and contract, exerting pressure on both duckbill valves. For the inlet valve, this pressure is applied in the reverse direction, so relatively large pressures can be applied before the seal is broken. On the outlet side, the duckbill valve can be selected to act as a vent above a certain pressure. Using this method, the pressure inside the reaction vessel could be controlled to below a predetermined value.

Figure 18:
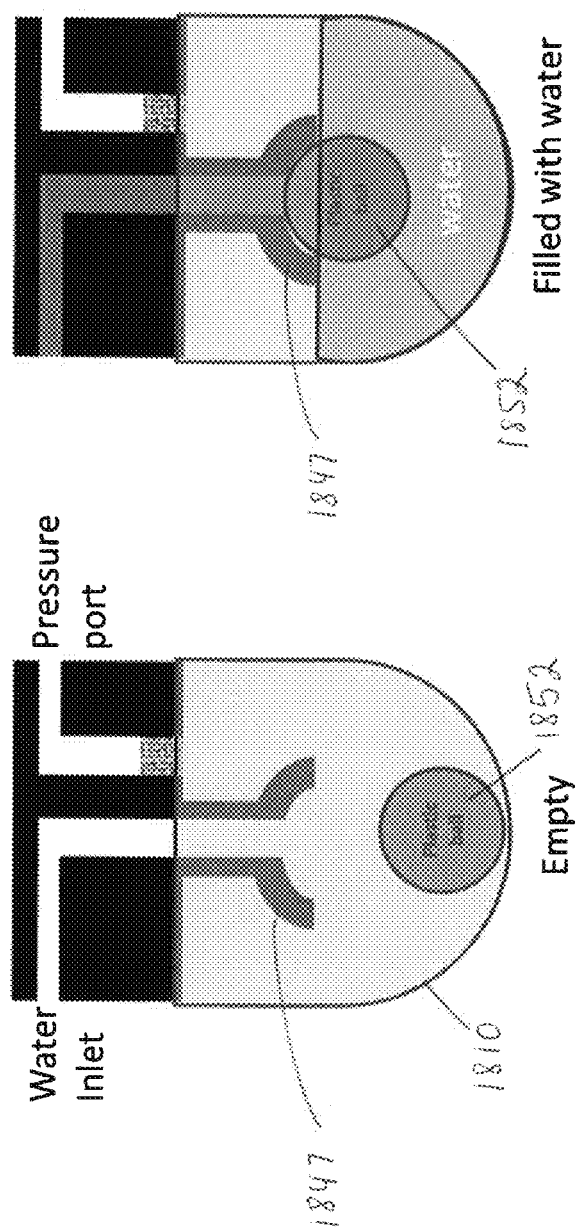
FIGS. 18A-B demonstrate a method of closing off the reaction chamber using a floating ball.

In another embodiment, as shown in FIG. 18A-B, a floating object 1852 can be placed in the reaction chamber 1810 that can float and close the reaction chamber inlet 1847 once the target volume is filled in the tube. In one embodiment, a spherical shaped floating object or floating ball 1852 can be used so that the floating object can close the reaction chamber inlet 1847 in any configuration once it floats to the target level as illustrated in FIG. 19431-6 for an example of fluid aliquoting. In one embodiment, the floating object 1852 can be any object that is lighter in its overall density than the incoming fluid. For example, a solid polypropylene ball can be used for fluid aliquoting. The floating object can be solid or hollow inside. The floating object physically breaks the fluid connection once the target volume is aliquoted and the seal is made. In another embodiment, this seal can be also used for the positive pressurization of reaction chamber during downstream reactions for the evaporation control.

Figure 19:
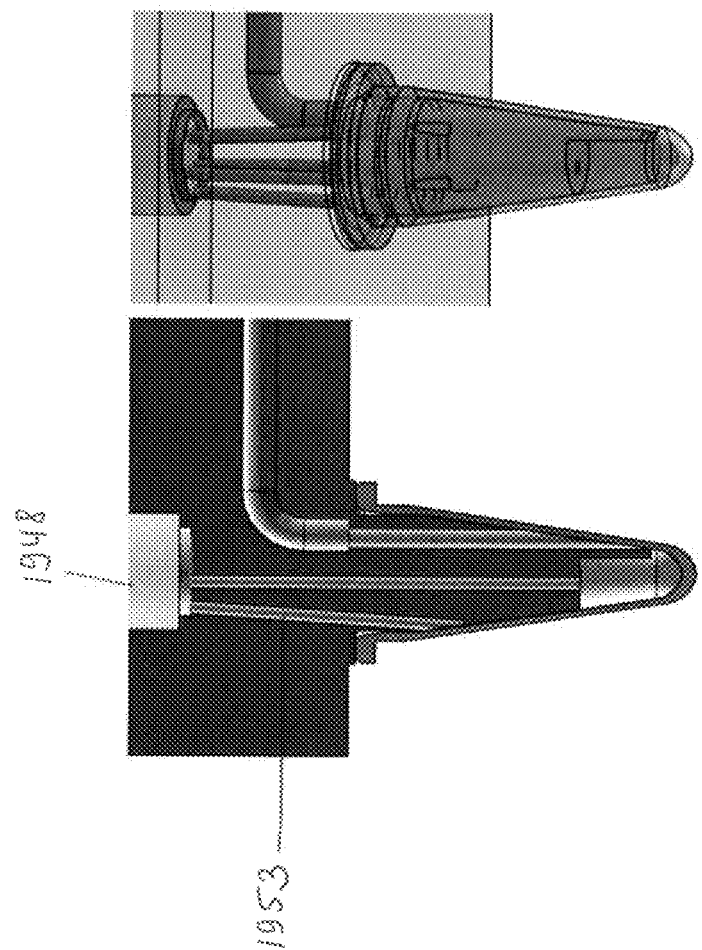
FIG. 19 shows an aliquoter design using a single filter and a vent flow control.

In a further embodiment, the aliquoter can be configured with a lower aspect ratio in such a way that the volume excluded by the feature in the reaction chamber is the target aliquoting volume that is filled with the incoming fluid. As provided in FIG. 19, additional vent channels 1953 can be provided at the top of the aliquoting feature, one end of which is directly interfaced with the hydrophobic filter 1948. The additional vent channels 1953 can remove air that would be trapped without the proposed channels. Usage of a single filter 1948 for aliquoting flow control (central column) as well as vent flow control (peripheral channels) allows for a simplified design.

Figure 20:
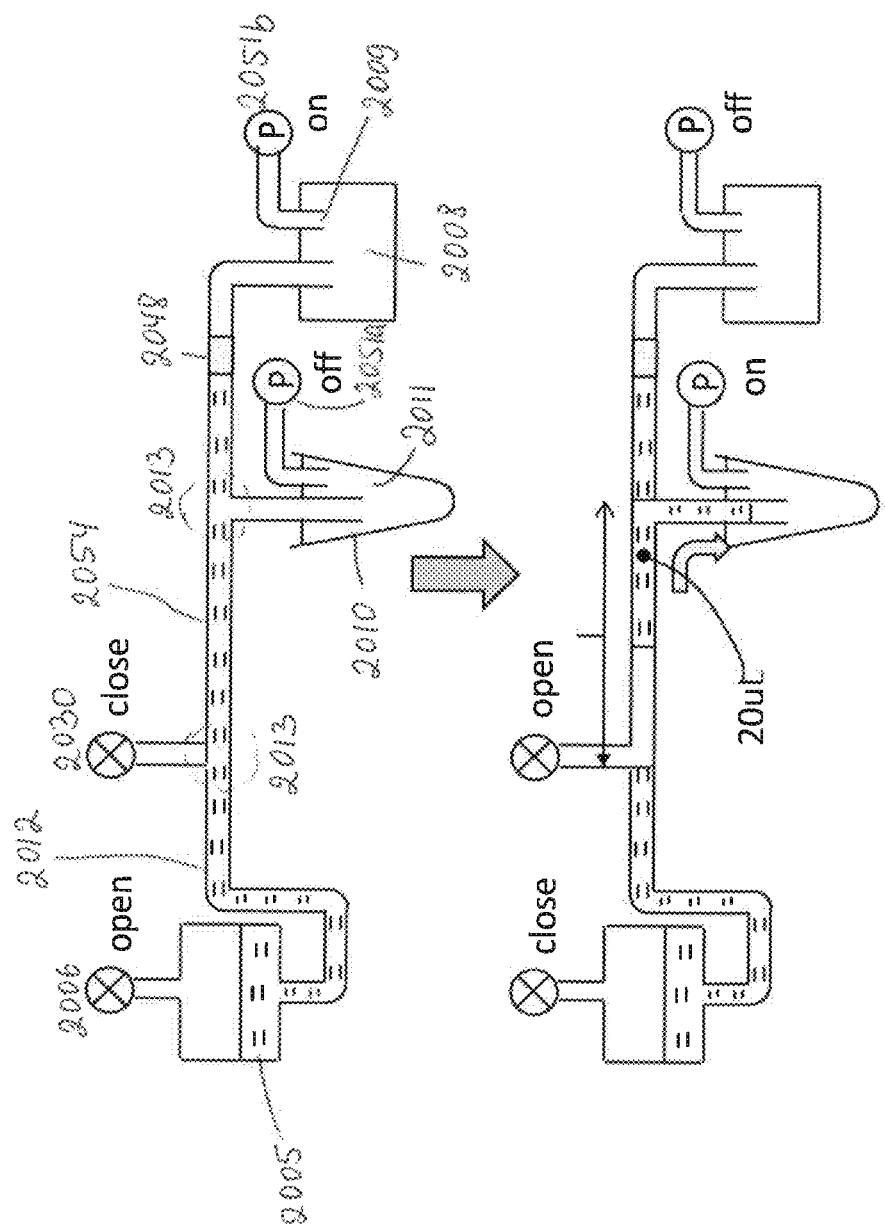
FIG. 20 demonstrates a channel aliquoting design in a biochemical reaction cartridge.

In another embodiment, a geometric aliquoting method can be used wherein a third branch channel is used to cut off a desired amount of fluid (for example, 20 uL) out of the main channel 2012. With reference to FIG. 20, forked channels 2013 (for instance, branching T- or Y-channels) are provided at the both ends of a main channel 2012, where the first branch channel of the first end connects to the lysis chamber 2005 and the lysis chamber external vent 2006, the second branch channel of the first end connects to a second valve 2030, the first branch of the second end connects to a reaction chamber 2010 and a reaction chamber vent 2011, which can be connected to a first pump 2051a, and the second branch of the second end connects to a hydrophobic filter 2048 and optionally a second pump 2051b. Alternatively, a single pump can be used such that the ports are used to switch the pressure.

Figure 21:
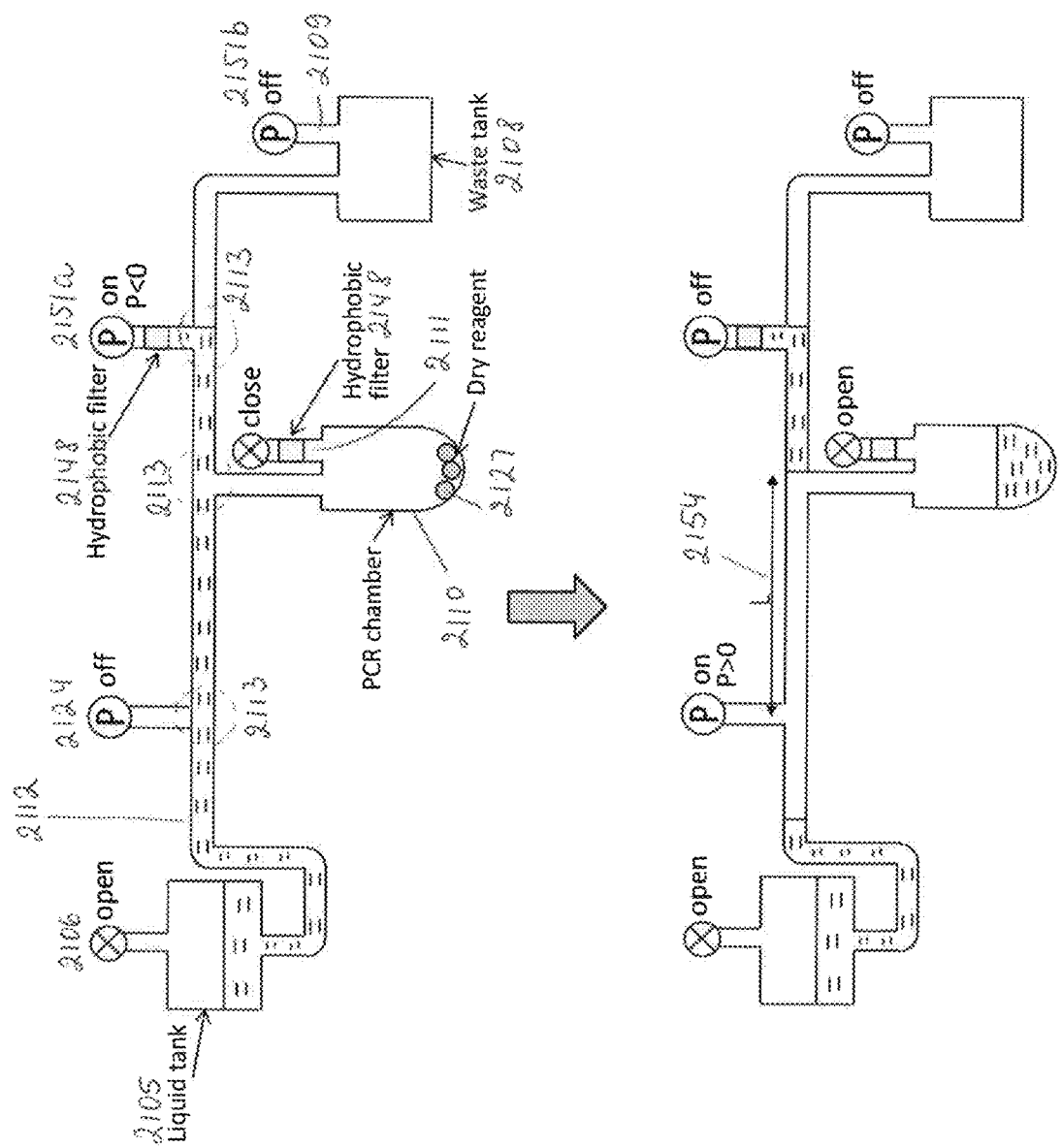
FIG. 21 demonstrates a channel aliquoting design using a waste tank positioned after PCR chamber to eliminate bubbles coming into aliquoting channel from the waste tank.

The aliquoting channel 2054 between the lysis chamber 2005 and the hydrophobic filter 2048 can be filled with the liquid by opening the first vent 2006, closing the second valve 2030, turning off the first pump 2051a, and turning on the second pump 2051b to negative pressure. Then the volume of the liquid decided by cross-sectional area of the aliquoting channel 2054 and distance between the ends flows into the reaction chamber 2008 by closing the first vent 2006, opening the second valve 2030, turning on the first pump 2051a to negative pressure, and turning off the second pump 2051b. In one non-limiting embodiment, the aliquoting channel 2054 size between two branches 2013 determines the aliquot volume, such that if the aliquoting channel has a diameter of approximately 1.5 mm and a length of approximately 11.3 mm in diameter, an aliquot volume of approximately 20 μL can be provided between two main channel branches 2013. In one embodiment, as shown in FIG. 21, the second valve 2130 can be a positive dispensing port 2124 that applies positive pressure to fluid in the metering or aliquoting channel, moving it into the reaction chamber while the reaction chamber pump 2115a is replaced by a valve. In some embodiments, the positive dispensing port uses a barb to connect with tubing for ease of connection. In one embodiment, the pump can be connected to a vacuum source. The hydrophobic filter 2148 acts as a cap once wet. Alternatively, a self-sealing filter can be used. In one embodiment, a positive pressure can be used on the vents/valves and the pumps can be replaced with vents to reduce leakage flow introduced from the lysis chamber 2105.

In a further embodiment, the positioning of the waste tank 2108 after reaction chamber 2110 as shown in FIG. 21 eliminates bubbles coming into aliquoting channel 2154 from the waste tank. In another embodiment, when using positive pressure to provide the fluid aliquot, the aliquoter is configured to allow opening the port 2106 of the lysis chamber 2105 instead of closing it as shown in FIG. 21. In another embodiment, the reaction chamber vent 2111 can have a hydrophobic filter 2148 to prevent liquid from flowing out from the vent 2111. During cartridge manufacturing, dry reagent beads 2127 can be put into the reaction chamber 2110 through the vent 2111 before inserting the hydrophobic filter 2148.

Figure 28:
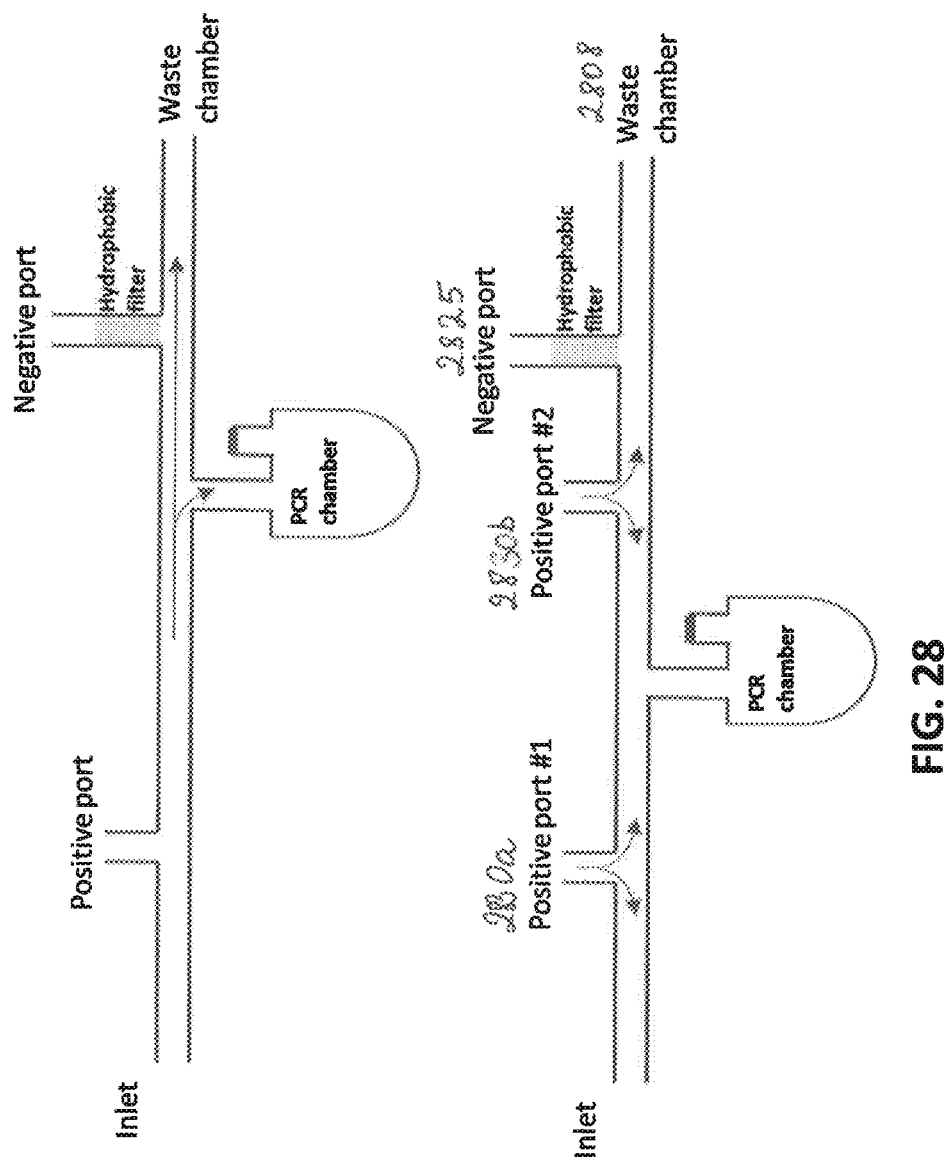
FIG. 28 shows an aliquoting configuration placing a negative pressure port between the PCR chamber and waste chamber with a single upstream positive pressure port.

In a further embodiment, an additional positive dispensing port 2830*b* can be added between the reaction chamber 2810 and the negative dispensing port 2825 as shown in FIG. 28. For the aliquoting, both positive ports 2830*a*, 2830*b* can have same positive pressure simultaneously so that the entire volume defined by the channel geometry by the two positive ports can be aliquoted into the reaction chamber 2810 without creating any outgoing partial flow towards the waste chamber 2808, providing no volume loss.

Figure 22:
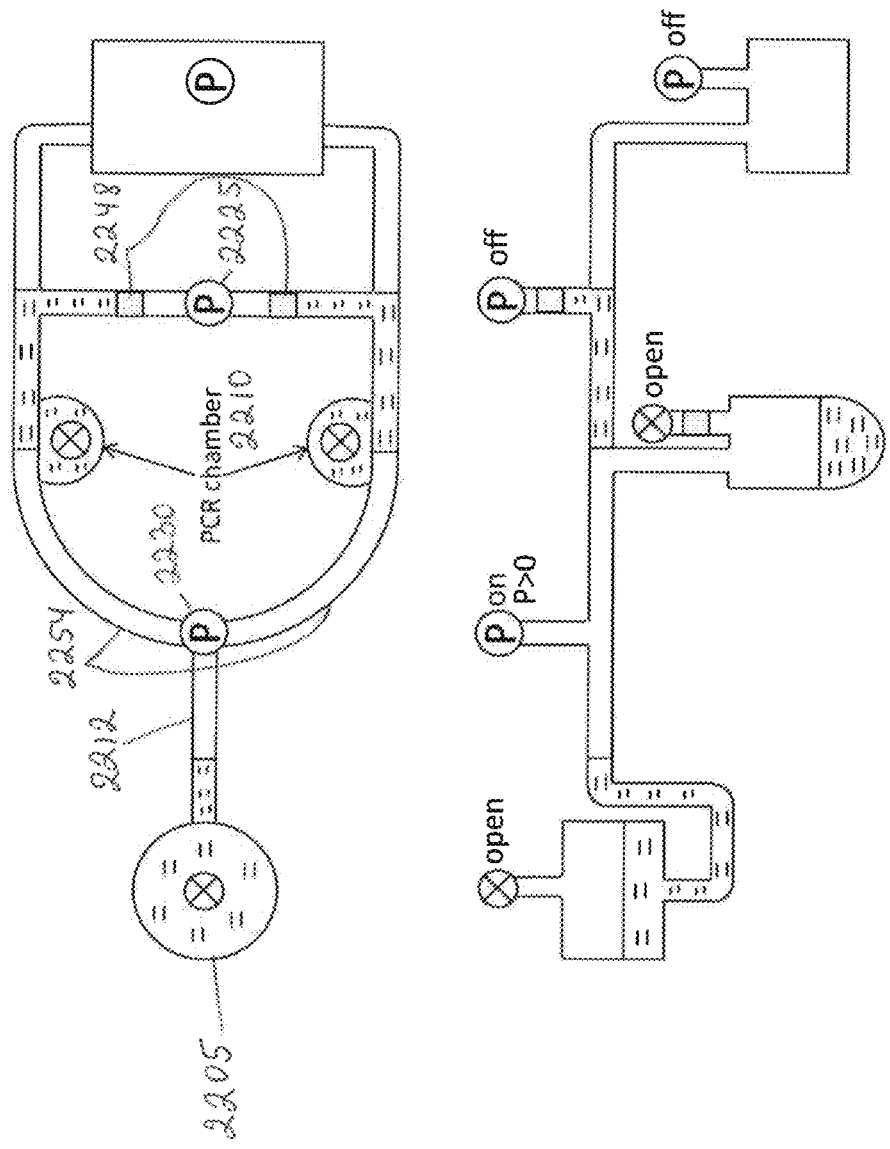
FIG. 22 shows an aliquoting configuration for two PCR chambers.
Figure 23:
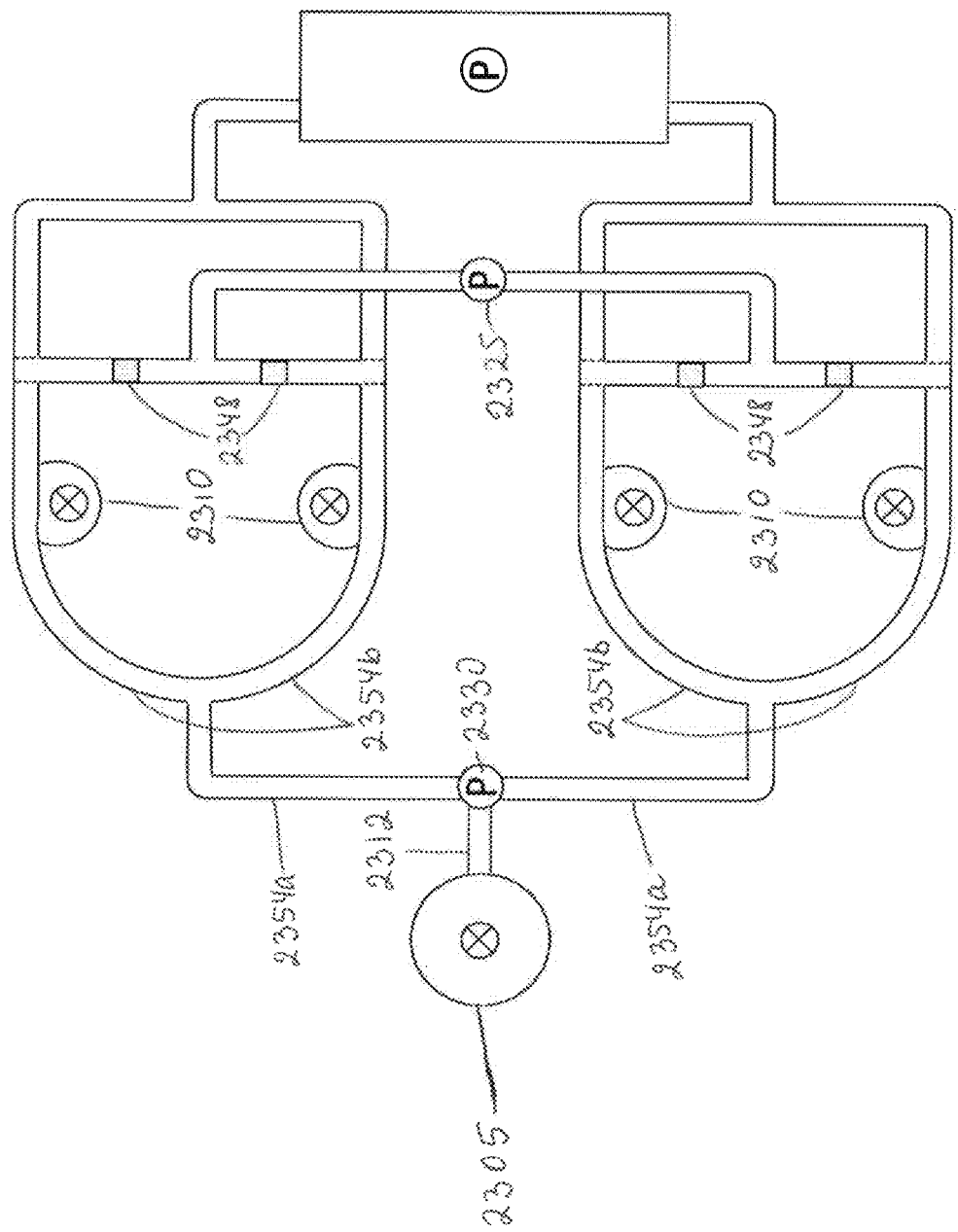
FIG. 23 shows an aliquoting configuration for four PCR chambers.

In yet a further embodiment, aliquoting can be performed into multiple reaction chambers 2210 simultaneously. FIG. 22 depicts the manner in which the aliquoting system depicted in FIG. 21 can be used for multiple reactions chambers 2210. The main channel 2212 from the lysis chamber 2205 is divided into two aliquoting 2254 channels, each of which is connected to one reaction chamber 2210. Each aliquoting channel 2254 has a hydrophobic filter 2248. Negative pressure through a negative metering port 2225 pulls fluid from the lysis chamber 2205 to fill the two aliquoting channels 2254 with the fluid at the same time. Then positive pressure is applied from one port 2230 and the predetermined volume of the liquid is dispensed into the two reaction chambers 2210 at the same time. The negative metering port can use a tubing barb for ease of connection. In a further embodiment, the aliquoter can be expanded to accommodate additional reaction chambers 2310 as shown in FIG. 23. The main channel 2312 from the lysis tank 2305 is divided into two channels 2354*a* and then each channel 2354*a* is divided into two channels 2354*b* again. Each of the four channels 2354*b* is connected to one reaction chamber 2310. Each channel 2354*b* has a hydrophobic filter and negative pressure through one negative metering port 2325 pulls fluid from the lysis chamber 2305 to fill the four aliquoting channels 2354*b* with the fluid at the same time. Then positive pressure is applied from one port 2330 and the predetermined volume of the liquid is dispensed into the four reaction chambers 2310 at the same time. It is within the scope of the present disclosure that any number of reaction chambers can be similarly filled at the same time, however scale up of the system may be easiest when scaling by a factor of two. In another embodiment, each of the aliquoting channels 2354 can be configured to dispense fluid directly from the lysis chamber 2305, instead of branching off the main channel 2312.

Figure 24:
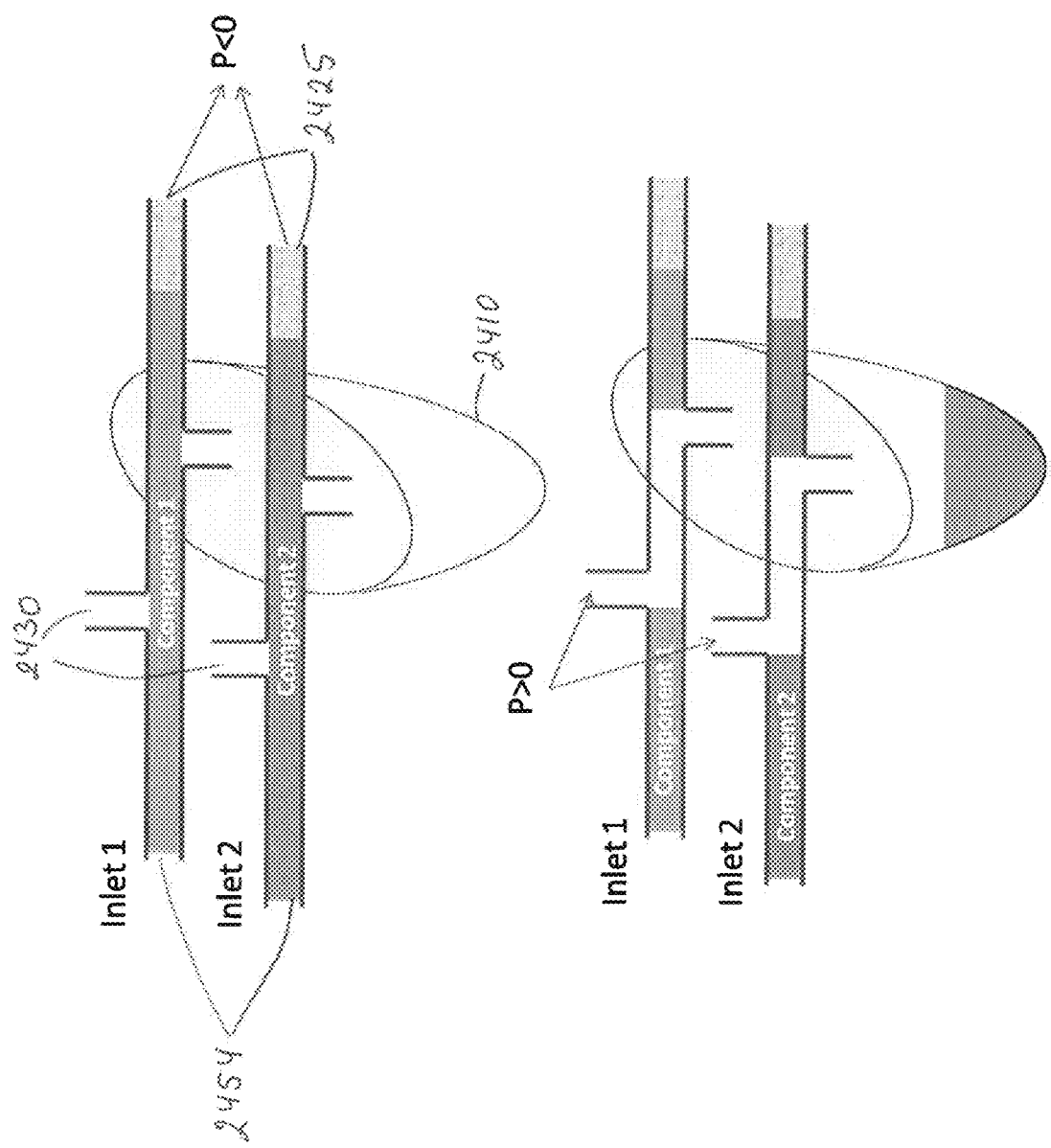
FIG. 24 shows multiple channel aliquoters connected to a single reaction chamber.

In another embodiment, multiple channel aliquoters can be configured to fill a single reaction chamber. In this manner, more than one liquid components can be precisely aliquoted and into a single reaction chamber as illustrated in FIG. 24. Aliquoter channels 2454 are filled with fluid when negative metering port 2425 applies negative pressure. Positive pressure can be applied from port 2430, depositing the volume in the reaction chamber 2410. In one embodiment, a predetermined volume of a sample can come from the first aliquoter and another predetermined volume of liquid reagents can come from the second aliquoter and they can be fused in the same reaction chamber 2410 for a downstream reaction. In one embodiment, the aliquoted volumes can be different for each component.

Figure 25:
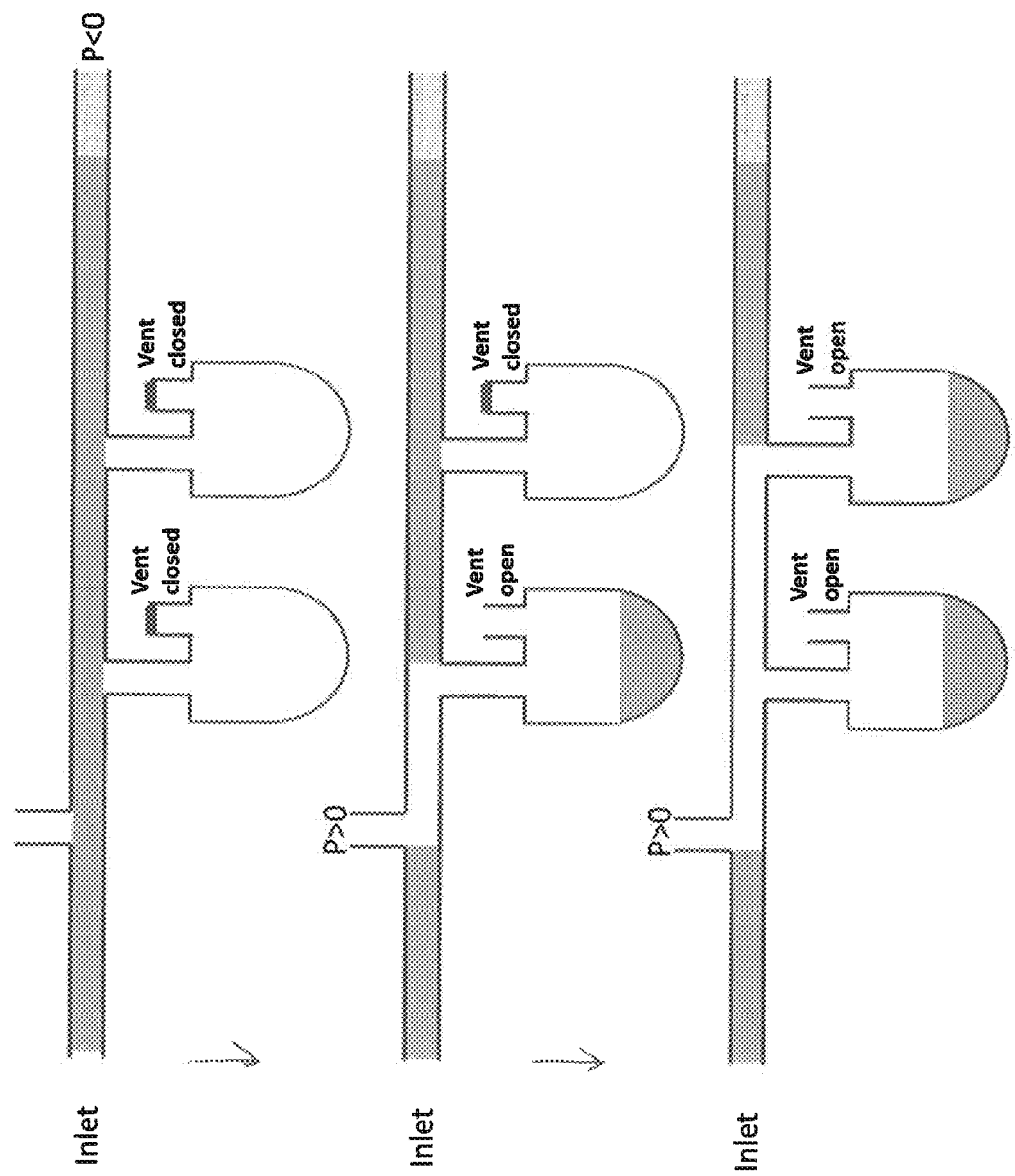
FIG. 25 demonstrates a method to break the main aliquot into two portions and store each in two different reaction chambers using a single fluidic channel.
Figure 26:
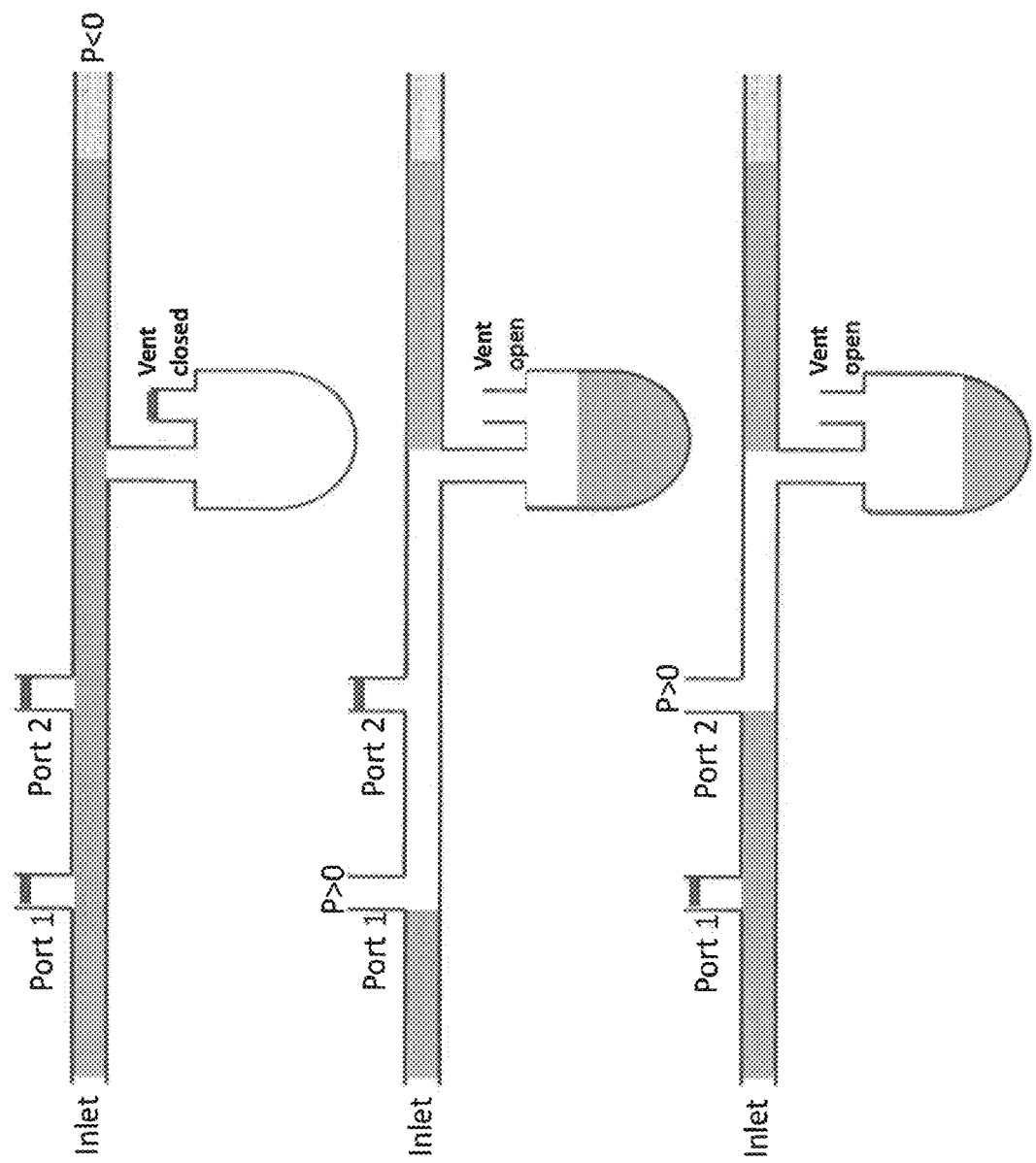
FIG. 26 shows a channel and multiple positive pressure ports connected to a single reaction chamber so that selected volume of fluid is aliquoted into the reaction chamber depending on the selected port.
Figure 27:
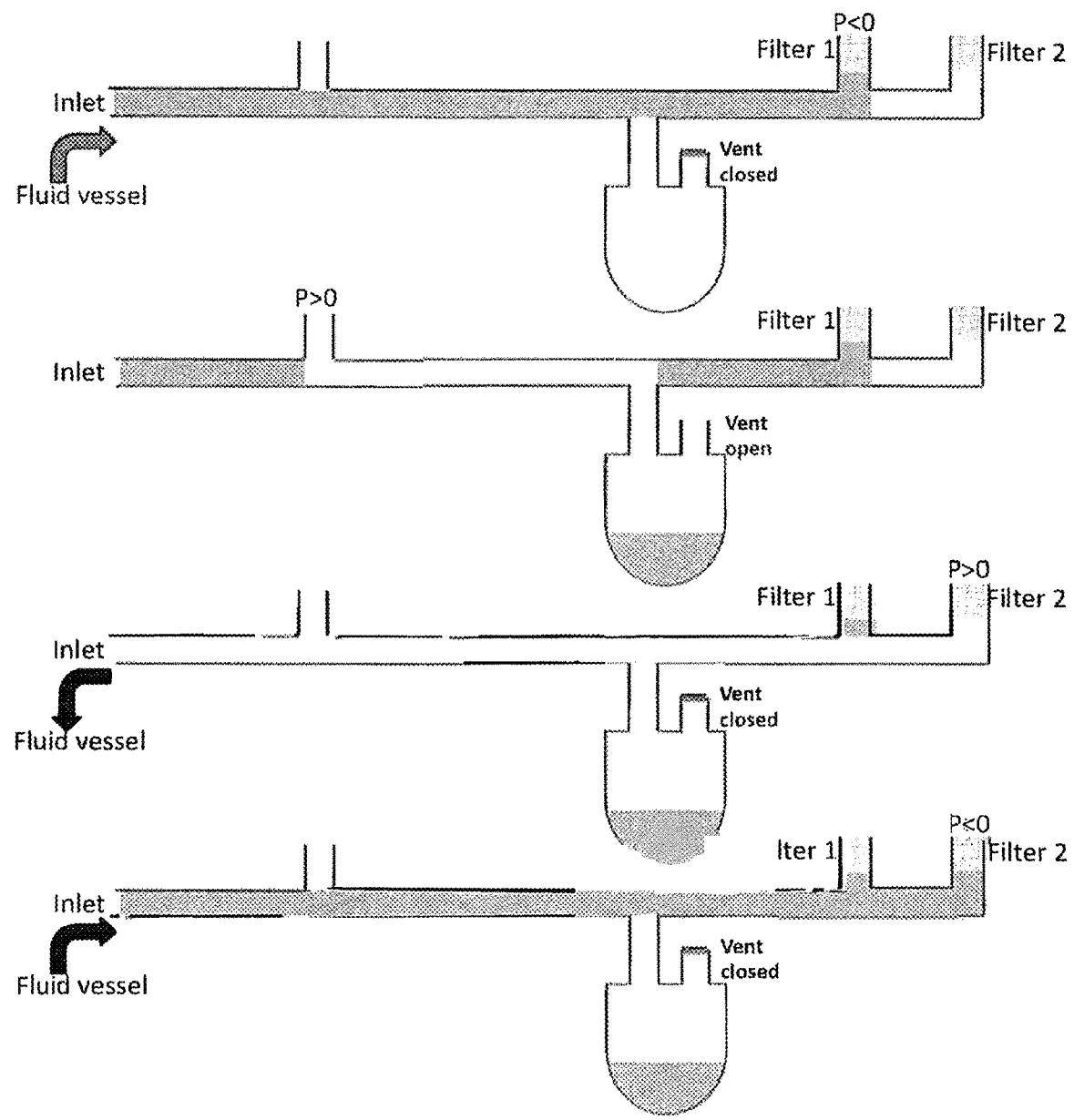
FIG. 27 shows a channel and multiple filtering ports with hydrophobic filter connected to a single reaction chamber.

In a further embodiment, liquid can be aliquoted into multiple reaction chambers as illustrated in FIG. 25. Using methods similar to those described above with respect to breaking the liquid slug, FIG. 25 demonstrates a method to break the main aliquot into two portions and store each in two different reaction chambers using a single fluidic channel. It is within the scope of this disclosure that aliquots could be broken into more than two separate portions. In another embodiment, as shown in FIG. 26, a channel and multiple positive ports are provided connected to a single reaction chamber so that selected different volume of fluid is aliquoted into the reaction chamber depending on the selected port. In a still further embodiment, as shown in FIG. 27, a channel and multiple filtering ports with hydrophobic filter are connected to a single reaction chamber so that after the first filter is wet by the first aliquoting, the second aliquoting can be performed using the second filtering port with the second hydrophobic filter without drying the filter. After the first aliquoting, fluid in the channel is pushed back to the fluid vessel with positive pressure through the hydrophobic filter of the second filtering port, and the second aliquoting is repeated.

Therefore, in one embodiment there is an aliquoting module comprising a reaction chamber in fluid communication with a supply channel, and, a fluidic inlet in fluidic communication with the reaction chamber. The aliquoting module can comprises an open flow guide incorporated into the reaction chamber, in which case a shield (which can be made of plastic) may be desired to protect the open flow guide. In some instance, there can be a vent port to clear fluid in the supply channel and the vent port and an air space in the reaction tube. In other instances, once the fluid reaches a target level in the reaction tube and fills the central column leading to the gas permeable membrane filter, the filter stops the fluid flow. As a result of the flow being stopped, the flow guide breaks a continuous fluid flow coming from the fluidic inlet and isolates an aliquoted reaction volume in the reaction tube from the rest of the upstream fluid in the fluidic inlet.

In another embodiment, fluid dispensing into a reaction chamber(s) can be controlled by optical detection as the reaction chamber(s) is filled with liquid. In one embodiment, an excitation and/or detection port can be provided within the instrument at the defined height from the bottom of the reaction chamber which can detect the presence of an optically labelled fluid (for instance, fluorescently labelled) when a desired fill level has been achieved. In one embodiment, such excitation and/or detection ports can be provided through any device features in which the reaction chamber is seated. For instance, if the reaction chamber is seated in the device within a heat block, the excitation/detection port can be provided through the heat block. Once the presence of fluid is detected, feedback can be used to stop dispensing the liquid. In one embodiment, the feedback can be an increase in voltage from the detection element. In another embodiment, the detection element can be a single fiber optic element to be placed at the height of interest. In a further embodiment, excitation and/or detection may be accomplished from the top of the reaction chamber in configurations where the outlets and flow guides are positioned so as to not block such excitation/detection. In a further embodiment, a light detecting component such as a small photodiode could be attached to the end of a fiber optic where fluorescence level can be measured to detect the presence of fluorescent fluid. In one exemplary embodiment, when a sharp increase in fluorescence is detected by the system indicating the desired volumetric fill, the pump can be shut off. It is also within the scope of the present disclosure that detection of optical signals at different heights of the reaction chamber can occur, for instance in order to detect bubble formation behavior and its effect on the optical signals.

In yet a further embodiment, a feedback mechanism can be provided to detect the air/liquid surface boundary comprising methods such as shining a laser directly into an optical fiber or light guide. When the fluid boundary approaches the laser pathway and passes it, the light signal detected will display some discontinuity in incoming light, indicating that the fluid boundary has risen above the level of notification.

In one embodiment, there are provided one or more reaction chambers. Reaction chambers can be the site of downstream processing reactions, including amplification reactions. Amplification reactions are well known in the art, and the skilled artisan can readily use any suitable amplification reaction. In one non-limiting example, isothermal amplification, loop-mediated isothermal amplification (LAMP), and polymerase chain reaction (PCR) can be used. A plurality of reaction chambers may be fluidically connected to the lysis chamber, for example by means of a Y-branch, T-branch, or other similar configuration. Reaction chambers can include outlets connected to further aspiration (fluidic) ports or valves. One or more ports or valves can be used to control a plurality of vessels. In one embodiment, the ports or valves can include a filter designed to contain aerosols within the device.

In another embodiment, the reaction chambers can include dry reagents, which can be reconstituted by the introduction of liquid lysate. In one embodiment, providing heat to the reaction chambers may enhance the reconstitution's mixing process by inducing free convection flows.

In a further aspect of the present disclosure, there is provided a protective shield to protect and/or cover those elements of the cartridge described herein that may be fragile. For instance, the flow guide and filter covered outlet are used to dispense a controlled volume of liquid into a reaction chamber, as part of a sample-to-answer diagnostic cartridge. Such features can easily be bent, snapped off, or otherwise could be damaged during packaging, shipping or assembly, for instance, as in one embodiment, the reaction chambers can be assembled onto the cartridge prior to use. The shield covers the thin features so that packaging materials cannot apply stress to fragile sections. Additionally, the shield height matches other sections of the cartridge, so the complete device can be placed down without resting on the thin protrusions.

Figure 65:
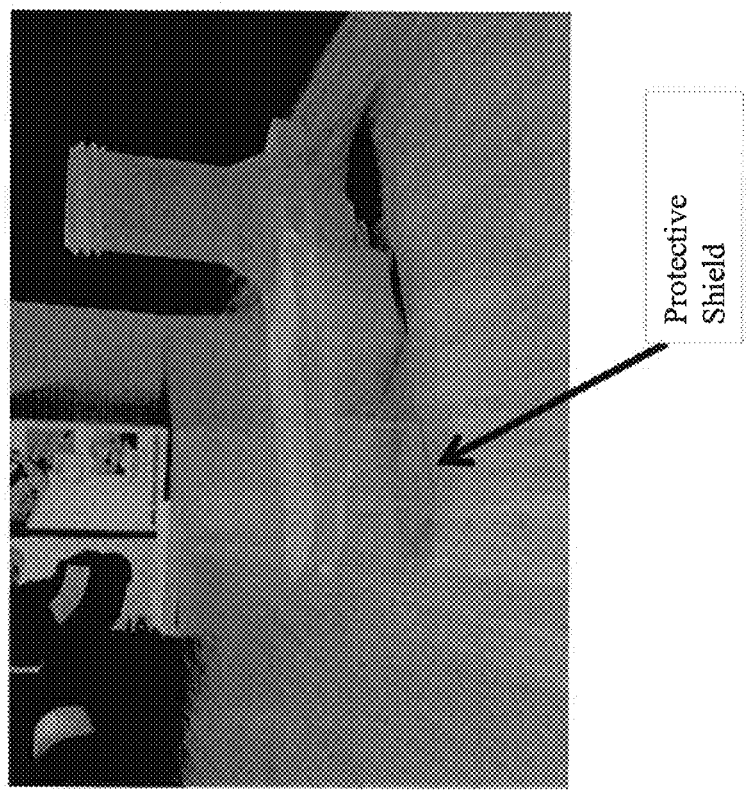
FIG. 65 demonstrates a protective shield for thin microfluidic features.

The shield 65125 shown in FIG. 65 is a solid plate—a protective shield with holes could also implemented. These holes would allow assembly of reaction chambers onto the main cartridge, while still providing handling protection.

In one embodiment, the cartridge is made typically of a polymer. Suitable polymers include PMMA, COC, COP, or polycarbonate.

Manufacturablity

As provided herein, a majority of the cartridge components shown have been produced using stereolithography printing. Such method of manufacture may not be feasible for scale-up production of cartridges. Alternate methods of manufacturing, such as molding, may require alterations to the specific design of the cartridge from those that are shown here, while still retaining the same functionality. Therefore, in one embodiment there is provided a geometric configuration which is easy for injection molding, assembly, and operation in accordance with the methods and workflows described herein.

Figure 66A:
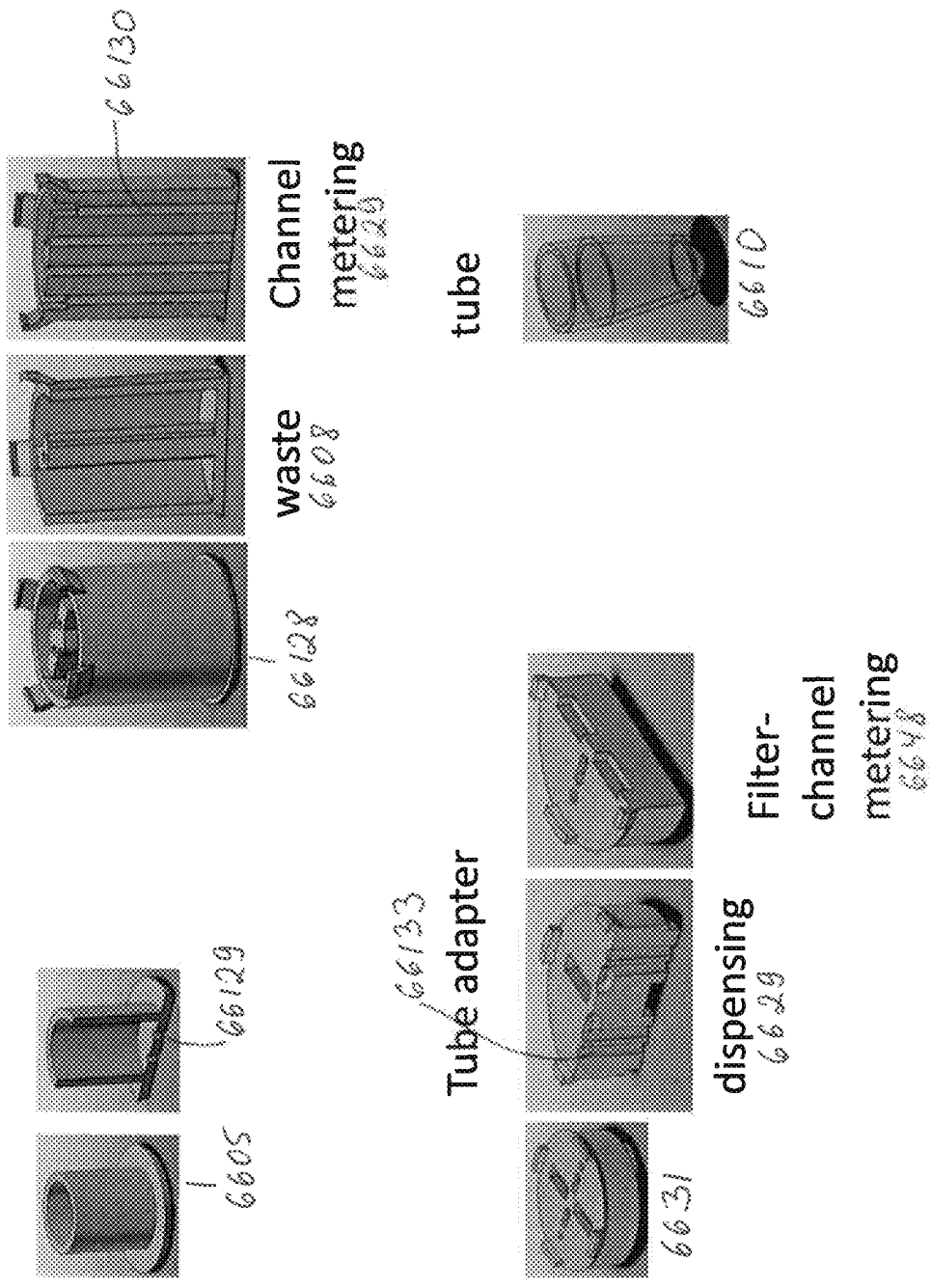
FIG. 66A shows a set of snap fit containers each equipped with geometry required for a certain function of workflow.
Figure 66B:
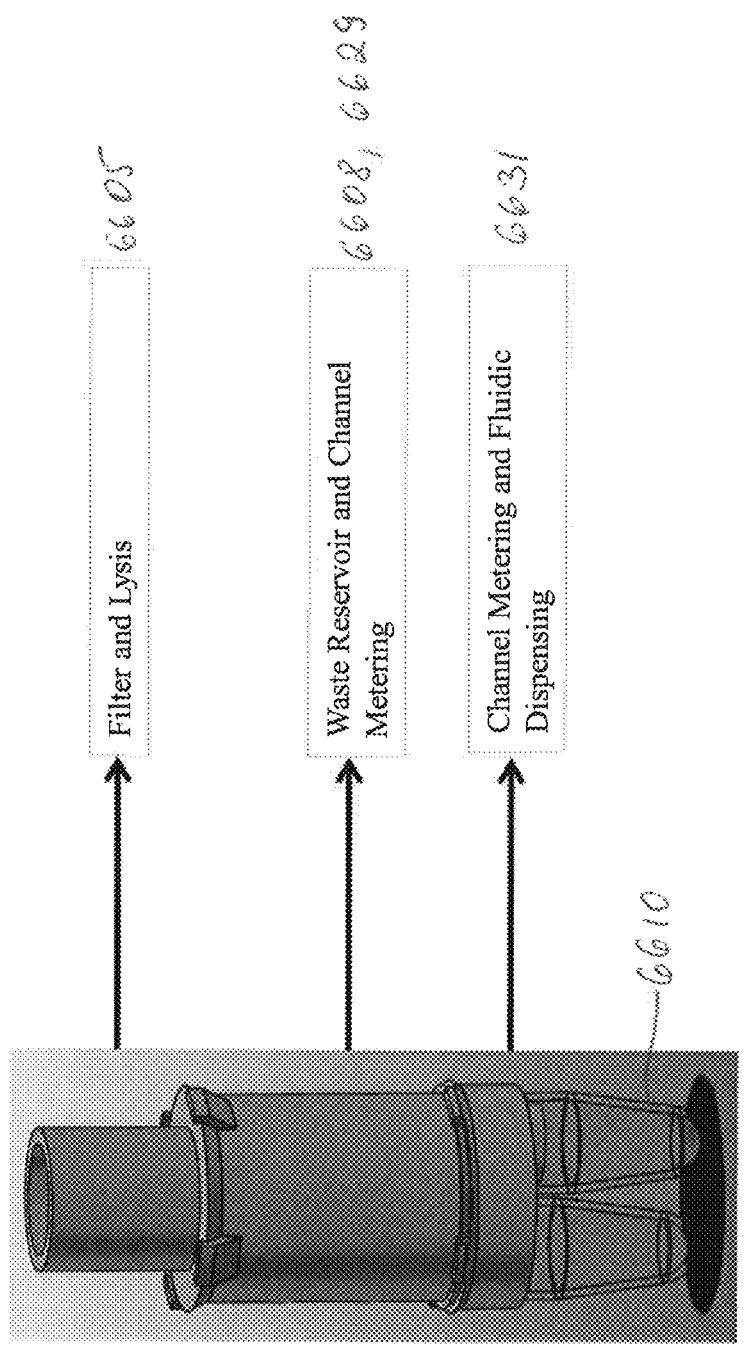
FIG. 66B shows the finished assembly of the part shown in FIG. 66A.

In one embodiment there is provided a set of snap fit containers each equipped with geometry required for a certain function of the workflow described previously and as discussed herein. In one embodiment as shown in FIG. 66A, the first piece of the assembly includes a moldable lysis container 6605 where wash fluid and the sample will be filtered through and lysis will take place. The second moldable piece will consist of a waste chamber 6608 at one configuration and a channel metering 6629 method in another. The third moldable piece will consist of the filters 6648 required for channel metering in one configuration and the channels 6629 necessary to aliquot to a moldable tube 6610 in another. Alternating between configurations simply requires the sliding rotation and alignment of each container with its adjacent part along the central axis. FIG. 66B provides a schematic of the components of FIG. 66A as assembled.

Workflow

Filtration and Waste

Pre-wet, sample, and post wash samples are dispensed into the waste container 6608. In this configuration, the two "filter and lysis" chamber outlets would be aligned with the waste ½ channels 66126 shown in FIG. 66C and a negative pressure port located in the waste reservoir would pull upstream liquid into the waste reservoir.

Lysis

Figure 66D:
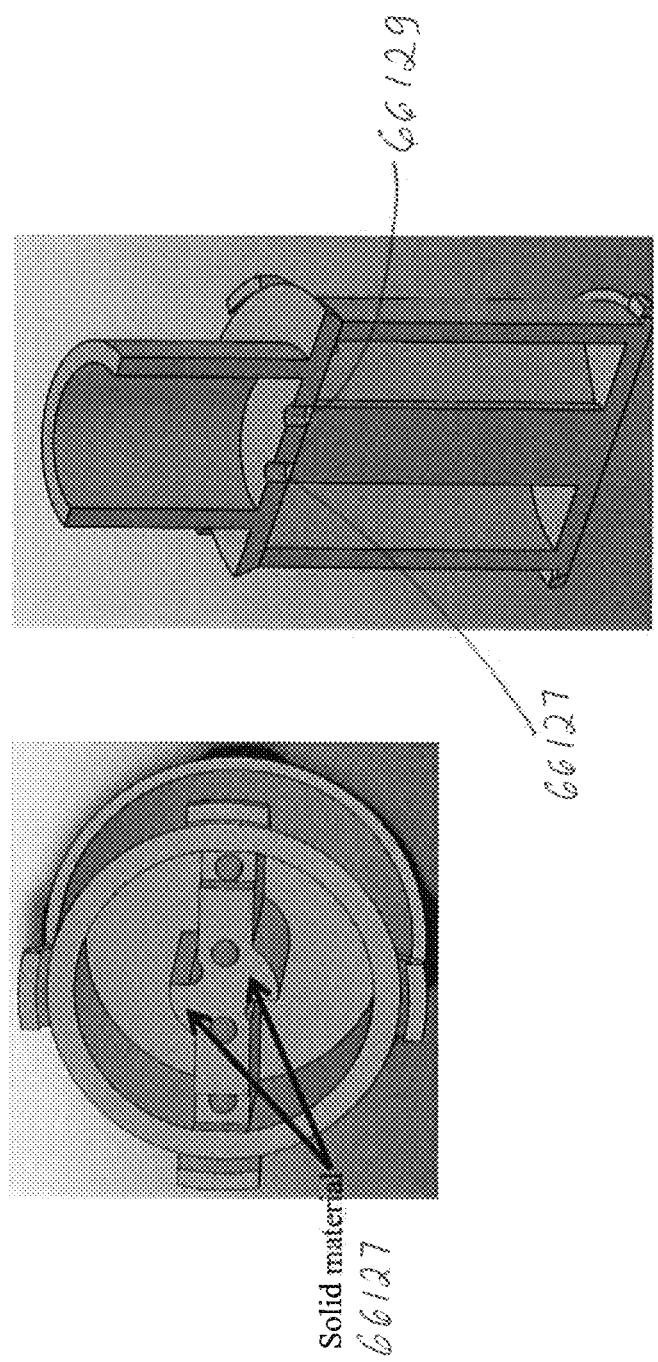
FIG. 66D shows rotation of the "filter and lysis" chamber so that two channels are directly above the solid material and fluid cannot escape as lysis is taking place.

The "filter and lysis" chamber 6605 is rotated, for instance via a stepper motor in the instrument, so that two channels 66129 are directly above the solid material 66127 so fluid cannot escape as lysis is taking place as shown in FIG. 66D.

Channel Metering

Figure 66E:
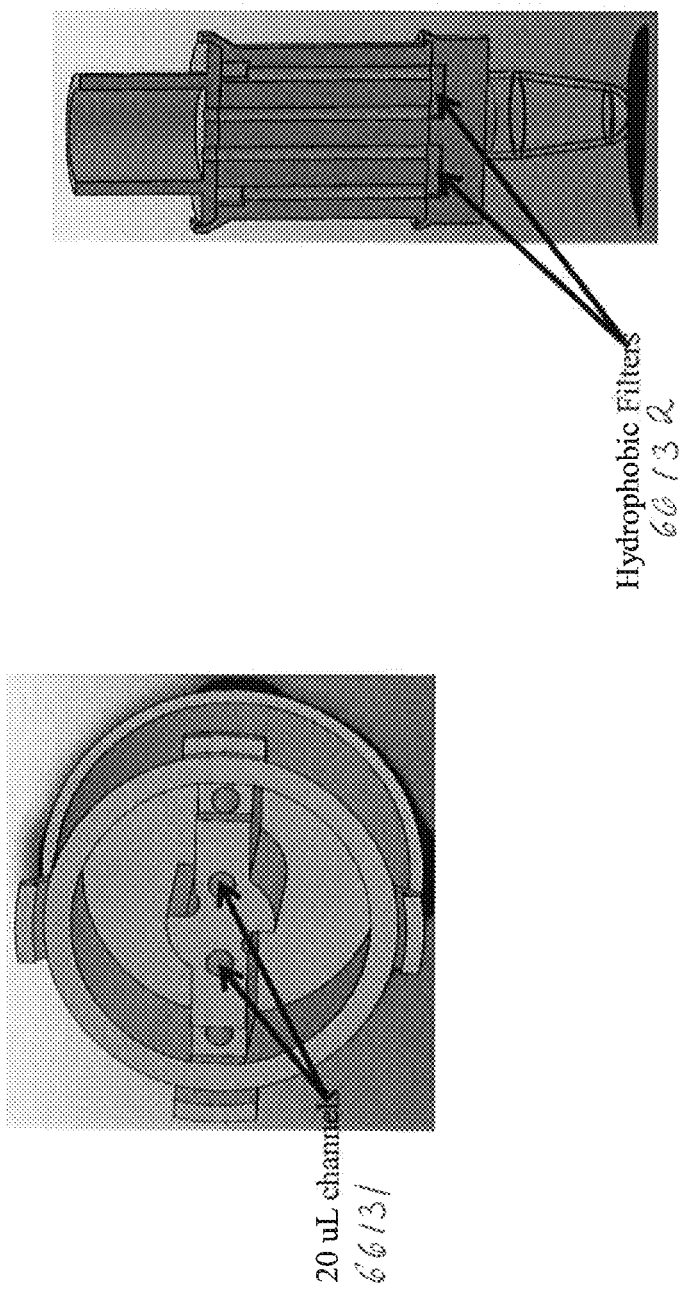
FIG. 66E shows fluid from the "filter and lysis" chamber being pulled (via waste chamber) until the fluid makes contact with the hydrophobic filter.

After the end of lysis, the "filter and lysis" chamber 6605 would then be rotated so both channels 66129 are aligned with the channels 66130 of the "waste and channel metering" piece 66128. After this alignment, a constraint would prevent the "filter and lysis" chamber 6605 from being rotated any further (not shown). Fluid from the "filter and lysis" chamber 6605 would then be pulled (via waste chamber) until fluid makes contact with the hydrophobic filter 66132 shown in FIG. 66E. In one embodiment, the length of the channel being filled would contain 20 uL of volume, such that the amount to be dispensed can be altered by changing the length and/or width of the channel.

Isolation of the 20 uL Lysate From the "Filter and Lysis" Chamber

After the 20 uL liquid channel 66131 is filled with lysate, the "filter and lysis" chamber 6605 is rotated in the opposite direction to realign the two channels 66129 with the waste chamber 6608 so the rest of the lysate can be pushed into waste.

Dispensing Metered Liquid

Figure 66F:
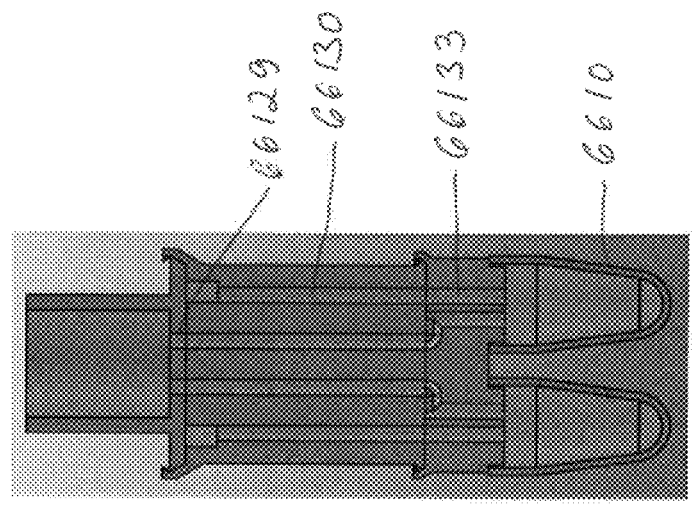
FIG. 66F shows aligning "filter and lysis" chamber channels and "tube adapter" channels with "waste and channel metering" channels.

"Filter and Lysis" Chamber Channels 66129 and "Tube Adapter" Channels 66133 are aligned with "Waste and Channel Metering" channels 66130 as shown in FIG. 66F to dispense 20 uL liquid into each tube 6610. After this the tube 6610 can be isolated from the upstream channels by further rotation.

In one embodiment of the present disclosure, performing the above workflow can provide several benefits including isolating waste and lysate channels so no cross contamination can occur, the need for only one pressure port in the "Waste and Channel Metering" to drive all negative pressure in the cartridge, easy to mold parts with adjustable aspect ratio and sizes for more cost effective manufacturing, generation of a sealable press fit design (with the use of, for example, gaskets, not shown) by assembling simply molded components as opposed to bonding or welding (easy assembly). Further, other benefits of performing the above workflow include collection of a directly lysed solution from the lysis chamber rather than moving the lysed solution through a channel shared with waste flows, design allows for side excitation and detection optics so downstream analysis methods can remain unchanged, all functions using rotation are performed along one axis for ease of instrument design and use, and all functions are performed without the need for valves.

Thus, in one embodiment there is provided a rotatable cartridge for analyzing a biological sample for the presence of a target of interest, the cartridge comprising a first element comprising a cap having a sample and lysis chamber containing a capture filter, wherein at least one outlet is present under the capture filter; a second element comprising a waste chamber having a center portion comprising at least two through channels disposed within a solid section, and a pneumatic port; a third element comprising at least two channels extending from the top of the third element through a top portion of the third element, at least one hydrophobic filter located on the top portion of the third element and offset from the at least two channels, and at least one reaction chamber disposed below the top portion of the third element, such that the at least two channels are in fluid communication with the least one reaction chamber; wherein, the first, second and third elements are vertically stacked and are rotatable with respect to each other around a central axis, such that the outlets, channels, chambers, and filters can be placed into and out of fluidic communication from each other by rotating one or more of the elements.

The elements can be assembled via a snap configuration, a tab and lock configuration, or is screwed together wherein there is additional play in the rotation to allow for the rotation of the elements with respect to each other while being connected. The rotatable cartridge can use one or more of gaskets, or o-rings to create fluid-tight seals between the elements when the outlets and channels are not in alignment, or wherein the elements are made of deformable/compliant plastic that will form a fluid-tight seal. The first element can additionally comprise at least one side outlet to allow removal of fluid from the sample and lysis chamber without the fluid entering the waste chamber or the at least one reaction chamber. The cartridge can be manufactured by molding, etching, or stereolithography printing and can be made of any suitable plastic.

In one embodiment, the rotatable cartridge is used by rotating the first and second element to a start position such that the first element's outlet is in fluid communication with the waste chamber; adding a sample to the sample and lysis chamber; applying pressure through the pneumatic port to draw the sample through the capture filter and into the waste chamber, such that any targets of interest remain on or in the capture filter; rotating the first and second element to a closed position where the first element's outlet is over the second element's solid section, thereby fluidicly sealing the sample and lysis chamber from the waste chamber and from the second element's through channels; adding a lysis solution to the sample and lysis chamber; lysing the targets of interest; rotating the first and second elements so that the first element's outlets are in fluidic communication with the second element's through channels, and such that the second element's through channels are over the third element's hydrophobic filter; applying pressure through the pneumatic port, such that negative pressure is provided through the second element's channel having a side opening, through the third element's hydrophobic filter, into the second element's complete through channel and into the first element's outlet below the capture filter; wherein the lysate is pulled through the first element's outlet, into the second element's through channel towards the third element's hydrophobic filter, wherein the lysate's movement will stop once the hydrophobic filter becomes wet, causing an aliquot of the lysate to be held within the second element's complete through channel; rotating the second element with respect to the third element so that the second element's through channels are in communication with the third element's channels and the reaction chamber; applying pressure through the pneumatic port, such that the aliquot of lysate is dispensed into the reaction chamber; rotating the second element with respect to the third element such that the reaction chamber is fluidically isolated; performing an analysis reaction within the reaction chamber; and monitoring the analysis reaction to determine whether a target of interest is present.

In another embodiment, additional wash steps can be performed by adding wash solution and rotating the elements to allow the wash to be pulled into the waste chamber when pressure is applied. If emptying of the sample chamber is desired once the aliquots have been drawn off or deposited, the elements can be rotated to pull the remaining fluid into the waste chamber while keeping the reaction chamber and/or the metering channel isolated. In another embodiment, there can be additional channels, reaction chambers and/or filters in the third element to allow for dispensing of multiple additional aliquots once the initial aliquots have been made and the reaction chambers are sealed off.

Controlled Pre-Filter Extraction and Separation

In one embodiment, there is provided a mechanism for filtering samples that may contains target of interest by utilizing at least two filters. Such an embodiment can be useful with the sample is particularly particulate rich, or when clogging of a filter is anticipated. In one embodiment, a pre-filter is used above a capture filter, wherein the sample, is subjected to lysis, including a chemical lysis or heat controlled pre lysis, prior to being filtered through the pre-filter. In one embodiment, the lysis step will extract any targets of interest potentially present within a host cell (i.e., bacteria or viruses present in a human host cell) by breaking any such host cell, so that large cellular material such as the nucleus and any large membrane material is prevented from entering the second, target genomic material extraction region.

The next step includes the filtration of the partially lysed material and any targets of interest through a pre-filter which can trap any host cell debris or un-lysed nuclei from entering the target genomic material extraction region. Lysis can then be conducted as previously described to extract genomic material from the targets of interest to be captured on a capture filter, such as a GE Fusion 5 filter or other glass fiber filter, for example. In another embodiment, a pre-filter can be present directly above the capture filter. In another embodiment, centrifugation can also be used to force material through a pre-filter rather than using a first lysis step.

Maze Cartridge

In one embodiment of the present disclosure, there is provided a proposed moldable product of the cartridge described previously.

Figure 68A:
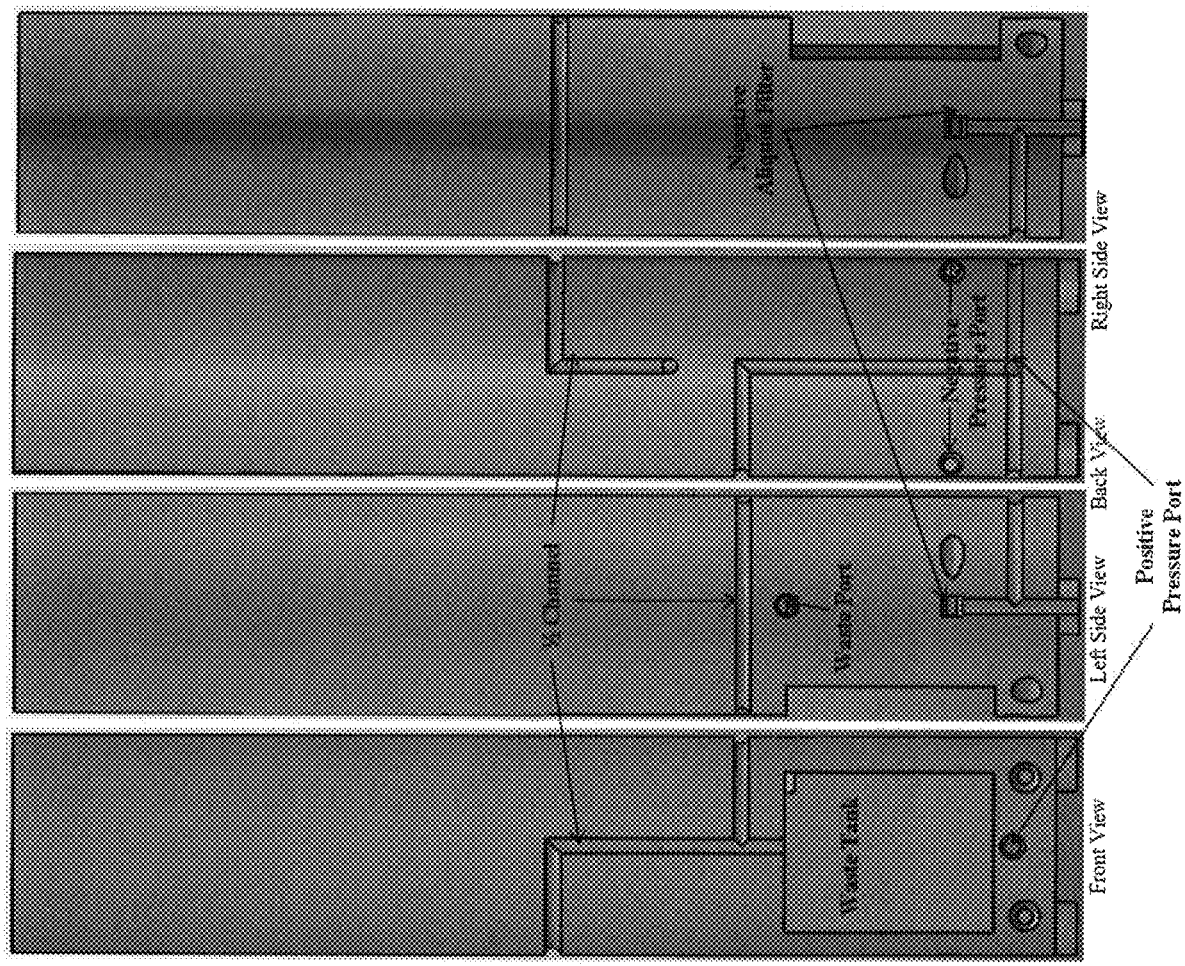
FIG. 68A demonstrates a cartridge including all elements of a 3D printed cartridge with channels trailing along the outside for a one part mold.

In one non-limiting embodiment, the cartridge shown in FIG. 68A contains sample and lysis chambers at the center of the cylinder, a channel extending from the lysis chamber to the outside edge of the cylinder, and remaining channels and waste chamber along the outside surface of the cylinder (as half channels). The final assembly step would then include the insertion of all filters and reaction tubes, and the bonding of a thin plastic sheet along the outside of the cylinder to close all ½ channels. In one embodiment, this design includes all components cartridges described previously, including channel metering using negative pressure and hydrophobic filter, and positive pressure to aliquot 20 uL, or any desired amount based on the exact aliquoting configuration.

Figure 68D:
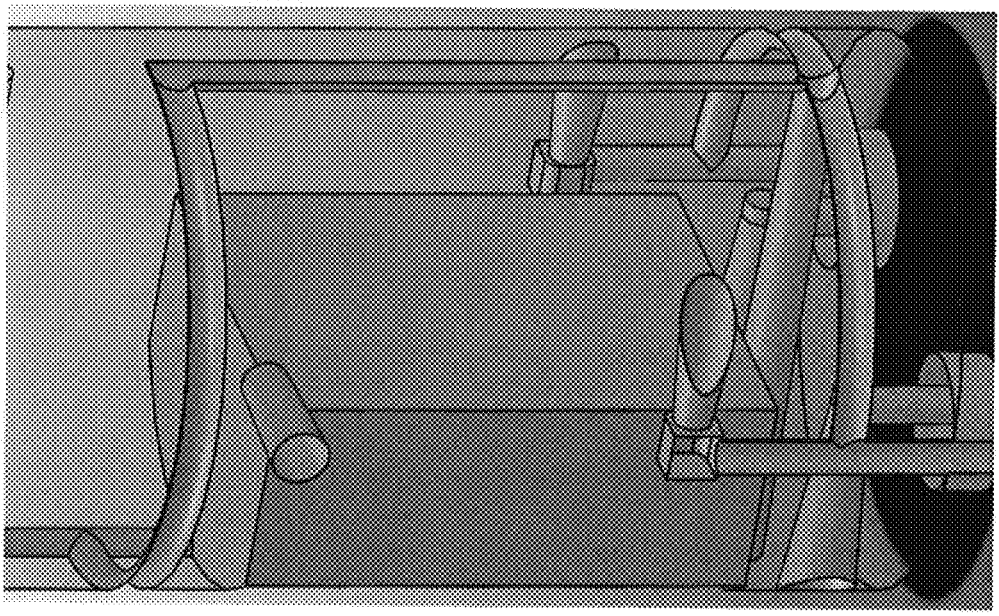
FIGS. 68B-D demonstrate 3D transparent views of all channels, chambers, and ports.
Figure 68C:
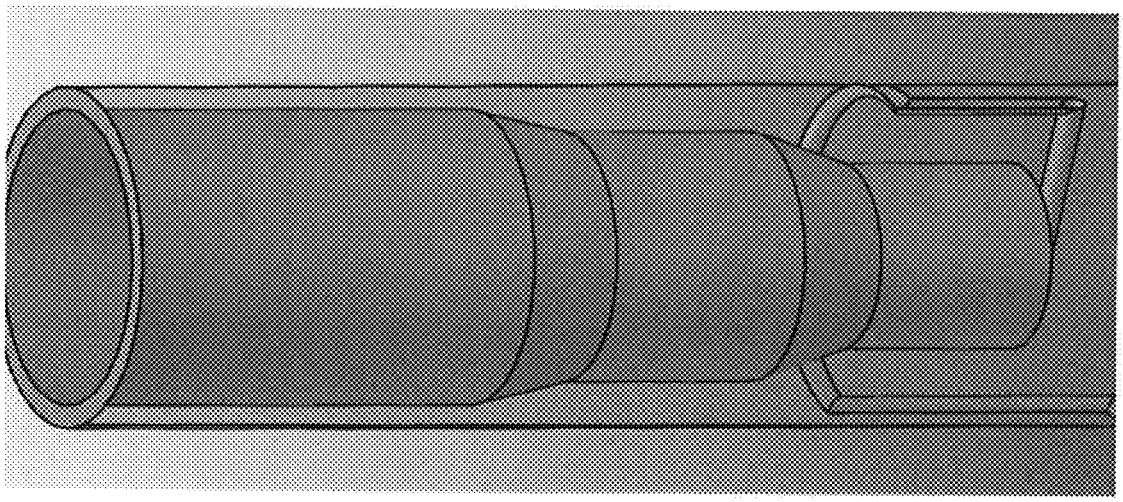
Figure 68B:
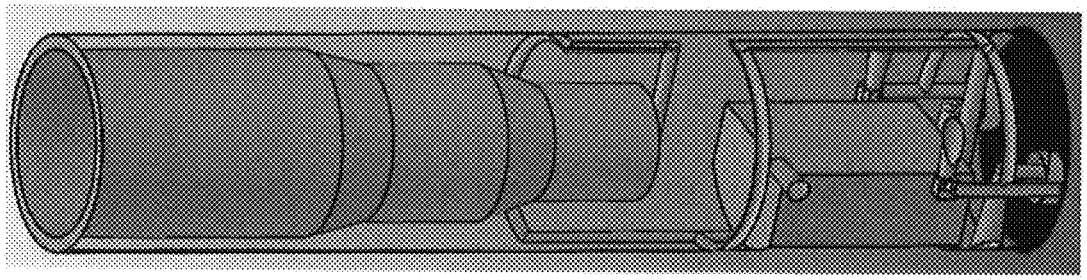

FIG. 68A depicts all elements of the cartridge, with channels trailing along the outside for an easy single part mold. In another embodiment, molding could comprise constructing 3 separate molded parts and bonding them. In this embodiment, one central molded part (the cartridge) would be required, as well as an external sheet of plastic to close channels and the waste tank from the outside. FIG. 68B-D provides a 3-D transparent view so all channels, chambers, and ports are visible.

Alternate Cartridge Design

Figure 67:
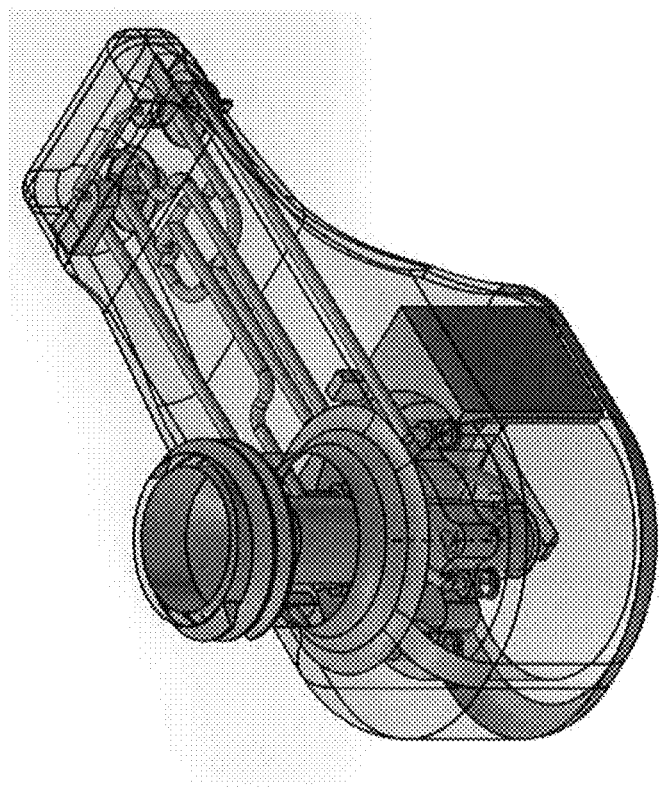
FIG. 67 demonstrates a cartridge designed for use with a point of need diagnostic system.

In an embodiment shown in FIG. 67 is provided an alternative cartridge designed for use with a point of need diagnostic system. The concept includes several features designed to improve usability and instrument design. In one embodiment, the cartridge has a flat bottom to allow stable placement on benchtops or other surfaces. This would aid the user while filling the cartridge, preparing multiple cartridges, or disposing of a used cartridge. This design reduces the chance of leakage or accidental spills. A further additional embodiment of a cartridge that can be used in the present disclosure is depicted in FIG. 29.

In an additional embodiment, the cartridge employs a cylindrical chamber for heat lysis. All pressure connections in the cartridge are situated in a ring around the lysis chamber—in this embodiment, the pressure connections are made as the lysis chamber is inserted into the instrument. In other designs, multiple pressure connections across the cartridge may leak if the cartridge is tilted. This design can additionally be more robust with regards to cartridge misalignment as this design may provide better feedback to the user, if the cartridge is misaligned.

In another embodiment, the cartridge waste chamber is wrapped around the cylindrical lysis chamber, helping to reduce footprint. The waste tank can be curved to fit inside a smaller, easy-to-hold cartridge envelope.

It should be appreciated that the configuration described above is exemplary and should not be interpreted as limiting the scope of the disclosure. Rather, it is intended to provide an example of the many configurations possible that utilize the cartridge components described herein.

Blister Mount Cartridge

In one embodiment, the reagents required for any of the workflows provided herein can be stored on the cartridge body in a variety of methods, including tanks, blisters with a frangible seal, pouches, etc. The release or transfer of these stored reagents into the cartridge chambers can be actuated with a number of methods, such as solenoids, piston plungers, hollow needles, etc. A plurality of storage vessels can be used, with a single actuator or multiple actuators. A single reagent storage vessel can be used to provide multiple reagents.

Sample Preparation Only

In an alternative embodiment, some cartridge features and components can be combined to create a device capable of rapid sample preparation for downstream diagnostics. This device could comprise the vented cap, sample tank, check valve, and lysis chamber as described above. The waste chamber can be integrated with the cartridge or waste can be stored separately. Raw patient sample, which can include blood, urine, sputum, etc, would be input into the cartridge. Filter-based concentration and extraction of target biological material would take place, as described above. Instead of transferring lysate to an aliquoting feature, the lysate can be removed by the user for use in other diagnostic processes.

Amplification and Detection Only

In an alternative embodiment, some cartridge features and components can be combined to create a device capable of rapid PCR and detection of a DNA sample. This device would comprise the aliquoter feature, amplification vessels, and an external input for DNA sample. The user would input a sample containing extracted DNA, which would be automatically metered into the amplification vessel via the aliquoting features. The vessel can then be rapidly thermocycled for PCR. Similar to the complete embodiment, the amplification vessels can come preloaded with reagents. There can be a plurality of amplification vessels, capable of testing a single sample for multiple targets. A plurality of inputs can also exist, testing multiple samples for multiple targets.

Figure 30:
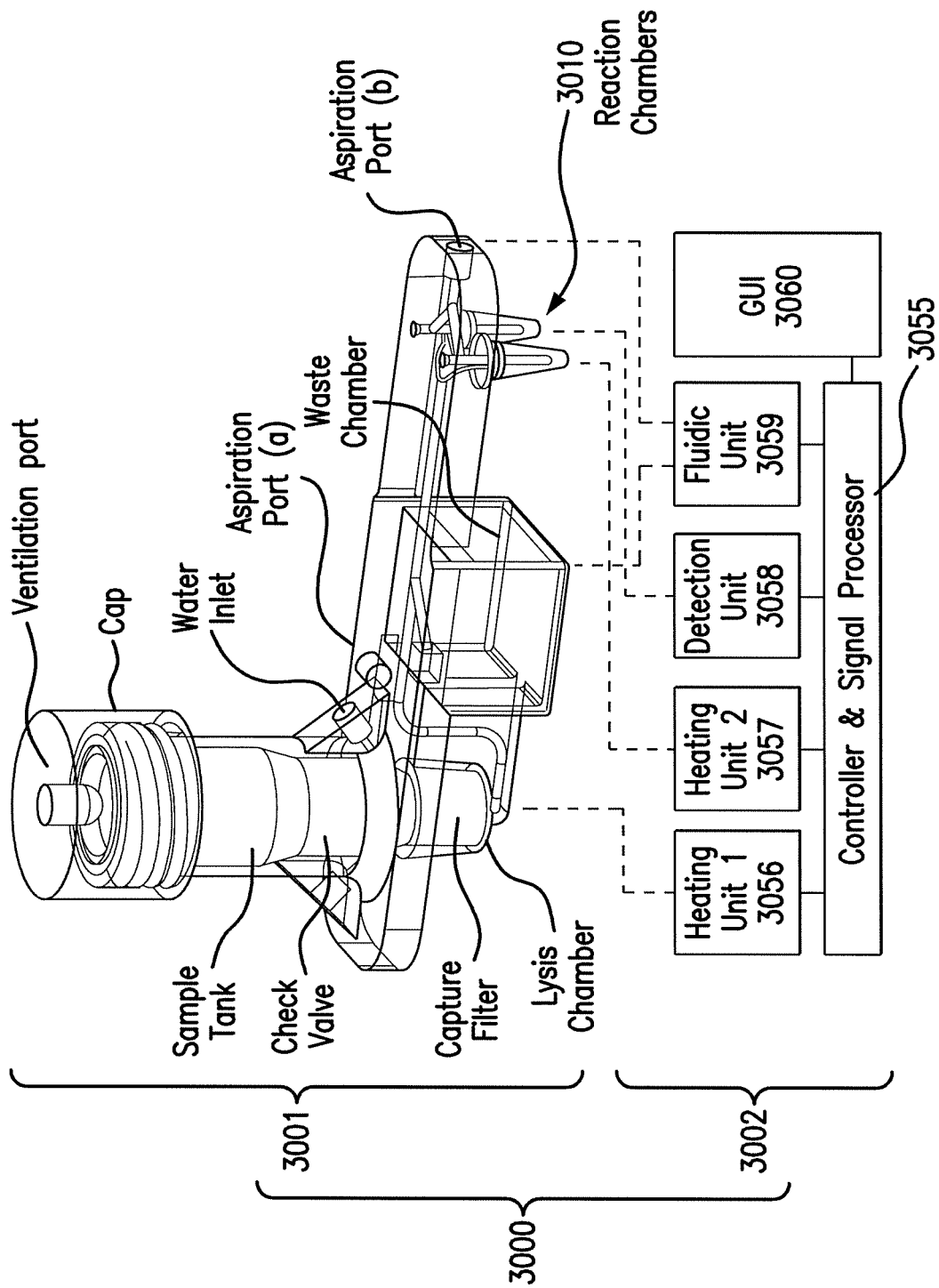
FIG. 30 demonstrates a process flow, disposable cartridge, and control diagram according to the present invention.

In one embodiment of the present disclosure is provided a device that will accept the cartridge previously described herein to allow a sample to be processed and analyzed for the presence of a target of interest. In one embodiment, a control diagram of an exemplary device is provided in FIG. 30. System 30 is comprises of cartridge 3001 and device 3002. Cartridge 3001 can have any of the configurations or embodiments described herein. In one embodiment, Device 3002 has a controller and single processor 3055 which is in communication with each of a first heating unit 3056, a second heating unit 3057, detection unit 3058, fluidic unit 3059 and a graphical user interface (GUI) 3060.

Figure 31:
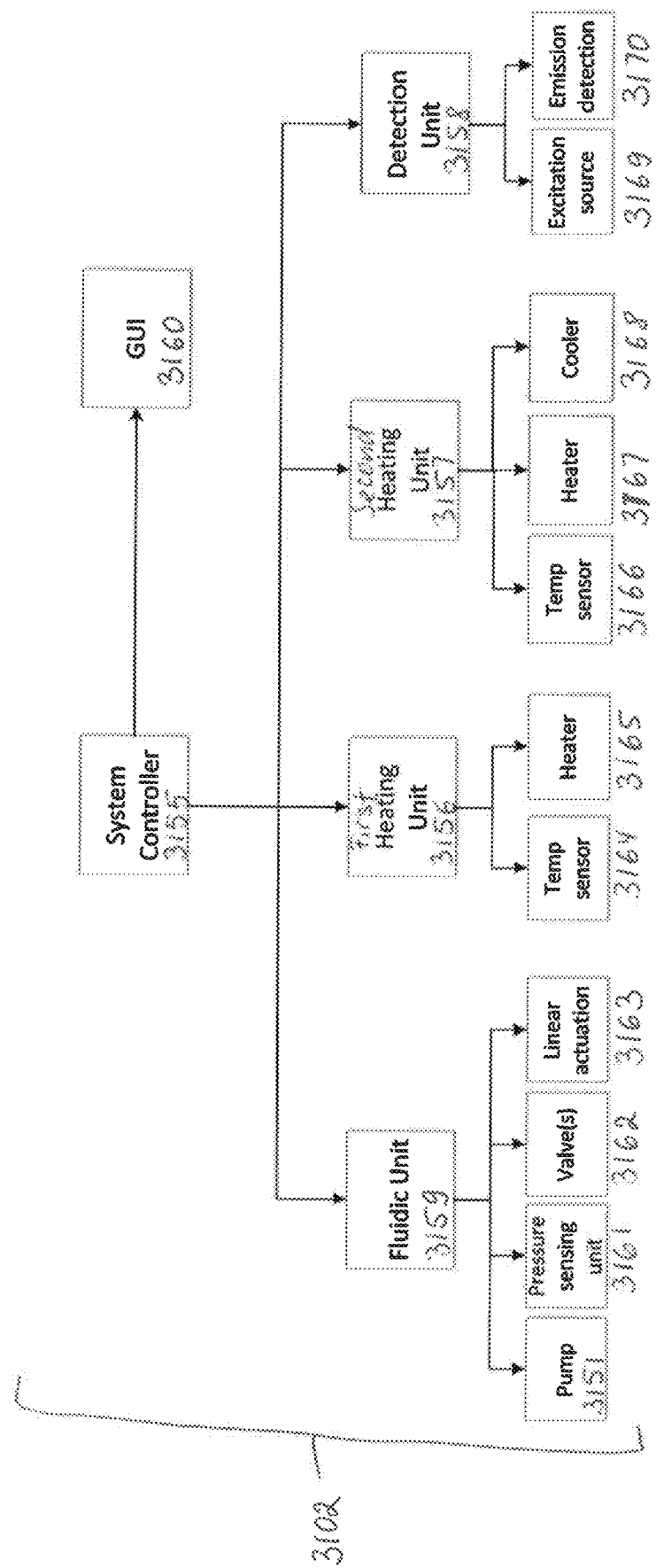
FIG. 31 provides a system control diagram.

In another embodiment, as shown in FIG. 31, there is provided a system controller 3155 which is in communication with a GUI 3160. The system controller 3155 is additionally in communication with a fluidic unit 3159, a first heating unit 3156, a second heating unit 3157 and a detection unit 3158. In one embodiment, fluidic unit 3159 comprises and is in communication with pump 3151, pressure sensing unit 3161, at least one valve 3162 and linear actuation unit 3163. In another embodiment, first heating unit 3156 comprises and is in communication with temperature sensor 3164 and heater 3165. In another embodiment, second heating unit 3157 comprises and is in communication with a temperature sensor 3166, heater 3167 and cooler 3168. In yet another embodiment, detection unit 3158 comprises and is in communication with excitation source 3169 and emission detection unit 3170. In one embodiment, those elements depicted in FIG. 31 as being part of more than one unit can in practice be represented by either a single element that functions within more than one unit or by multiple elements that each function within a single unit. For instance, in one non-limiting embodiment, the temperature sensor 3164 that is in communication with first heating unit 3156 could be the same temperature sensor as temperature sensor 3166 which is in communication with second heating unit 3157. Alternatively, temperature sensor 3164 can be a different temperature sensor than temperature sensor 3166. Similarly, in another embodiment, those units depicted in FIG. 31 as being separate components of the device 3102 can in practice be represented by either a single unit with more than one function, or as multiple units that each function within device. For example, in one non-limiting embodiment, first heating unit 3156 can be the same heating unit as the second heating unit 3157, or alternatively, heating unit 3156 can be a separate unit from heating unit 3157. In another embodiment, some units or systems may include more or less components than those depicted in FIG. 31.

In one embodiment, a controller 3055 can be used to coordinate the process and interface with the other various unit. The controller 3055 can comprise one or more computing units (e.g., single board computer, processor, microcontroller, etc.). In one embodiment, the controller can store and execute a script. In another embodiment, the controller comprises retrievable memory.

In one embodiment of the present disclosure, fluidic unit 3159 can perform pneumatic control of the device 3102. Pressures can be sensed at one or more of the vents or aspiration ports using, for example, piezoresistive transducers. A pump (e.g., peristaltic, vacuum, piston, or syringe pump, etc.) can be used to drive fluid through the device. The pump can work in conjunction with measured pressures using a feedback control mechanism such as PID control. One or more valves can be used to selectively activate a specific port or vent. Valves can also be used to build pressures to a pre-determined amount before application to the device (e.g. by using an accumulator). Further, some systems can include one or more linear actuators. Linear actuation can be used, for example, to crush a reagent blister pack (e.g., using a solenoid or stepper motor).

In another embodiment of the present disclosure, various heating units 3156, 3157 can be utilized. One heating unit can be used for lysis 3156 and another for amplification 3157. Alternatively, the same heating unit can be used for both processes. A lysis heating unit 3156 will include a heating means 3165 (e.g., resistive, inductive, IR, etc.). In one embodiment, the heating unit 3156 will include a temperature measurement means 3164 such as a thermistor, RTD, thermocouple, IC temperature sensor, etc. In some embodiments, the heating unit 3156 will control the temperature of the device using feedback control (e.g., ON-OFF or PID). An amplification heating unit 3157 can further include a cooling means 3168 if the device needs to be rapidly cooled, as is the case in PCR or any other reaction that requires thermal cycling or efficient cooling of a sample. The cooling 3168 means can comprise a Peltier, fan, liquid cold plate, heat sink, heat pipe, etc.

Figure 32C:
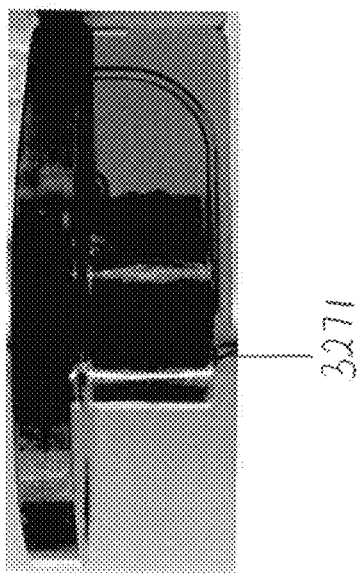
FIGS. 32A-C demonstrate A) bottom view of the capture tester containing the capture filter (shown in white) within the lysis reservoir. B) Tapered outer edge of the effective heating region which contains the capture filter assembly and inlet and outlet channels. C) Assembly of the reservoir to the custom heat block achieving a line to line fit to ensure fast heat lysis.
Figure 32B:
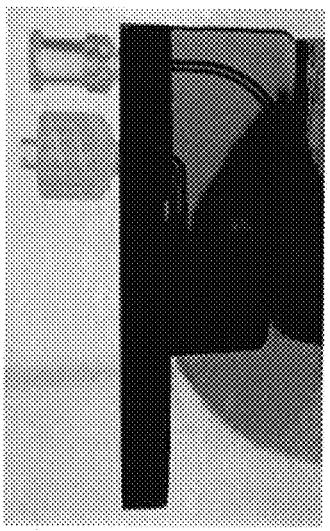
Figure 32A:
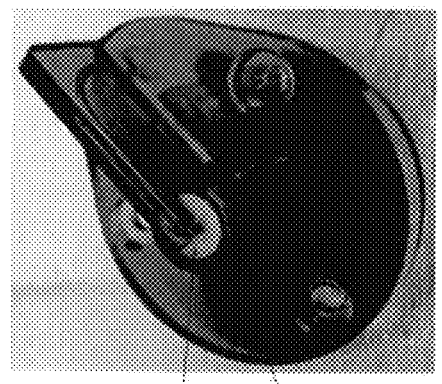
Figure 33C:
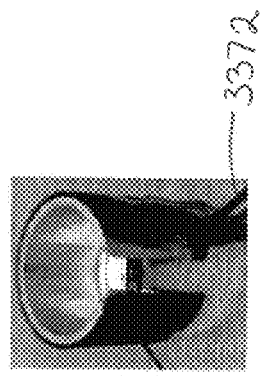
FIGS. 33A-C demonstrate A) 3D representation of the heat block. B) Front view of the heat block with dashed inner outlines where contact will be made with the outer surface of the trapped cell reservoir. C) Assembly of the block which provides the lysis chamber with heat.
Figure 33B:
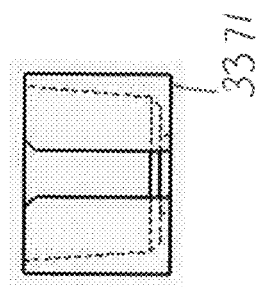
Figure 33A:
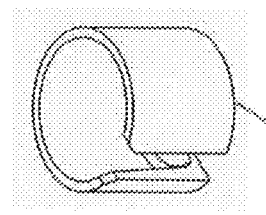

In order for the first heating unit 3156 to successfully heat lyse targets of interest immobilized on the capture filter, it is necessary to create a conductive heat block providing an exact fit attachment around such a lysis reservoir. In one embodiment, FIG. 32A provides an exemplary partial cartridge having a lysis chamber 3205 and a capture filter 3221. FIG. 32B depicts a tapered outer edge of the effective heating region which contains the capture filter assembly 3221 and the inlet and outlet channels. FIG. 32C depicts assembly of the lysis chamber 3205 to a custom heat block 3271, achieving a line to line fit to ensure fast heat lysis. In another embodiment, a rapid heat source is needed to allow effective heat transfer into the target sample. Therefore, in one embodiment, the resulting heating unit can include using a Kapton or other similar heater surrounding the cylindrical outer surface of heat block, for instance a custom aluminum block 3371 (outer solid outline shown in FIG. 33A), which contains specific geometry within its contents to allow for the specific profile of the lysis chamber (inner dashed outline shown in FIG. 33B). In one embodiment, the lysis chamber 3205 shown in FIG. 32B is designed with a tapered outer edge to ensure outer surface contact with the inner surface of the designed heat block 3371 (shown in dashed lines in FIG. 33B). In another embodiment, and a thermistor can be present on the outside of heat block 3371 to measure temperature to provide the system with feedback for real time temperature control.

Figure 33D:
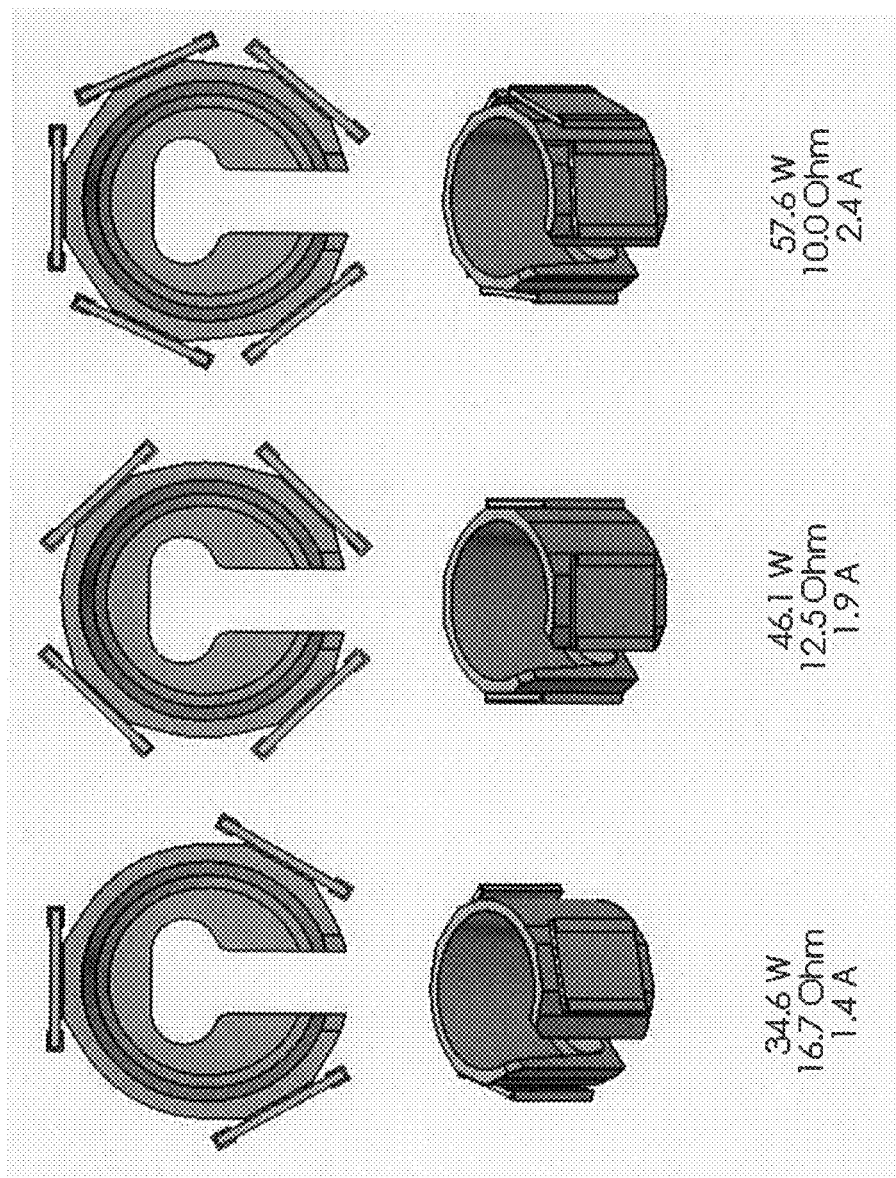
FIG. 33D demonstrates multi-faceted heat block designs with 3, 4, or 5 chip heaters.

In another embodiment, alternative heat block designs are provided, as shown in FIG. 33D. It is within the present description that these multi-faceted heat blocks can feature the same interior dimensions as described above to fit tightly to a lysis chamber having an external feature, however the multi-faceted heat block can additionally feature several flat faces for attaching high power aluminum nitride resistors (e.g., RP3 or RP4 series resistors from AVX). In one embodiment, FIG. 33D provides a multi-faceted heat block design with 3, 4, or 5 chip heaters spaced around the outside of the heat block. In one embodiment, the heaters can be spaced equidistant around the heat block. In another embodiment, the heaters are not spaced equidistant around the heat block. In one non limiting embodiment, by using 50 ohm resistive heaters in parallel and powering them with a 24V supply, 35-58W can be generated. Such configurations can allow more power to be delivered to the lysis chamber without requiring the use of fully custom components.

Figure 34B:
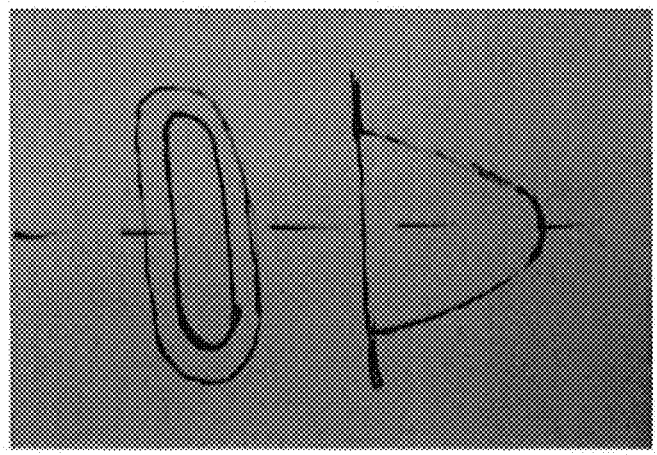
FIGS. 34A-B show a multi-walled vessel for rapid heat lysis.
Figure 34A:
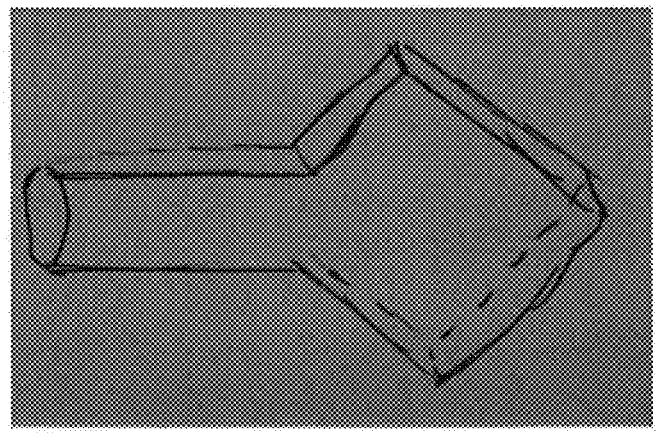

In a further embodiment of the present disclosure, there is provided a multi-walled vessel (left) that can be sandwiched between opposing heater plates. In another embodiment, the multi-walled vessel can be used as the structure for any of the chambers or receptacles within the present disclosure in which heating and cooling are desired, for example, a lysis chamber or a reaction chamber. The sandwich structure allows a relatively large surface area to be used for heating while making the heat conduction distance short. In one embodiment, the walls of the multi-walled vessel and the chamber depth are thin to promote rapid heat conduction. It is within the scope of this disclosure that the sandwich design provides that the heaters can be pressed against the surface with a large force to minimize thermal contact resistance. In a further embodiment, the vessel can alternatively be shaped as an elongated ellipsoid (FIG. 34A-B). In yet a further embodiment, the multi-walled vessel can be placed between opposing cooling plates (for example, a Peltier device) that is capable of heating and cooling. In this embodiment, the multi-walled vessel can be the lysing chamber, such that a user can lyse targets of interest through freeze/thaw cycling.

In another embodiment, a flexible, conformable interface can be used improve heat transfer to the lysis chamber by maximizing surface contact. In one embodiment, a flexible heater can be used to conform to a rigid lysis chamber. For example, a flexible kapton heater, or a phase-change material can be used. In another embodiment, a portion of the device's heating unit can be pre-heated, turning it into a liquid or gel. The lysis chamber can be inserted into this liquid, creating a good thermal interface to improve heat lysis. After removal of the cartridge, the liquid would cool and return to a solid state. In another embodiment, the lysis chamber can alternatively be made flexible, so that it can conform to a solid heating unit. For instance, this could be accomplished by using a flexible, thin membrane for the lysis chamber walls. In one embodiment, negative or positive pressure could be applied to ensure a good interface between the flexible membrane and a rigid heater.

Figure 35B:
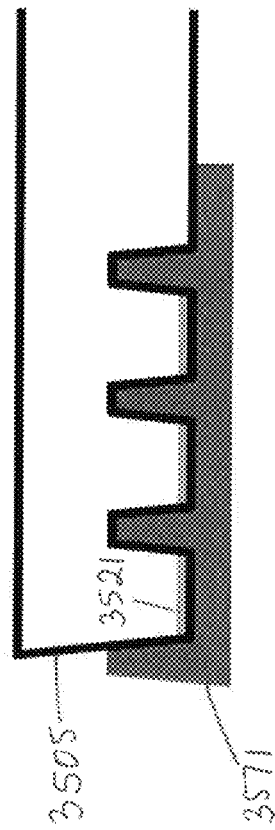
FIG. 35B shows a side section view of the lysis chamber.
Figure 35A:
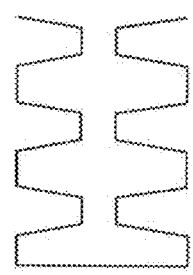
FIG. 35A shows a fin configuration of a lysis chamber heater.

In a further embodiment, a lysis heater can be provide having with fin elements designed to house a lysis chamber also designed with fin elements. FIG. 35A provides top view of a non-limiting example of one such configuration, which can provide faster and more uniform heat lysis by increasing the overall surface area of heat applied to the liquid. FIG. 35B provides a side section view of what the assembly might look like depicting a lysis chamber 3505 having capture filter 3521 mated to heat block 3571. In another embodiment, the fin elements can be provided on any chamber and corresponding heater unit within the instrument, for example, the reaction chamber(s).

In another embodiment of the present invention, it can be beneficial to confirm that a sample processing step has occurred, such as the step of heat lysis of targets of interest. In one embodiment, a heat lysis process can be used to open cells, for example, bacterial cells, and expose genetic material for downstream processing and diagnostics.

It is within the present disclosure that multiple embodiments of an engineering control to confirm heat lysis are possible. In one embodiment, color-change tape or another similar material can be used on the outer surface of the cartridge or lysis chamber. After heat lysis has occurred, the tape or similar material can change color to indicate to the user that the process is complete. Such an embodiment can assist with troubleshooting the functionality of the system, as well as confirming deactivation of any infectious agents in the sample.

In another embodiment, a pressure sensor measurement can be used to confirm heat lysis has occurred. When heating of the sample takes place in a lysis chamber, air in the chamber expands and changes the localized pressure. Accordingly, this pressure change can be measured to confirm the heat lysis process.

In a further embodiment, there is provided a heater configuration to allow heat lysis of targets of different sizes trapped on filters in cartridges configured to accept samples. In one embodiment, a user may desire to test for the presence of multiple organisms such as *Chlamydia trachomatis, Neisseria gonorrhoeae* and *Trichomonas vaginalis* from a single sample. Such a configuration would require all of these organisms to be trapped on the filter and lysed using heat, if heat lysis was the desired lysis method. Different targets or organisms differ in size, such that filters of different pore sizes would be required; in addition, different targets or organisms can have different optimal temperatures required for heat lysis. In one embodiment, there is provided metallic grid discs that can have filters of different pore sizes. Grid discs can be layered in a columnar structure and the swab sample would be filtered through them. The grid discs can be made of a sufficiently conductive material such that direct heat can be applied to the metal grid discs in order to lyse the cells trapped on the filters above the discs. Since heat can be applied to the grid individually, the temperature can be set to one that would be optimal to lyse the target or organism trapped on the filter over that particular grid.

In yet a further embodiment, there is provided an alternative configuration intended to provide fluid control in the reaction chamber(s) during heat cycling. During heat cycling, liquid can escape from inlet and outlet openings, particularly in an open system. This circumstance can allow the escape of potentially essential molecules from the reaction mix, resulting in a reduction of reaction efficiency, and can also potentially contribute to contamination of the system.

Figure 36A:
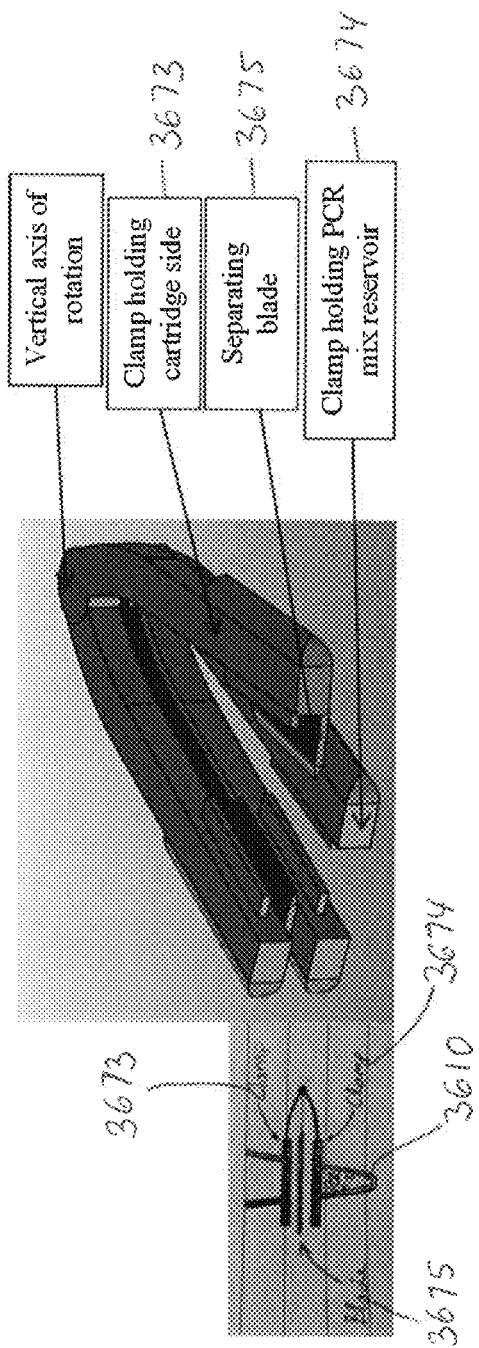
FIG. 36A demonstrates separation of the PCR mix from the cartridge body achieved by a clamping mechanism.
Figure 36B:
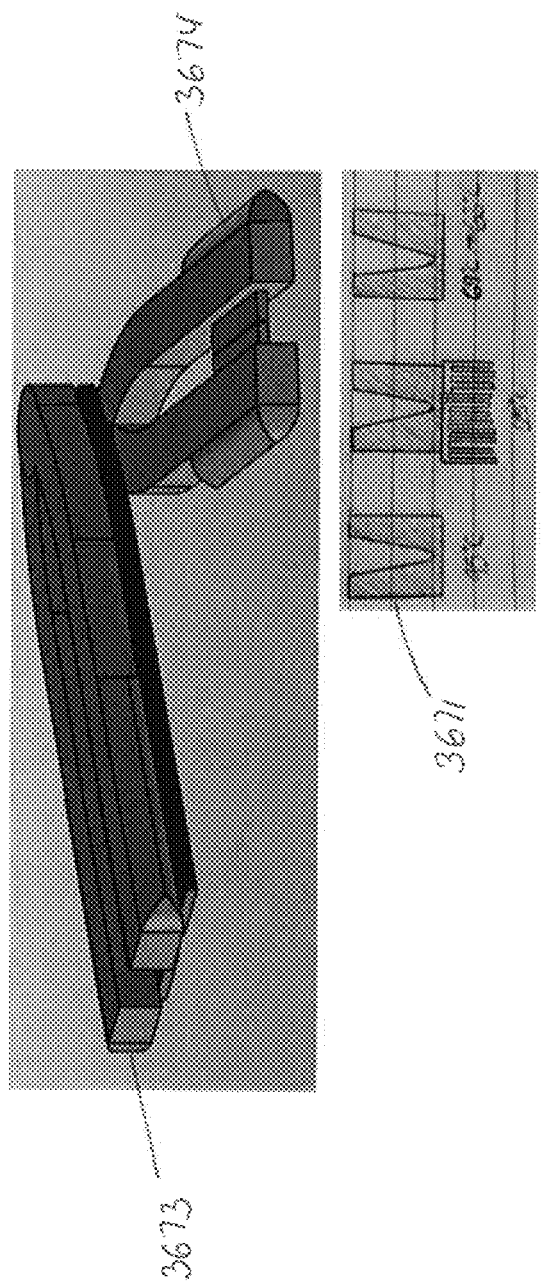
FIG. 36B demonstrates a bottom damper that contains the PCR mix and rotates about a vertical axis to heat blocks of different temperatures.

In one embodiment, there is provided a closed system following aliquoting of the desired lysate volume into the reaction chamber(s). While such a process could be attained through closing of several inlet and outlet ports, an entirely closed system can alternatively be generated through clamping and separation of the reaction chamber from the cartridge body. Upon this separation, rotational motion about the vertical axis could be generated to move the clamped reaction chamber to independently heated blocks to perform mechanically attained heat cycling, as shown in FIG. 36A, as an alternative to heat cycling using a stationary heater such as a Peltier. FIG. 36A provides a cartridge clamp 3673, a reaction chamber clamp 3674, and a separating blade 3675. In use, the cartridge clamp 3674 attaches the assembly to the cartridge, while the reaction chamber clamp 3674 holds the reaction chamber 3610. The separating blade 3675 closes off the reaction chamber 3610 from the cartridge. In one embodiment shown in FIG. 36B, where the desired reaction is a PCR reaction, there can be three independent heat blocks 3671 which would reach pre-set temperatures of 95° C., 25° C., and 69° C. through use of heater sources such as resistive heaters which would not require heavy processing or power consumption. In one embodiment, the heat sources can reach set temperatures during offline time such as during sample preparation or lysis to ultimately reduce the time of the workflow. Another benefit to constructing such a system includes the ability to readily change the reaction chamber, for example from a traditional PCR tube to a thin capillary tube or a deformable blister holding the, for example, 20 uL reaction mix for heat cycling. The clamping system could allow movement and contact of the reaction chamber to these heated blocks, while ensuring a tight seal. In a further embodiment, the heat cycling workflow would rotating the reaction chamber in the reaction chamber clamp 3674 into contact with the 95° C. block 3671 for rapid heating, rotating the reaction chamber clamp 3674 into contact with a block 3671 actively cooled to room temperature to quickly reach a desired annealing temperature, and rotating the reaction chamber clamp 3674 into contact with a block 3671 set to an annealing temperature of 63-69° C. Rotational actuators on the damper's vertical axis would ensure a seal and quick movement of the reaction chamber 3610, can also include sampling of fluorescence for instances of real time PCR.

In another embodiment of the present disclosure, there is provided a detection unit that can be used to detect the target of interest. In some embodiments, the target of interest will be bacteria, a virus, fungi or yeast containing genetic material. In some embodiments, the target of interest will release DNA or nucleic acids upon lysing, which can be processed downstream for analysis, which analysis can be analyzed following detection of emissions, such as fluorescence. For a fluorescence detection system, an excitation source (including, for example, an LED or laser, appropriate filters, and lenses) and an emission detection means (including, for example, a detector such as a photodiode, appropriate filters, and lenses) will also be included.

In one embodiment, there is provided an excitation and detection system intended to provide excitation of a sample in at least one reaction chamber(s), wherein excitation of the sample is provided using at least two colors of light, and wherein the reaction chamber(s) are visible through optical ports in heater walls. In one embodiment, the reaction chamber(s) can be a 100 uL PCR tube containing about 1-50 µL or reaction fluid, or about 1-25 µL of reaction fluid, or about 20 µL of reaction fluid. In another embodiment, there is provided an excitation system having the layout in FIG.

Figure 45B:
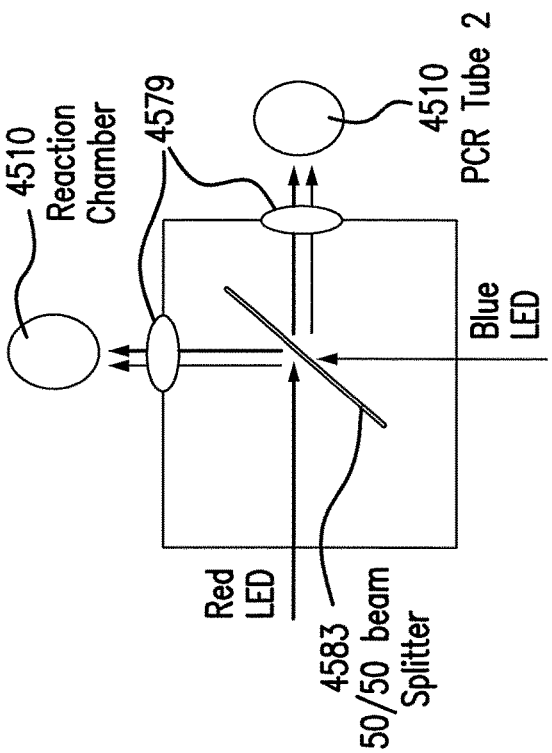
FIG. 45B demonstrates a layout for LED illuminator with better symmetry for the instrument according to the present invention.
Figure 45A:
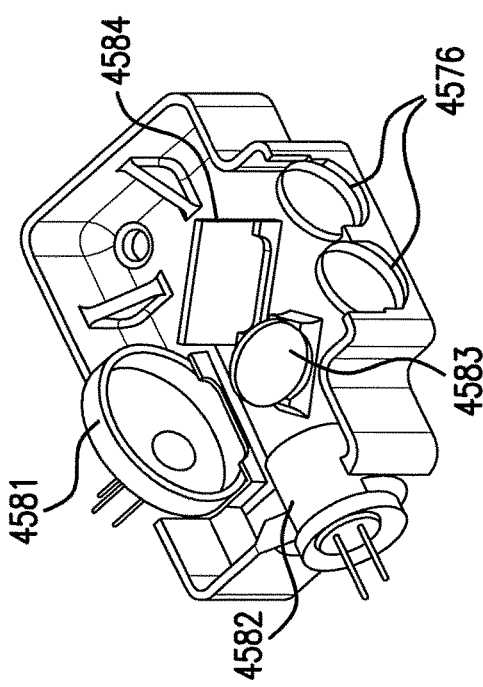
FIG. 45A demonstrates a layout of LED illuminator for the instrument according to the present invention.

45A. Two LEDs, 4581, 4582 are positioned perpendicular to each other, such that each beam can pass through a single beam splitter 4583, such that a portion of each beam is sent through a first optical port 4576, while the second portion of each beam reflects off a mirror 4584 and is sent through a second optical port 4576. In another embodiment, the beam reflected by the mirror has longer travel distance so a longer focal length lens need to be used to match the spot size of the two beams. In one embodiment, the two optical ports 4576 are directed towards each of two reaction chambers. In another embodiment, the layout of FIG. 45A can be revised to change the alignment of the reaction chambers 4510 such that beams that are perpendicular to each other can reach each reaction chamber 4510. In a further embodiment, the mirror can be removed from the system so that when the two LEDs, 4581, 4582 are positioned perpendicular to each other, each beam can pass through a single beam splitter 4583, such that a portion of each beam is sent through a first optical port 4576, while the second portion of each beam is sent through a second optical port 4576, wherein the first and second optical ports 4576 are perpendicular to each other.

Figure 45C:
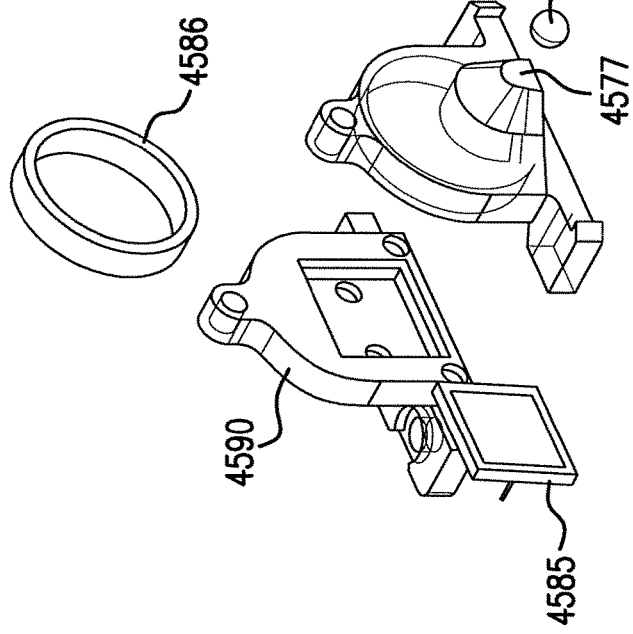
FIG. 45C demonstrates a detector box for the instrument according to the present invention.

In another embodiment, there is provided a detection system as depicted in the exploded view provided in FIG. 45C. A photodiode 4585 and a bandpass filter 4586 can be held by two holders 4590, having an optical port 4577 containing a ball lens 4587. The detection system can be arranged opposite an optical port on a heat block surrounding the reaction chamber in order to capture optical emissions from the reaction occurring within the reaction chamber. In one embodiment, the photodiode 485 can be a large area photodiode. In another embodiment, the ball lens can be a plano-convex or double convex lens. In one embodiment, the ball lens is a plano-convex lens.

Figure 45D:
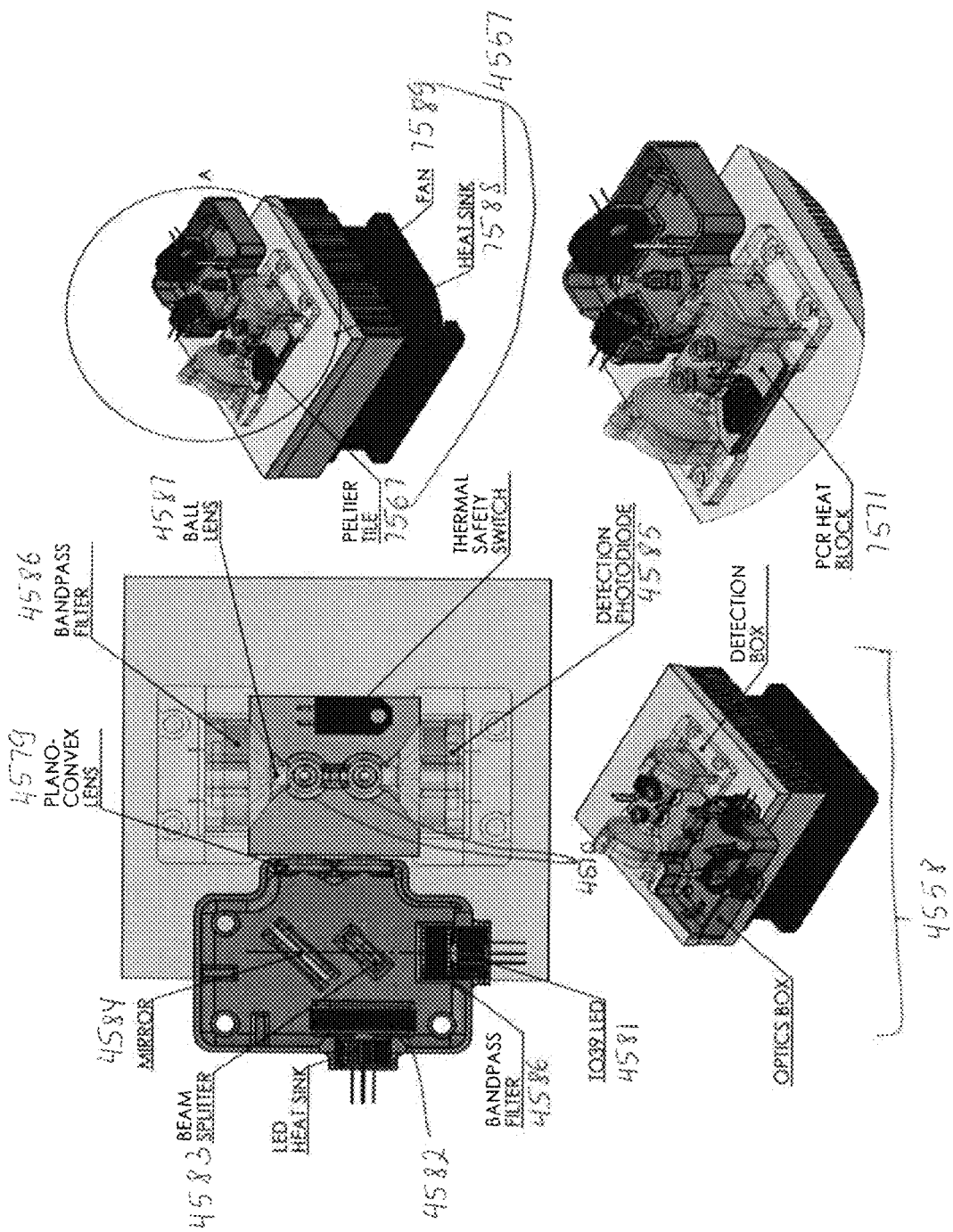
FIG. 45D demonstrates an optics system layout for the instrument according to the present invention.

In a further embodiment, there is provided an overall layout of the optical system 4558 with respect to the second heating unit 4557 for the device as shown in FIG. 45D. The optics system uses the layout described in FIG. 45A, however the layout in FIG. 45B, or any other layout devised in accordance with the positioning of the reaction chambers can be used. In one embodiment, two LEDs, 4581, 4582 are positioned perpendicular to each other, such that each beam can pass through a single beam splitter 4583, such that a portion of each beam is sent through a first optical port 4576, while the second portion of each beam reflects off a mirror 4584 and is sent through a second optical port 4576, wherein the first and second optical ports 4576 are positioned next to each other. The optical ports 4576 are directed at reaction chambers 4510, while two detector boxes having the layout provided in FIG. 45C are provided on either side of the reaction chambers, such that the detector boxes are perpendicular to excitation system. Each detection box includes a photodiode 4585 and a bandpass filter 4586 can be held by two holders 4590, having an optical port 4577 containing a ball lens 4587, wherein the optical port 4577 is directed at the reaction chamber 4510 perpendicular to the optical port from the excitation system.

The optics system 4558 is configured to interface with second heating unit 4557 as shown in FIG. 45D. The optics box and detection box can be situated on top of a heat sink 7588, while a heater 7567, which can be a peltier in one embodiment, can sit between the two detector boxes under the heat block 7571.

In one embodiment, the two color LEDs can be turned on in sequence so two different optical signals can be detected. In one embodiment, the fluorescence from two different dyes can be identified. The photodetection can take an extended time in order to obtain a better signal to noise ratio. AC driving can be used for LED so the fluorescence can be marked with a certain frequency, allowing narrow band detection to improve the signal to noise ratio. In a further embodiment, AC driving can also help differentiate fluorescence signals of different wavelength by driving different excitation LED at different frequencies. In another embodiment, the heat block 7571, which can also serve as holders for the reaction chamber(s), can be made to be highly reflective so that fluorescence signal can be enhanced.

In one embodiment of the present invention there is provided means of providing optical detection of emissions from the reaction chamber(s) while heating of the chamber, including heat cycling or temperature ramping, is occurring. As shown in FIG. 37A, in one embodiment a heat block 3771 can be provided having two optical ports (for example, one for fluorescence excitation 3776 and one for detection 3777) per reaction chamber heater. These optical ports 3776, 3777 allow the optical system access to the reaction chamber directly through the heat block. In one embodiment, the heat block can be made from a conductive material for example, such as silver, aluminum (e.g., Al 6063), or copper (e.g., C101 OFE). FIG. 37B provides side and cross-sectional views of the heat block 3771 having an excitation optical port 3776 and an emission optical port 3777. As shown, in one example the heat block 3771 can also contain a recess or hole 3778 for placement of a temperature sensor. A temperature sensor can be used to provide thermal control for reactions such as amplification reactions. In one embodiment, feedback for thermal control can be achieved by putting a thermal sensor in close proximity to the samples of interest. The sensor can be adhered to the topside of the heat block using epoxy, silicon, copper or aluminum tape, or other adhesives known in the art. Alternatively, the sensor can be embedded into the heat block at a sensor hole 3778, wherein the sensor can be a thermistor, thermocouple, or RTD, for example. In one embodiment, the sensor hole is located at a height similar to the sample of interest. In some embodiments, the heat diffusion time between the sensor and the samples are matched by appropriately tuning the distance and thermal conductivities of the materials.

Figure 38:
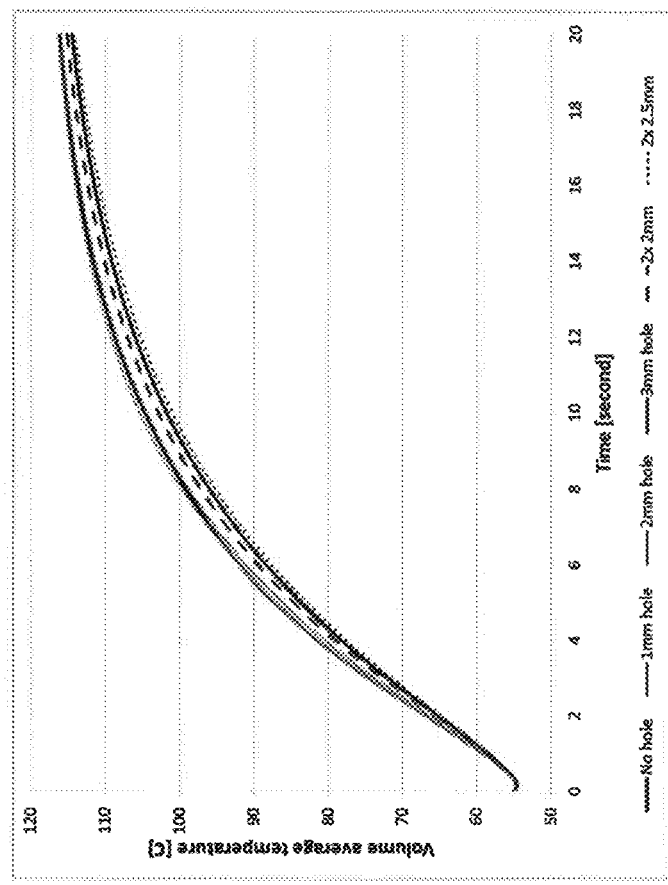
FIG. 38 demonstrates a COMSOL simulation results showing temperature response for various hole sizes.
Figure 39:
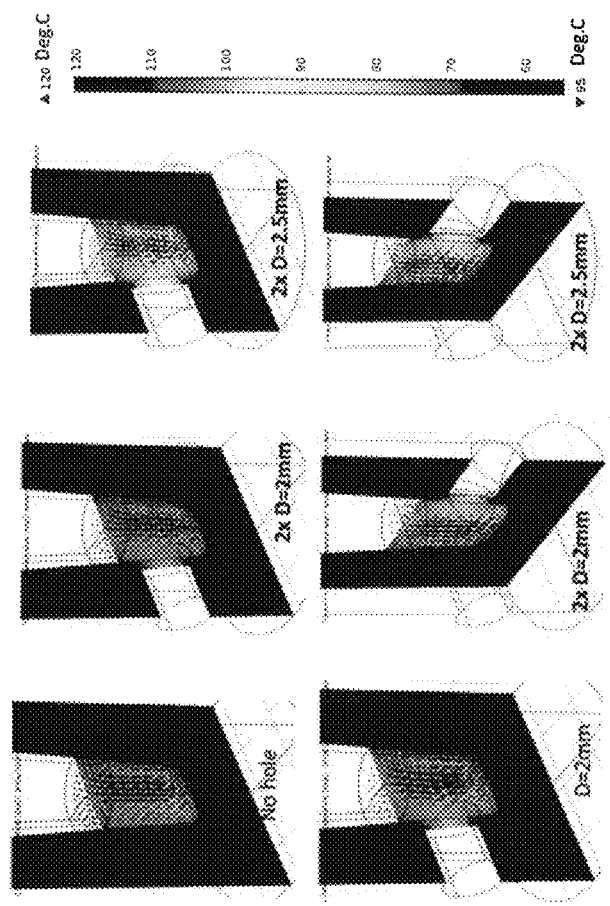
FIG. 39 demonstrates temperature and velocity distribution.

In one embodiment, it is a facet of the present disclosure that keeping the optical ports small in size can mitigate the adverse impact on thermal uniformity of the liquid sample within the reaction chamber. FIG. 38 provides the result of a finite element COMOSL simulation of a temperature step showing temperature response for various size optical ports. For a single optical port, a size of 2 mm or smaller causes a negligible impact on response time. Larger optical ports (e.g., a single 3 mm hole or two 2.5 mm holes) result in significant response lag as shown. One reason the optical ports can be tolerated from a thermal uniformity perspective is that natural convection, induced by the heated walls, substantially mixes the liquid within the reaction chamber, as shown in the temperature and velocity distributions shown in FIG. 39. Considering these effects, in one embodiment, the optical ports are in the range of 2.0-2.5 mm. This size is sufficient to efficiently excite and collect fluorescence from small volume samples (e.g., 15-30 uL, for example, 20 uL). In some embodiments, the excitation and detection optical ports can be a different size (for example, there may be provided a larger detection port to collect more fluorescence when excess excitation intensity is available).

In one embodiment, in addition to considering the size of the optical ports, various other parameters controlled to ensure rapid thermal cycling is possible, thereby optimizing thermal reactions. For example, it is within the scope of the present disclosure that the base of the heat sink can be thin enough to reduce thermal mass but sufficiently thick to ensure good heat spreading. In one embodiment, the base thickness can be in the range 1 to 5 mm, or from 1-3 mm, or about 2 mm. In embodiments where the base is very conductive, enough thickness is still required to ensure a manufacturable flat surface, so that the heat block can be attached to a rigid heater (e.g., Peltier or ceramic heater).

Similarly, in another embodiment, the wall thickness of the reaction chamber holders within the heat block should also be kept thin. In one embodiment, thin walls both reduce thermal mass and improves optical efficiency. The wall thickness should be in the range 0.5 to 5 mm, or from 0.5 to 3 mm, or about 1 mm.

In one embodiment, the optical ports can allow for automated filling of the microtubes from above since the optical system has been designed to providing imaging through the heat block.

In one embodiment, there is provided a heat block for providing heat to an amplification vessel which features two or more optical ports in which at least one of said ports is used to excite a fluorescent dye housed within said vessel and at least one of said ports is used to detect the fluorescence generated by said dye. The optical ports can be between 1 and 3 mm, or can be 2 mm. The optical ports can be a different size, such that the detection port is larger than the excitation port. Materials for the heat block can include aluminum, silver, copper, or an alloying comprising one of those metals. In some cases, the heat block can have a reflective interior, a light absorbing coating, or an anodized interior. Alternatively, the heat block can have a light coating behind the excitation port, but otherwise is reflective.

In some embodiments, optical ports are chamfered. Optical ports can be oriented at 90 degrees to each other or can have the excitation port below the detection port. Detection can also occur through the top of the amplification vessel. The optical port can be filled with a high refractive index material.

The heat block can also include a temperature sensor in or on said heating block, including a thermistor, thermocouple, or RTD. If a temperature sensor is used, it can be positioned at a thermally equivalent distance as the contents of the vessel.

In another embodiment of the present disclosure, optical signal enhancement is desired. In one embodiment, single enhancement can be obtained by using microperforated heat blocks instead of a small number of optical ports. In one embodiment, microperforation can be provided by an array of microholes or a specific area of microperforation. In this embodiment, relatively thin heater walls are beneficial for good light transmission in both ways.

Microperforation methods exist in the art. For instance, U.S. Pat. No. 8,303,151 relates to invisible buttons using microperforation with tailored hole profiles to control light behavior, U.S. Pat. No. 8,481,887 describes a method for machining tapered micro holes, and U.S. Pat. No. 7,086,666 describes an identification card with embedded halftone image security feature perceptible in transmitted light.

Figure 40:
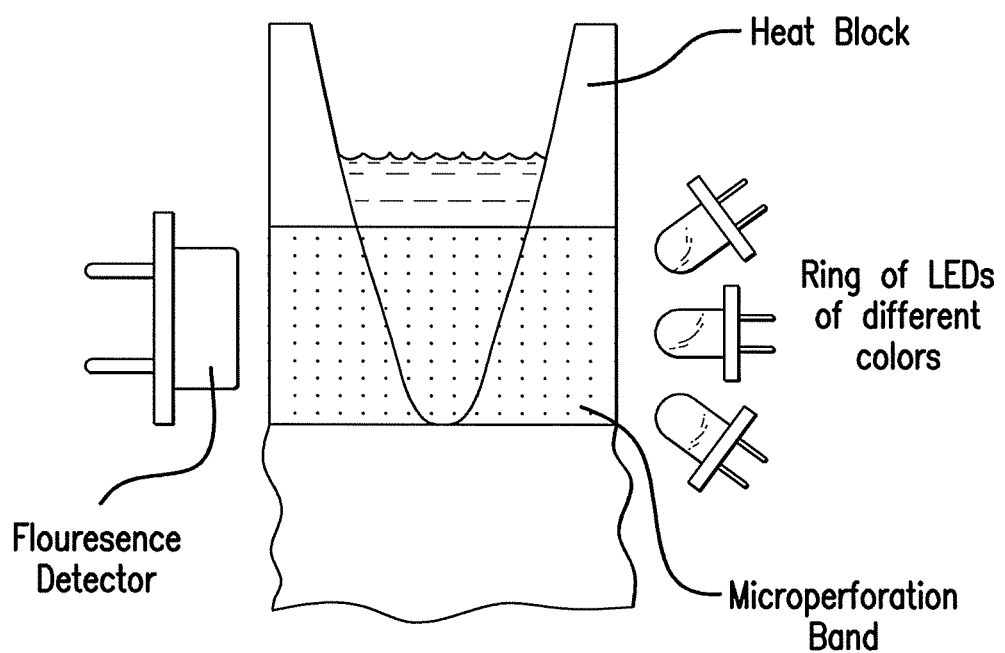
FIG. 40 demonstrates a heat block with a band of microperferation for imaging.

It is therefore an embodiment of the present invention to use methods known to those of skill in the art to fabricate regions of microperforation on heater components such as heat blocks, for example, by using large numbers (for example, hundreds or thousands) of sub-millimeter holes machined into the material or metal. As depicted in FIG. 40, a zone or band of microperforation can be provided on a heat block in the area that allows the optical system to detect emissions from the reaction chamber. This can be accomplished through conventional laser techniques for small hole drilling. If the heater's walls are thin, illumination light can reach the sample within the reaction chamber, and fluorescence from the reaction chamber can be detected through the microperforated regions. Techniques also exist that can be incorporated into some embodiments for shaping the hole profile and adding light guiding optics for improved light transmittance and acceptable viewing angle, so that regions of the heat block can be optimized for illumination or detection.

In one embodiment of the present disclosure, microperforation of heater components, including but not limited to heat blocks can be used to detect marker dyes or other indicators in real-time during reactions, such as during PCR cycles by looking through the heating structures. In another embodiment, use of microperforation can help reduce instrument size by allowing overlapping thermal and optical systems. Microperforation can additionally improve heating uniformity for more consistent biochemical behavior, improve optical performance by tailoring hole profile (taper shape), increase light transmittance and increase allowable viewing angle to improve tolerance to misalignment.

In another embodiment, chamfering can be included to provide more light into or out of the ports. The chamfering can allow for an optically larger hole, while maintaining the conductive material near the microtube to ensure rapid and uniform heating. When used with an LED, the angle of the excitation port chamfering can be designed to match or be slightly larger than the LED cone angle, as illustrated in FIG. 41. As shown in FIGS. 41a and 41b, the LED cone angle (q) can be calculated from hl, L, d and D. In another embodiment, the chamfering angle of the detection port can match the viewing angle from the port to the light collection lens.

In one embodiment, the angular orientation of the excitation and detection ports can be adjusted to minimize background signal for fluorescence applications. For example, detection ports should not be in line with an LED excitation port to avoid LED light getting into the detector directly. In one embodiment, the excitation and detection ports are most preferably oriented at a 90° angle, as shown in FIG. 37A-B.

In another embodiment, high refraction index fillers can be used in the ports to increase light collection/emission efficiency. In those configurations where fluorescence is the optical property detected from the reaction chamber, the fluorescence from the fluid in the reaction chamber is a wide angle emission. The air in the port can be replaced with high refractive index materials, such that the angle of fluorescence entering the port can be smaller so that more light can exit the port and have a chance to be collected by the detector. As depicted in FIG. 41B(a), a point source emitting through a port on an opaque wall has the depicted angle of the cone of light that can exit the port. FIG. 41B(b) depicts the same port and point source as in (a), however the port is filled with high refractive transparent materials (such as glass, optical polymers, et al), thereby altering the angle of the cone of exiting light, showing that more light can exit the port when the port is filled with higher refractive index materials.

In a further embodiment, the interior of heating components, such a heat block, that are in the area of detection can be made from a reflective material to enhance excitation and collection efficiency. Alternatively, in another embodiment, the inside of the heating components, such as a heat block, could be made using non-reflective material (e.g., black anodized) to prevent background light caused by scattering of the excitation light.

In yet another embodiment, there is provided a combination of materials within the interior of heating components such as a heat block, wherein side wall facing the excitation port can be made black in an area the size of the cone of excitation light entering the port, and the port itself can be made black, while the remainder of the inside walls of the heat block are made reflective. In this manner, the excitation light that enters the port but is not used for excitation with the reaction chamber will be absorbed by the black walls, thus minimizing the scattering of the excitation light. At the same time, the reflective surface still enhances emission collection efficiency.

In another embodiment, the excitation port can be located below the detection port so that the parabolic shape of the tube can be utilized to collect reflected excitation light.

In a further embodiment, there is provided a heat block having a small amount of material added to the optical exit port designed to fit a small convex lens. This convex lens can be used to focus the light being detected into the center light sampling components (e.g. band pass filter and photodiode). In another embodiment, there is provided a heat block that has a flat bottom base in contact with a heater, for example, a Peltier for efficient heat transfer. In a further embodiment, there is provided reaction chamber cutouts 4280 of nominal dimension added to a reaction chamber of known outer geometry. There is additionally provided a pathway for light to enter each reaction chamber through side cutouts of known size and an alternate pathway for light to exit a receptacle through side cutouts of known size. In a further embodiment, a small lens mounting feature can be added to each optical port for the mounting of a small convex lens.

Figure 42A:
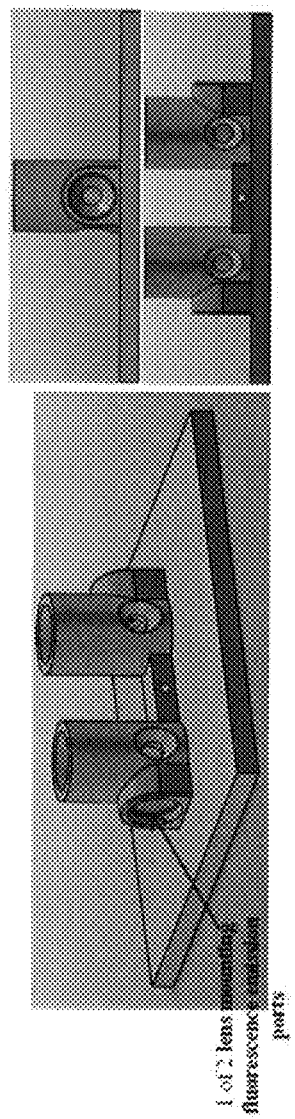
FIG. 42A shows a new design of a heat block assembly which includes an additional lens mounting feature (3D view on the left and side views on the right).
Figure 42B:
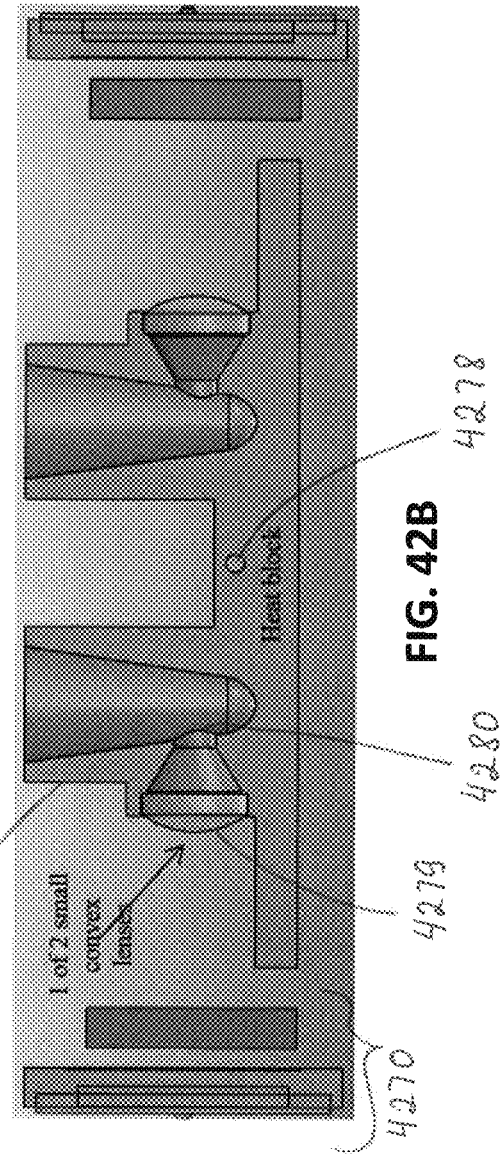
FIG. 42B shows a section view of the heat block assembly containing small convex lenses within the heat block and includes two detection components on each side for visual reference.

FIG. 42A provides a heat block 4271 which includes the additional lens mounting feature. Further, FIG. 42B provides a section view of the assembly containing the small convex lenses 4279 within the heat block 4271, and includes two detection components 4270 on each side for visual reference. In one embodiment, the lenses 4279 can be glued, press-fit, fixed with a pin, or attached with any other method known to those of skill in the art. Other lens types and optical components (e.g., filters, beamsplitters, etc.) can also be integrated in a similar fashion as will be appreciated by those of skill in the art.

Figure 43:
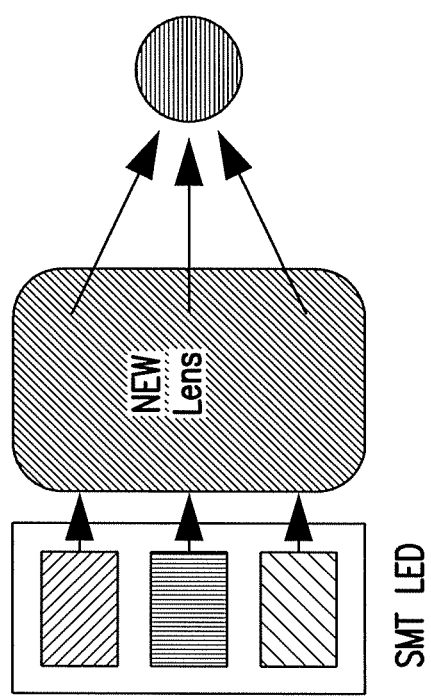
FIG. 43 demonstrates a focusing multicolor LED lens.

In another embodiment, in order to allow detection of more targets during a single reaction process, for example, an amplification process such as PCR, a multicolor LED source can be used instead of two or more LED sources. In another embodiment, a lens can be placed over a surface mount LED source such that the lens would focus each individual color to a single spot, thereby mitigating the inherent property of an LED source that the cone of emitted light is usually very large (for example, >50°). In some embodiments, the lens can be made of any suitable material known to those in the art, for example, plastics. As shown in FIG. 43, in another embodiment, addition of the lens to an LED source can allow allow specific color wavelengths to be utilized across the color spectrum as placement of the lens over the LED source will align each color to the same spot.

Figure 44:
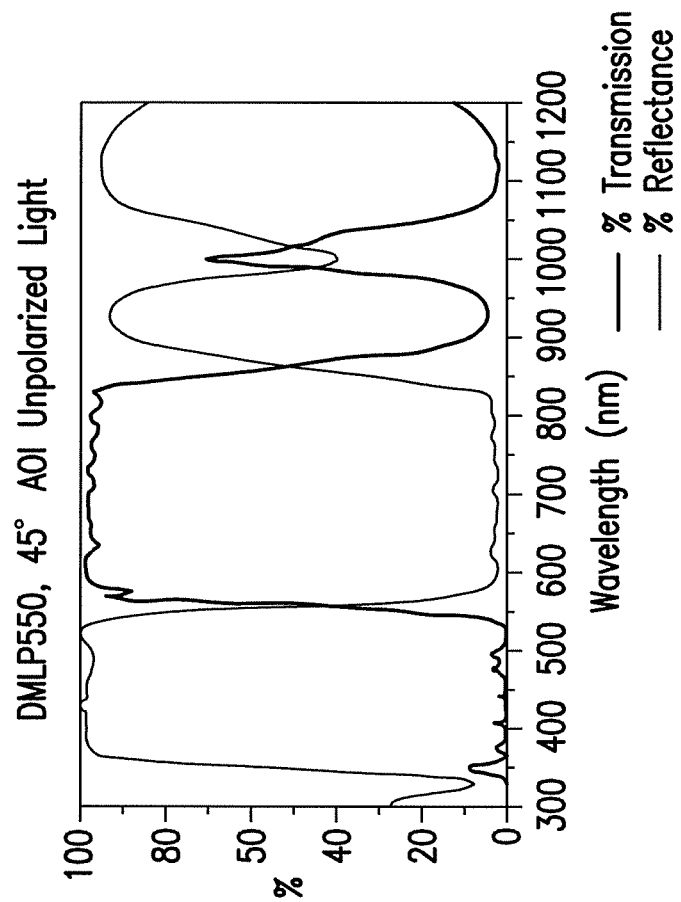
FIG. 44 shows separation of wavelengths of 350 nm-550 nm and 550 nm-825 nm.

In yet another embodiment, the detection unit can include the use of a chromatic beam splitter to filter the light by color in order for easier optical processing instead of requiring additional optical processing such as filters. In one embodiment, a dual band pass filter can then be used. In some embodiments, the ability to split the light into more colors be required or desired, such that another band pass filter region can be added in the emission filter. By separating the colors, the chromatic beam splitter "sorts" or "filters" the light into other bins, which can be filtered using less expensive single/dual band pass filter elements. In one embodiment, other photodiode sensors can be added. As shown in FIG. 44, in one embodiment a dichroic beam splitter separates between low and high wavelengths, for instance between 350 nm-550 nm and between 550 nm-825 nm.

In a further embodiment, a trichromic beam splitter can be used to separate the emission light by color from a sample undergoing a reaction, for example, PCR. This passive element can split the incoming beam into an RGB spectrum for further processing. In another embodiment, the use of a chromatic beam splitter and a band pass filter can be expanded for use with higher order prisms such as those with 4 or 5 colors.

In yet another embodiment, a configuration is provided to allow for optical detection to occur while account for fluctuating LED emissions during the period of time necessary for an LED to settle down. In one embodiment, a photodiode can be added to measure the LED power from leaked light. In another embodiment, the location of the photodiode can be determined based on the specific design of the optical system. In a further embodiment, the photodiode can measure the LED power constantly or alternately in a synchronized manner with optical detection or measurements. In one embodiment, the optical detection can be fluorescence measurements. Fluorescence measurement results can therefore be adjusted based on the measured LED power even though the LED output fluctuates, such that the fluorescence measurement will not be affected. In another embodiment, the drift seen in LED power during the warm up period can also be compensated for by monitoring the LED power. In a further embodiment, when LEDs are pulsed, monitoring LED power can further compensate LED amplitude fluctuation and possible pulse width inaccuracy.

In another embodiment, there is provided an alternate configuration having a microlens provided on the optical ports of the heat block to provide increased signal detection. Any suitable microlens known in the art can be used in the practice of this embodiment. In one embodiment, there can be provided an optical lens placed inside the optical port within the heat block, such that the lens is directed towards the reaction chamber. In another embodiment, the microlens can focus the excitation light into the reaction chamber and collect the emitted light while directing it through the optical port and to the detector.

Figure 46:
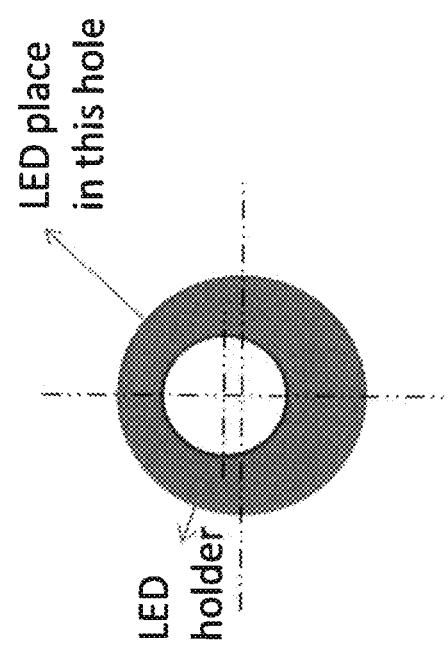
FIG. 46 demonstrates a LED holder.

In another embodiment, there is provided an LED mount with optical aligning capabilities. Different LEDs can have slight differences in the position of dies and lenses resulting in different emitting beam directions and image locations, which can result in some of the LEDs not pointing to the optical ports sufficiently. In one embodiment, the LEDs are placed in LED holders, which is one embodiment can be a heat sink, that are configured to have a recess or hole placed off-center as shown in FIG. 46. The LED holder can be rotated up to 360 degrees when being placed, so that by virtue of the recess being off-center, the LED is accordingly placed in different locations by rotating the LED holder. In another embodiment, at the same time, LED can also rotate in the LED holder up to 360 degrees. By combining these two rotational movements, a large range of LED placements can be covered to provide better and more repeatable LED illumination. In another embodiment, the degree to which the recess or hole is off-center in the LED holder can be varied, such that a different LED holder having a different recess location can be selected depending on the properties of the individual LED being placed.

In one embodiment of the present disclosure as shown in FIG. 47A-B, there is provided a configuration to allow the use of optical fiber or light guide to excite fluorescence or detect emissions from the reaction chambers. In one embodiment, optical fiber 4791 can be inserted into the current fluorescence emission holes 4777 on the heat block 4771, such that the cleaved end of the fiber should be at proximity of the reaction chamber. In one embodiment, the diameter of the optical fiber can be selected to match the size of the optical ports. In one non-limiting example, fiber of ~1 mm to ~5 mm, or around ~2 mm in diameter can be used in practice of the present disclosure.

In another embodiment, a lens can be built into the optical emission port 4777. In one embodiment, a short focal length lens can be used, for example, a ball or semi-sphere lens. When a lens is used within the optical port 4777, the fiber 4791 can be prevented from coming in direct contact with the heat source, for instance, the heat block 4777. One advantage of the present embodiment is that a wider choice of fibers will be available as the user is not limited by the working temperature range of the fibers.

In one embodiment, the optical fiber 4791 can be supported or fixed with extra mechanical structures. In another embodiment, a fiber holder 4793 can be used which has the ability to move in at least one direction in order to better align the fiber with the optical port 4777 or lens 4787. In a further embodiment, the fiber holder 4793 can move in more than one direction, such as, for example, in two or three directions.

The optical fiber can be glued to the ports or an adaptor 4792 can be used that can be mounted to the heat block or screw in the fluorescence emission ports. In one embodiment, the adapter 4791 can be a screw-in adaptor, or can be otherwise fixed in place, including by using adhesives.

In one embodiment, regardless of the configuration used locate the optical fiber 4791 with respect to the optical port 4777 or lens 4787, fiber 4791 guides the emissions to sensors. In one case, the emissions can be fluorescence. In another embodiment, the sensor can be a photodiode. In a further embodiment, the photodiode can be placed at a location remote from the reaction chamber and therefore separated by distance from the heat sources.

In one embodiment, the optical device configuration can include one fiber for each reaction chamber. In another embodiment, the optical emissions, for example, fluorescence, can be collected via the optical emission ports. In some embodiments, particularly if an enhanced signal is desired or if only fibers with small core size are available, multiple fibers can be used. In this embodiment, additional optical emission ports can be provided. In another embodiment, all the fibers collecting emissions from one reaction chamber are connected to one detector. In another embodiment, optical fibers from more than one reaction chamber can be connected to the same detector. In a further embodiment, if there is open space from the top or bottom of the reaction chamber, the optical fiber can also be used to collect emissions from those locations, providing flexibility to the configuration of the optical detection system.

In another embodiment, there is provided a multifunctional mounting block for thermocycling and emission detection that combines insulation, a heat source, and optical detection in a single unit. As provided in FIG. 48A, the detection assembly can be integrated within an insulation block. In one embodiment, this is done by eliminating the separate material for mounting the detection components 4870 (for example, a band pass filter 4886 and photodiode 4885) and creating a custom fitting on the insulation block.

By fusing the detection assembly 4870 with the insulation/clamping block of the system, the number of parts required within the system is reduced and better control the geometric placement of these optical components is provided. In one embodiment, the combined mounting block provides means for clamping down a heat block and a heat source, for example, a Peltier, to a heat sink. In another embodiment, the combined mounting block insulates the heat block and the heat source, for instance, a Peltier, from other surrounding components. In yet a further embodiment, the combined mounting block provides an optical pathway for excitation light entering a heat block and detection light escaping a heat block. In another embodiment, the combined mounting block provides a housing and fixture for optical components, for example, band-pass filters and active detection elements (e.g. a photodiode) in order to also serve as the detection assembly for the instrument.

Figure 48A:
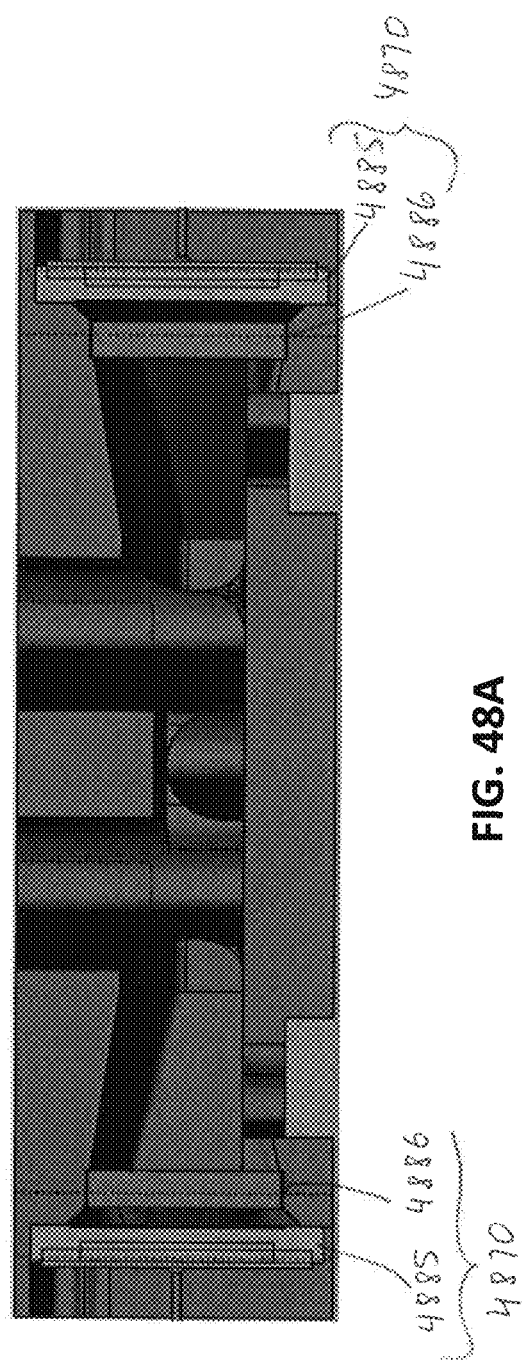
FIG. 48A demonstrates a section view showing a mounted filter and light detection element (photodiode) affixed to an insulation block directly (thermal block not shown).
Figure 48B:
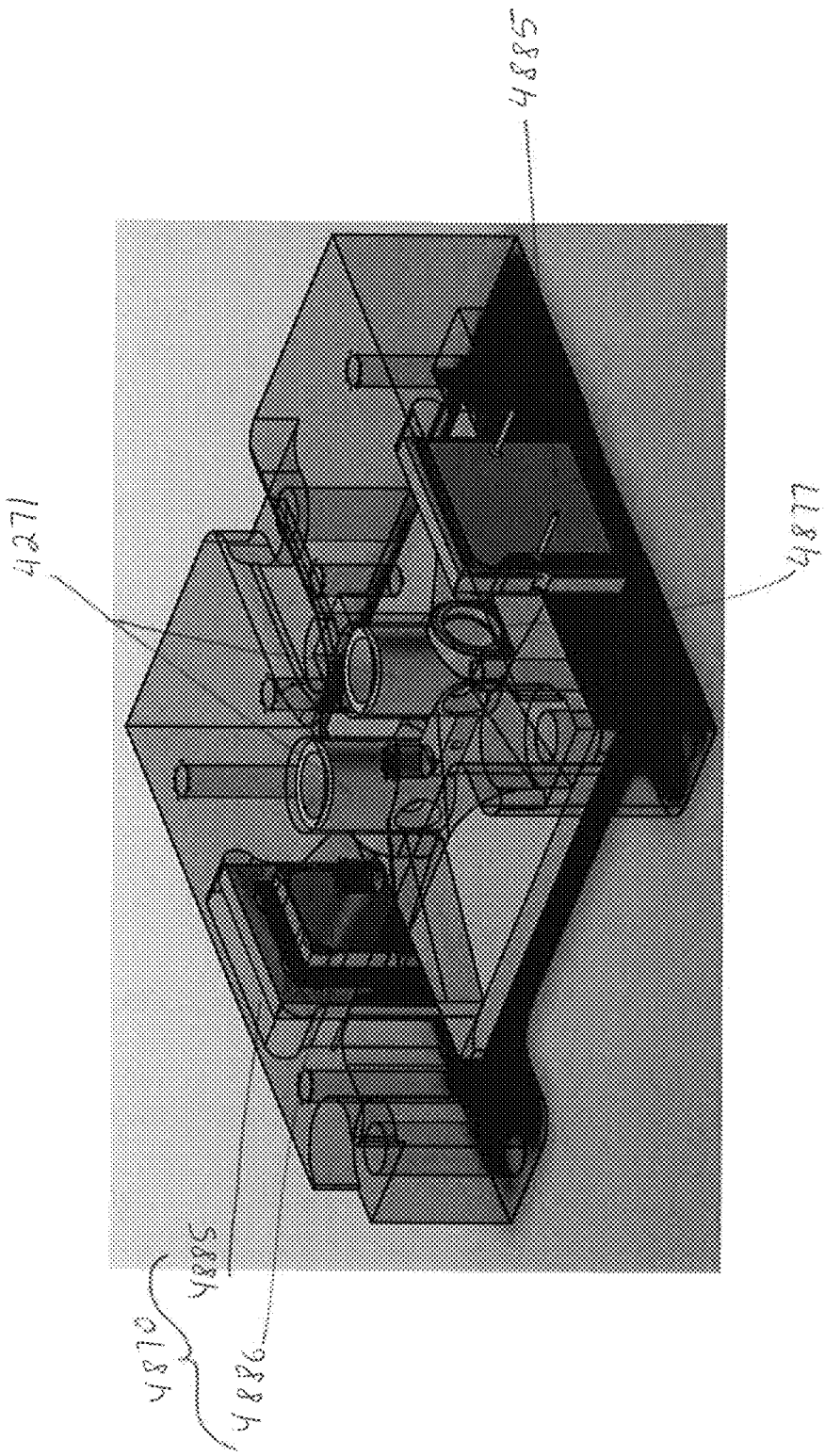
FIG. 48B demonstrates an assembly view showing optical components mounted to the insulation block as the insulation/clamping block bottom surface applies pressure to the thermal block's upper base.

As provided in FIG. 48A the mounted filter 4886 and light detection element 4885 (photodiode), which jointly make up the emission detection unit, can be affixed to the insulation block directly (thermal block not shown). Further, FIG. 48B shows the optical components mounted to the insulation block as the insulation/clamping block bottom surface applies pressure to the thermal block's upper base.

Figure 49:
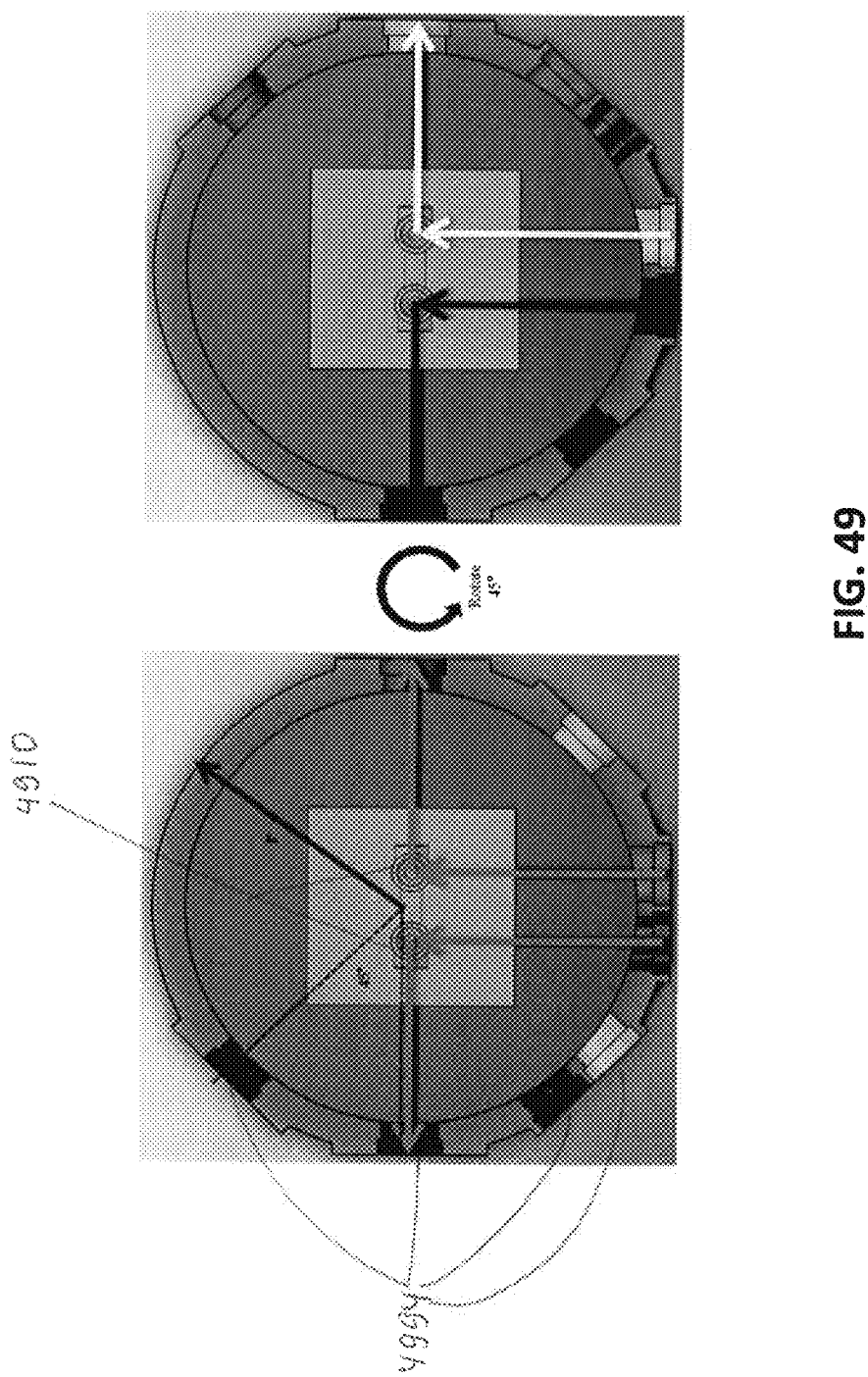
FIG. 49 demonstrates an optical model in relation to reaction tubes and a heat block. The dashed line represents the angle displacement (45°) of each filter mount. The solid black line represents the radius (r) of the optical block shown.

In a further embodiment, there is provided a configuration to allow the addition of more than two color channels. In one embodiment, FIG. 49 depicts side cutouts 4994 for each filter lens necessary to filter incoming excitation light, for example LED light, and to measure exiting emissions, for example, fluorescence from each reaction chamber. In another embodiment, the rotation of this optical unit by 45° would introduce a new set of filters to the optical system, allowing for a total of 4 independent optical paths in the example shown. As shown in FIG. 49, the optical model is depicted in relation to the reaction chambers 4910 and current heat block. Independent optical excitation and detection filters and light paths from a light source (for example, an LED) to a detection sensor (for example, a photodiode) are provided. The dashed line represents the angle displacement (45°) of each filter mount. The solid black line represents the radius (r) of the optical block shown. In another embodiment, the design provided in FIG. 49 could also be expanded further to include more filters. In another embodiment, the radius shown could be increased, and additional light guides from filters to each reaction vessel can be added to compensate for a potential signal loss from an increase in distance.

Figure 50A:
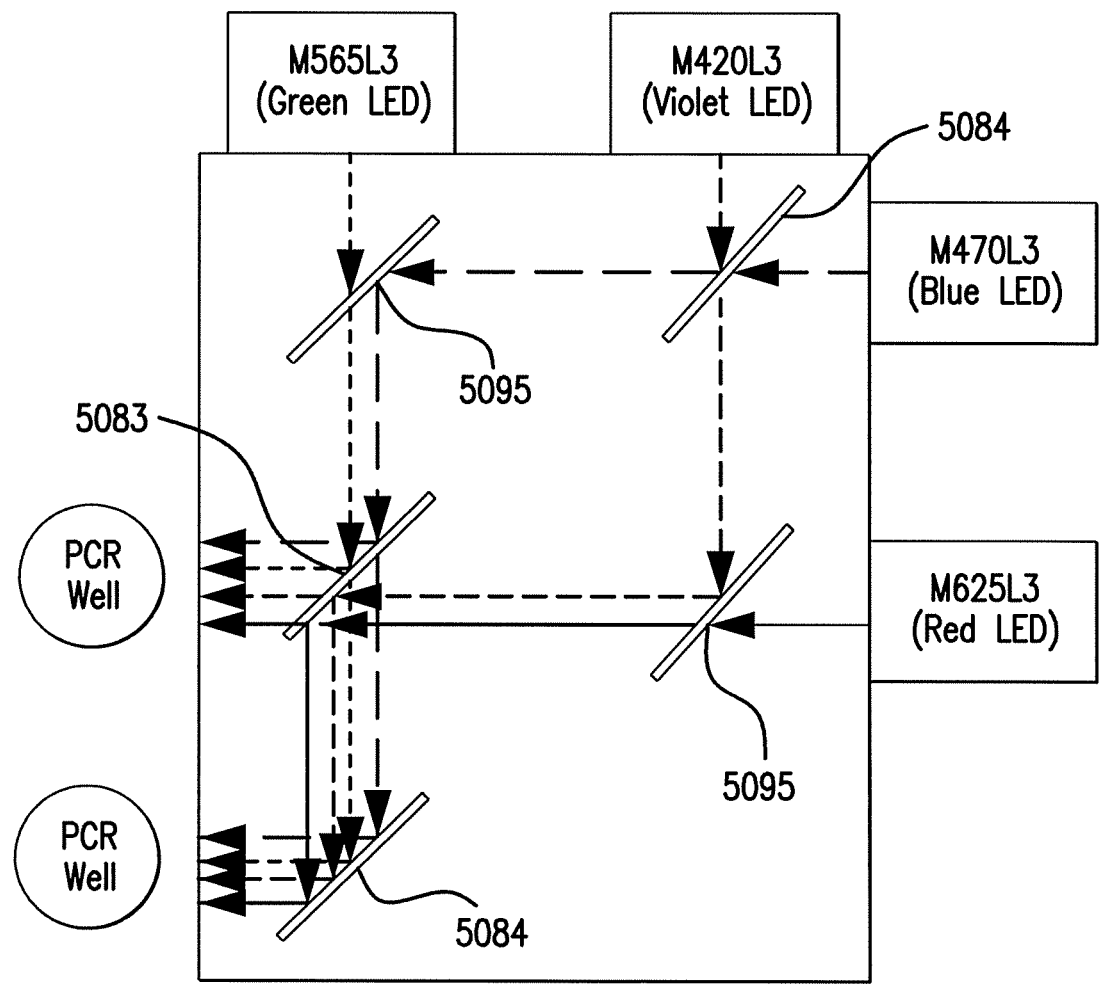
FIG. 50A demonstrates a 4-color excitation approach.

In another embodiment, a further configuration for allowing multiple color excitation can be accomplished via the use of dichroic elements. In one embodiment, the dichroic elements allow certain wavelengths of light to be reflected, while other wavelengths are transmitted. In another embodiment, four colors can be combined in this way and used to excite a reaction chamber. As shown in FIG. 50A is an example of a 4-color excitation approach using dichroic elements 5095. Lower wavelengths (such as the Blue LED) are reflected, while higher wavelengths (such as the Red LED) are transmitted. In one embodiment, by using a 50/50 beamsplitter 5083 and a mirror 5084, all 4 wavelengths can be transmitted to reaction chambers for excitation. In one embodiment, the size of this assembly is driven by excitation source diameter, for instance LED diameter, as well as diameter of the dichroic elements. Using custom cut filter and dichroic elements, this assembly can be brought down to a small footprint for use in a POC instrument.

Figure 50B:
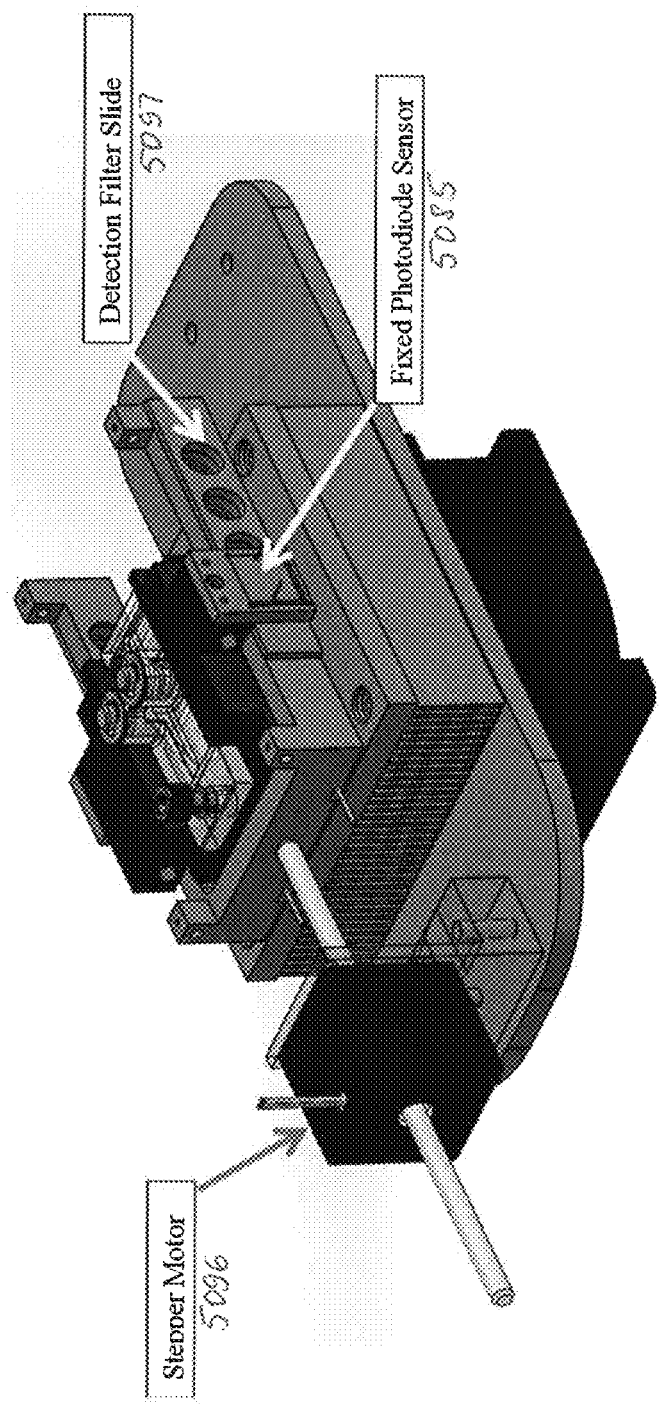
FIG. 50B demonstrates a detection system according to one embodiment of the present invention.

As shown in FIG. 50B, in one embodiment, for detection, a moving slide 5097 can be used to filter and detect for each color individually. A stepper motor 5096 can be used to actuate this slide, and keep the correct timing in regards to excitation. When a particular color is turned on to excite the PCR solution, the appropriate detection filter must be aligned with the detection port on the heat block. A fluorescence detector 5085, such as photodiode, is fixed in alignment with the detection port.

In a further embodiment, as shown in FIG. 51, several square heaters, for instance Peltier modules can be laid side by side to each other with small spacing to allow for optical detection through the gaps 5199. In another embodiment, a heater, for example a peltier, can be provided with hole cutouts 5198 to allow optical detection through the hole cutout 5198.

Spin Column Filtration

Figure 52:
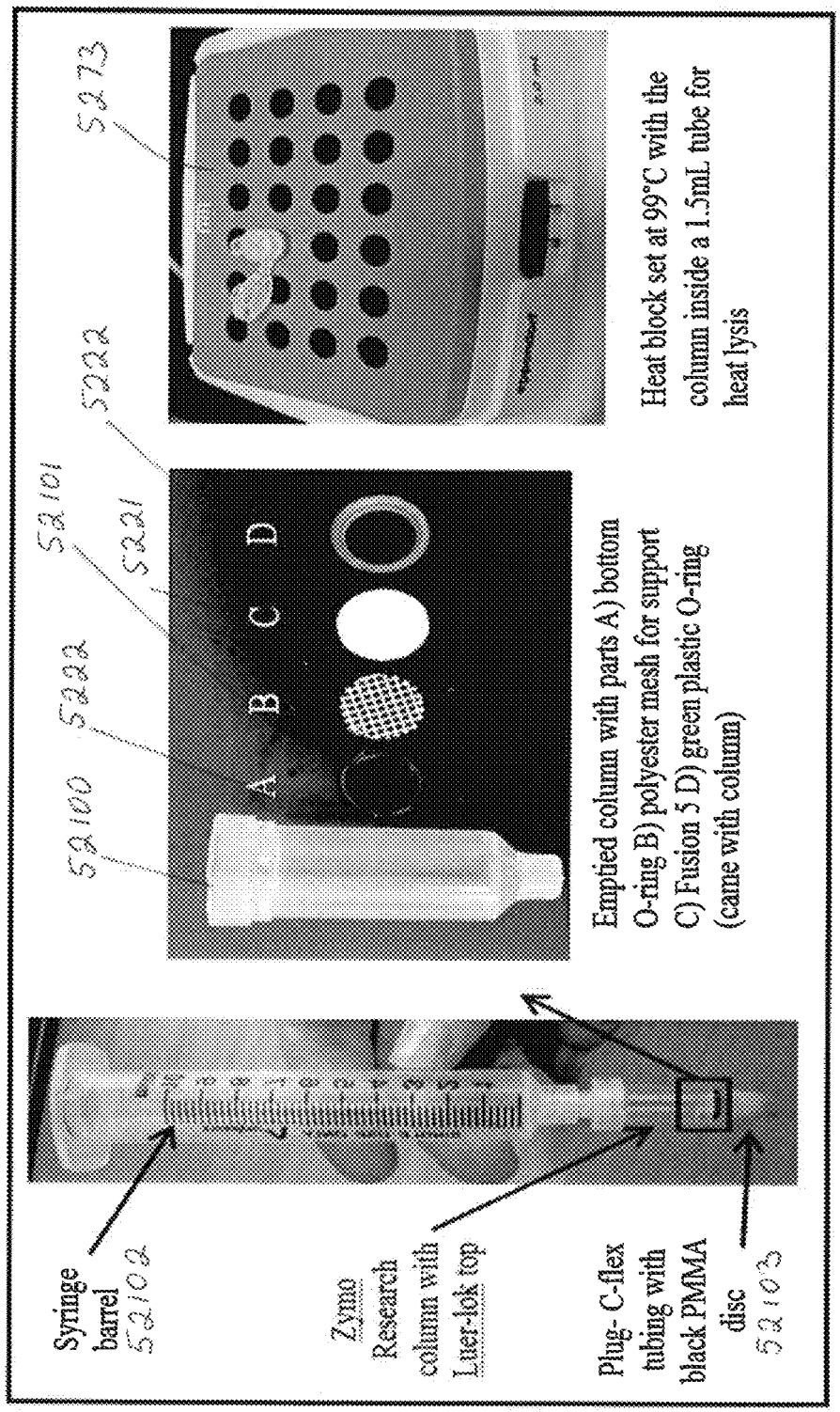
FIG. 52 demonstrates a spin column according to one embodiment of the present invention.

In yet another aspect of the present disclosure, some embodiments can comprise an assembly for quick bacterial concentration and crude heat lysis for an aqueous sample containing bacteria using a simple modified spin column. In one non-limiting embodiment, the aqueous sample can be a urine sample potentially containing a target of interest, for example, *trichomonas, chlamydia* and/or gonorrhea bacteria. As shown in FIG. 52, a spin column 52100 with a luer lock top can be fitted with a capture filter 5221, support mesh 52101, and sealing material 5222. In one embodiment, the spin column 52100 can be a Zymo Research Spin Column V; the capture filter 5221 can be GE Fusion V membrane that is 7 mm in diameter; and the sealing material 5222 can be an O-ring having 7 mm outside diameter (OD), 5 mm inside diameter (ID), and made of nitrile rubber Buna-N.

A disposable syringe 52102 can be attached to the column via a fitting. In one embodiment, the disposable syringe is a 10 mL syringe attached to the column via a luer fitting.

In one embodiment, the spin column 52100 can be plugged after filtering using a piece of Cole-Parmer C-flex tubing fitted with a PMMA disk inserted into one end of the tubing. By way of example and without limitation, the C-flex tubing can have 0.11" ID, 0.186"OD, and be 5 mm long); the Poly(methyl methacrylate) (PMMA) disk can be 3 mm thick and 4 mm diameter.

In one embodiment, a procedure for using the spin column 52100 can be as follows:

1. The filter 5221 is "pre-wet" with water in order to reduce diffusion of urine inhibitors into the membrane which can be released during heat lysis and cause PCR inhibition.

2. Urine is placed in the syringe barrel 52102 and filters through the Fusion V membrane 5221 using either negative or positive pressure where bacteria get trapped in the Fusion V mesh filter. By way of example and without limitation, the amount of urine used can be 4 mL.

3. The spin column 52100 is "post-washed" with water to dilute/remove any urine droplets stuck in the column which could inhibit PCR.

4. A plug 52103 is placed at the bottom of the column and water is introduced to the filter 5221 for heat lysis. By way of example and without limitation, 200 µl of water can be introduced to the filter 5221. The plug 52103 keeps the water above the filter during heat lysis so that the bacterial DNA can be released off the filter and into the water.

5. The spin column 52100 and plug assembly are placed in a tube and the tube is placed into a heat block set 5273 for heat lysis. In one embodiment, the heat lysis is performed at 99° C. for 2-15 minutes.

6. After heat lysis, the plug 52103 is removed and the lysate is pushed off the filter 5221. The lysate can be used in PCR. By way of example and without limitations, 5-10 µl of lysate can be used per 20 µl. PCR reaction. In other embodiments, lysate may be used to reconstitute a lyophilized PCR reaction mixture without the addition of water (e.g., 20 µl for a 20 µl PCR reaction).

It should be appreciated that materials, volumes, times, and temperatures stated above are exemplary and should not be interpreted as limiting the scope of the disclosure.

Centrifuge Column Cartridge

Speeding up fluid flow in a microfluidic cartridge and ultimately eliminating bubbles in the final PCR reaction is important to obtain accurate results.

Figure 53A:
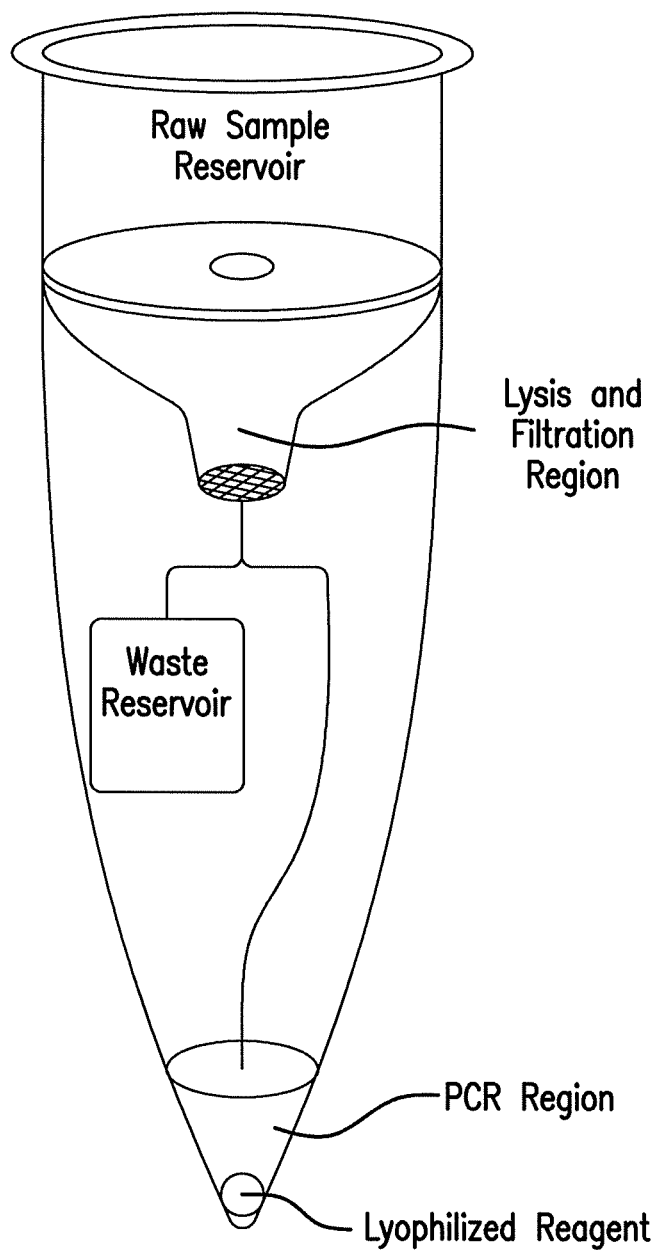
FIG. 53A demonstrates a tube shaped cartridge.

In one embodiment of the present disclosure, a centrifuged column cartridge which takes a raw sample and runs it through microfluidic channels is provided as shown in FIG. 53A. The integration of a centrifuge within the system of FIG. 53A while keeping heating processes unchanged would allow the flexibility of introducing alternative samples within the cartridge and would also help greatly in reducing bubbles in the PCR reaction reservoir.

In one embodiment, the cartridge can be shaped as a tube (as shown in FIG. 53A) or as a disk for allowing high throughput of cartridges to be spun at the same time.

Figure 53B:
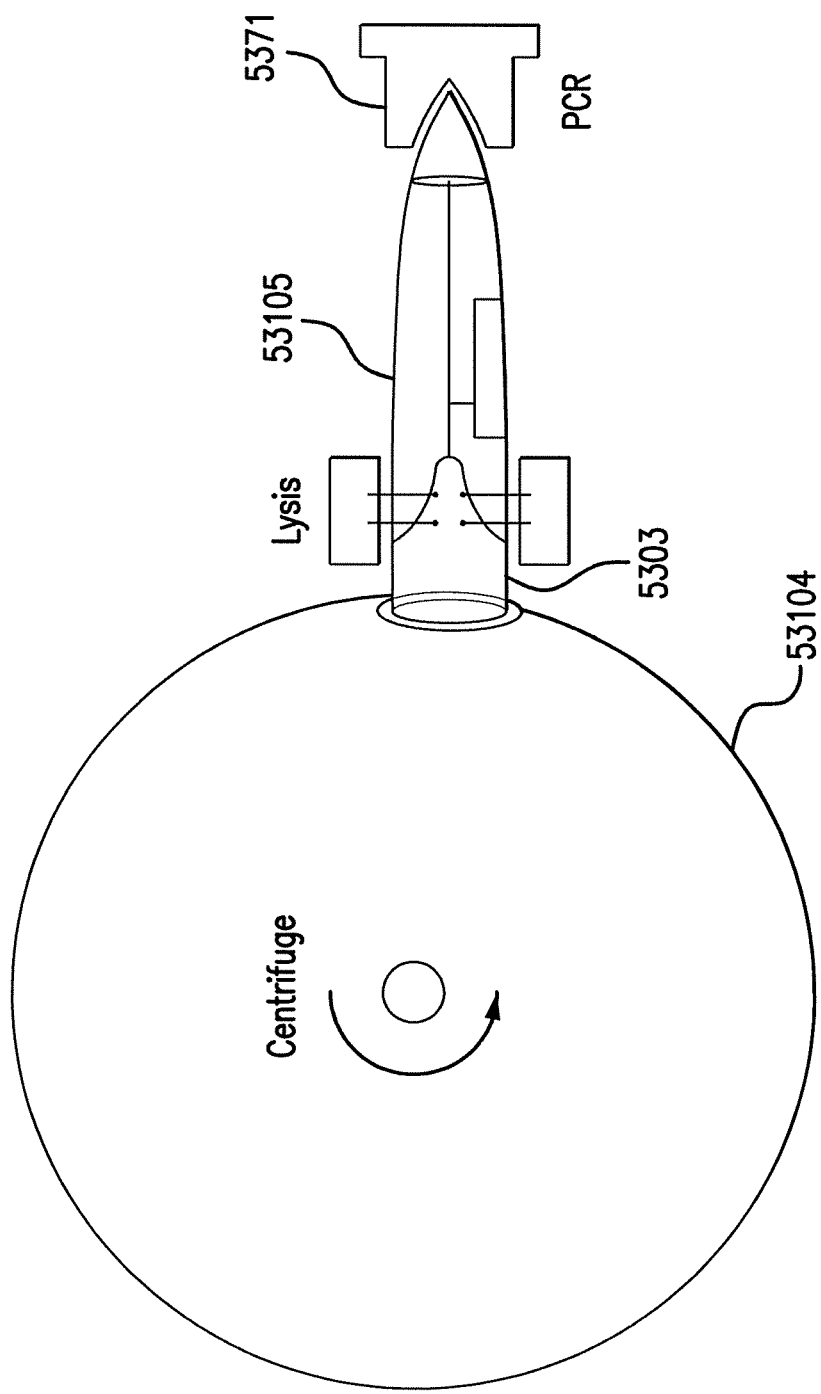
FIG. 53B demonstrates a disk shaped cartridge.

A simple representation of the assembly according to the present disclosure is shown in FIG. 53B. As the centrifuge 53104 spins the sample, the centripetal force generated from the spin would force the fluid within the sample reservoir 5303 to travel outwardly. With the closing and opening of valves attached to pressure ports (located on the column 53105) between spins of each process, the fluid of interest can be targeted to move to different regions within the cartridge. During heating processes such as lysis and PCR, the system would remain still as actuators attached to the heaters 5371 make contact with the column. Accordingly, the system according to the present disclosure would not require any active pumping components. Eliminating bubbles in the final PCR reaction would be a much easier problem to solve. Centrifugation could potentially be more effective in increasing extraction efficiency of different types of samples.

Syringe Based Cartridge

Figure 54:
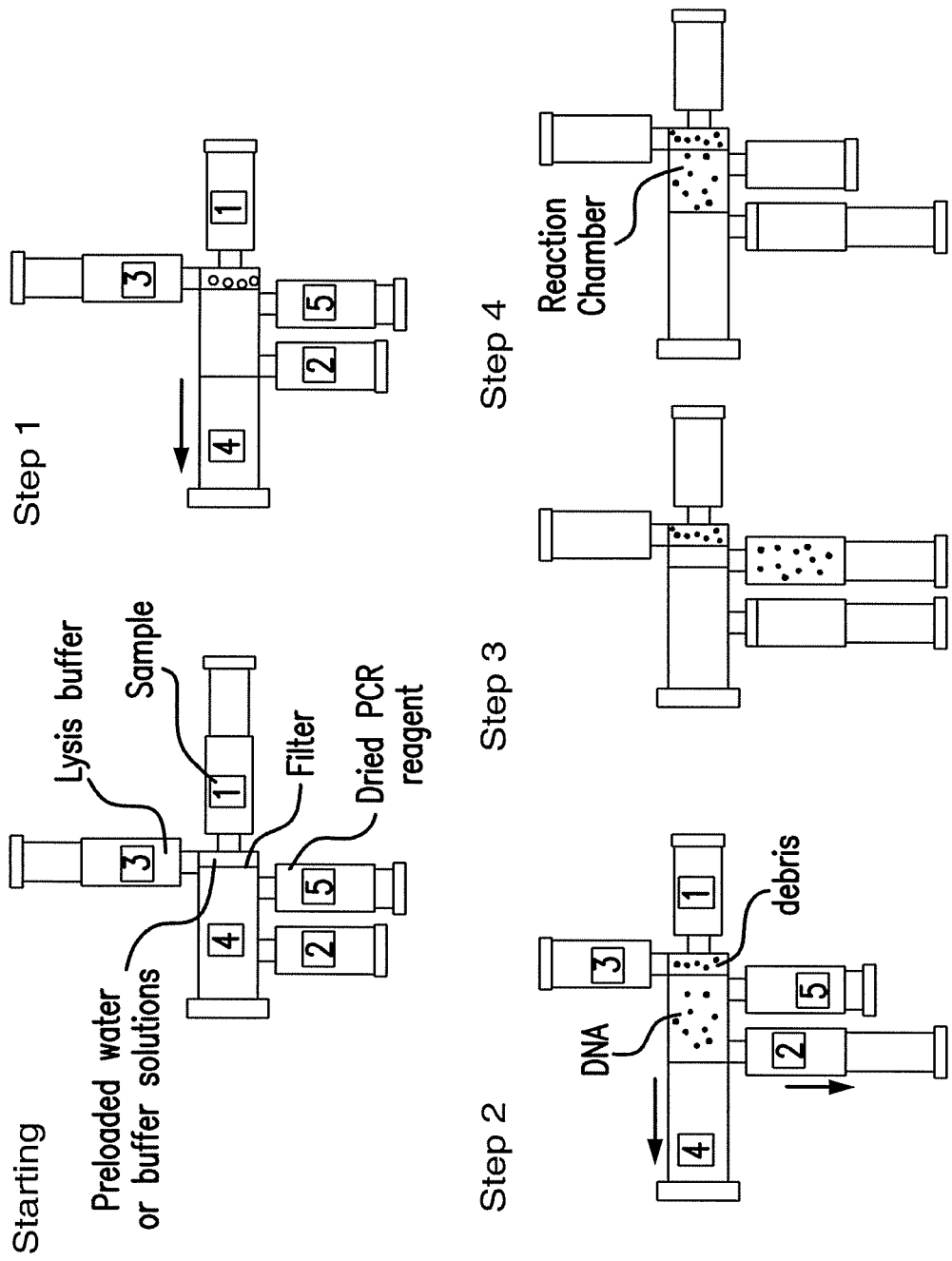
FIG. 54 demonstrates the steps of DNA extraction, mixing, and PCR performed by using a cartridge formed by several syringes.

In another aspect of the present disclosure, the steps for DNA extraction, mixing and PCR are described in FIG. 54. The reaction volume is defined by the size of the reaction chamber. By way of example and without limitation, the reaction volume can be 20 µl or a different volume.

As shown in FIG. 54, the cartridge can be formed by several syringes 1-5 being attached to each other. In one embodiment, the syringe 1-5 assembly can be a general device operated by pushing/pulling a piston to move fluid out/in the device. Lysis buffer and dried PCR reagent are preloaded into two syringes (for example, syringes 3 and 5) and attached to the reaction chamber (for example, syringe 4). Syringe 2 can be a waste chamber. The work flow can be described below:

To start the process, the user draws urine samples into syringe 1 from the urine collection cup and then attaches it to the cartridge. In one embodiment, syringe 1 is attached to the cartridge by screwing. The following steps would then be automatically implemented by an automated device.

1: Syringe 4 pulls back and syringe 1 expels to draw the sample in; cells are trapped on the filter.

2: Syringe 3 expels, Syringe 2 pulls back to move urine out and lysis buffer into the reaction chamber. Heat starts to lyse the cells to obtain the DNA. A heater can be placed under the reaction chamber in many different ways (not shown). Following lysis, Syringe 4 pulls back, syringe 3 expels, to force most of the DNA across the filter.

3: Syringe 4 expels, syringe 5 pulls back so that dried PCR reagent gets mixed with the DNA.

4: Syringe 4 pulls back and stays in a position that blocks the waste chamber inlet, syringe 5 expels. PCR can then start.

In one embodiment, advantages of the present embodiment include: the lack of need for pumps, blisters for reagents, or aliquoting systems; all samples can be exposed to excitation and fluorescence detection, providing a stronger signal without requiring compromise for the optical design; the device can be operated manually, and operation of the unit is simple.

In yet another embodiment of the present disclosure, the syringe displacement drives the fluidic function of the cartridge, and no pump is required. A user can therefore load a sample and manually actuate all the fluidic sample processing steps required for testing. For PCR, a chemical heat pack could supply heat for isothermal PCR. This approach could be robust in dealing with low-resource settings and their inherent challenges, for example, intermittent power supply, by using primarily manual steps and an isolated heat source. A low-power, robust optical detection method could be added to create a complete sample-to-answer system.

Liquid Handling Container for Multiple Sample Types

Figure 55A:
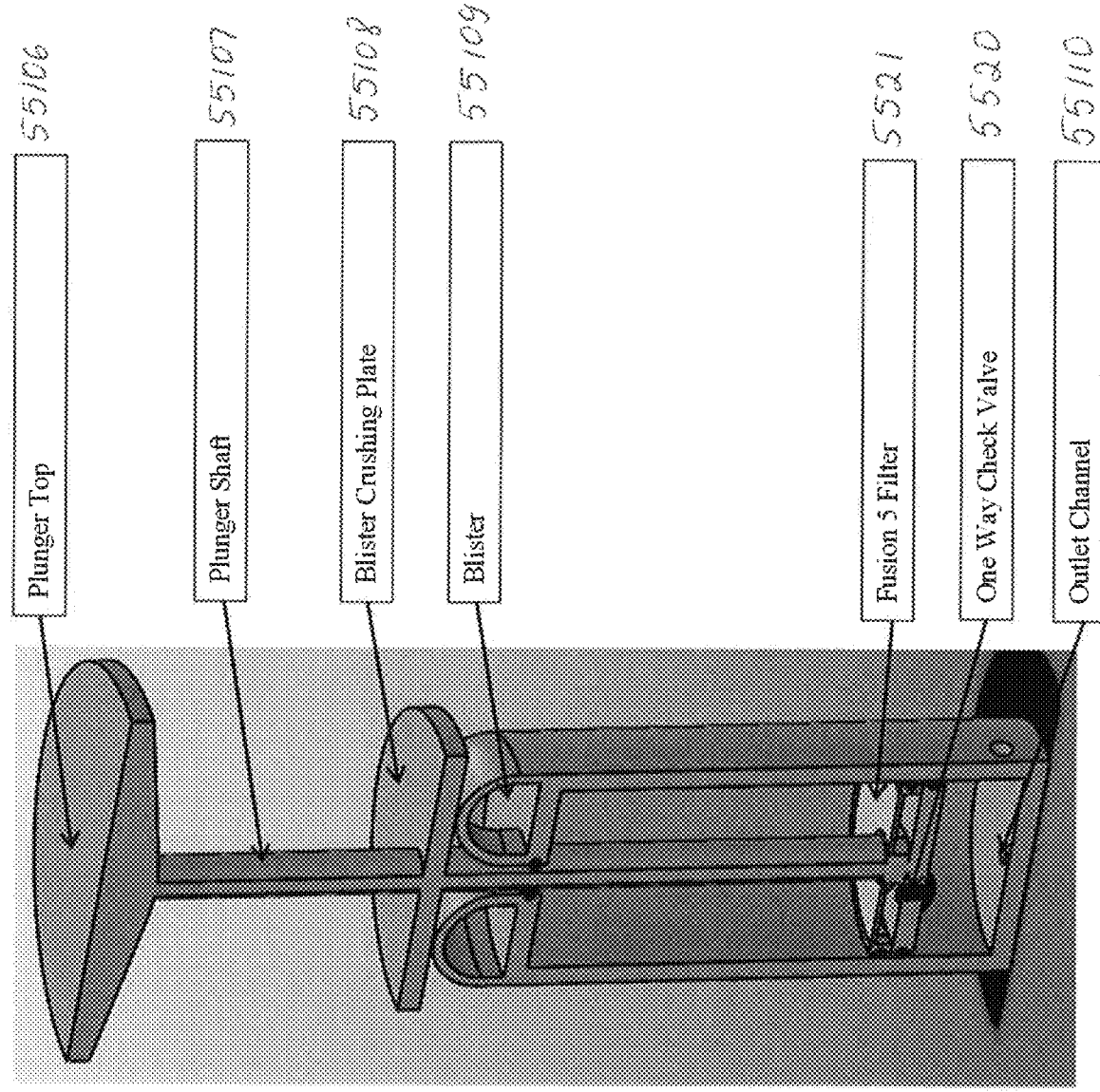
FIG. 55A demonstrates an assembly including a plunger within a sample reservoir, the assembly used for efficient lysis and DNA extraction.

In a further aspect of the present disclosure, a vaginal swab kit can be incorporated into any of the system workflows herein described. In one embodiment, a mechanically movable plunger within a sample reservoir which can filter the sample of interest, provide lysis solution which can remain above the filtered concentrate, and allow for the efficient heat (or other) lysis of the concentrate for successful DNA extraction is provided. A detailed representation of this embodiment is shown in FIG. 55A along with a workflow to describe its function. The liquid handling container according to FIG. 55A includes a plunger top 55106, a plunger shaft 55107, a blister crushing plate 55108, a blister 55109, a GE Fusion 5 filter 5521 (or a similar filter), a check valve 5520, an outlet channel 55110, and a reservoir 5503.

Figure 55C:
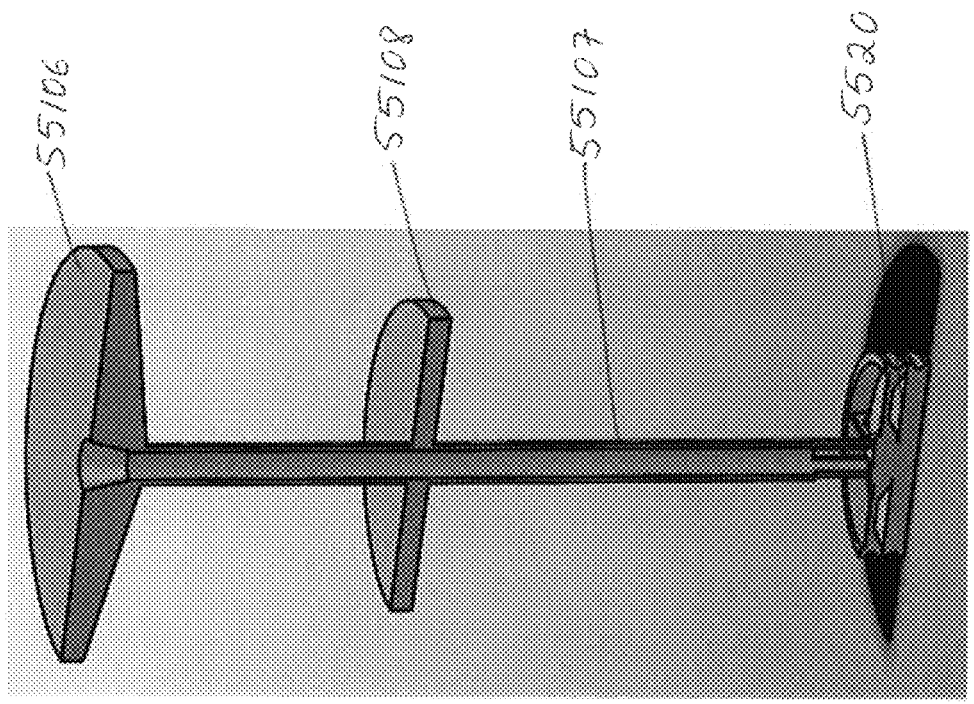
FIG. 55C demonstrates a plunger shaft for the plunger of FIG. 55A.
Figure 55B:
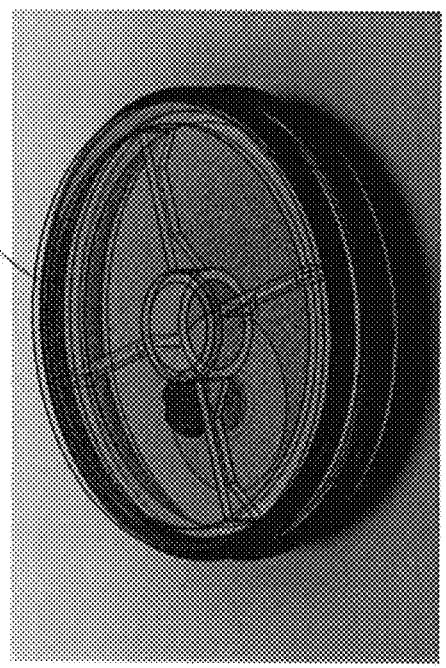
FIG. 55B demonstrates a filter and a check valve for the assembly of FIG. 55A.
Figures 55D, 55E, 55F, 55G:
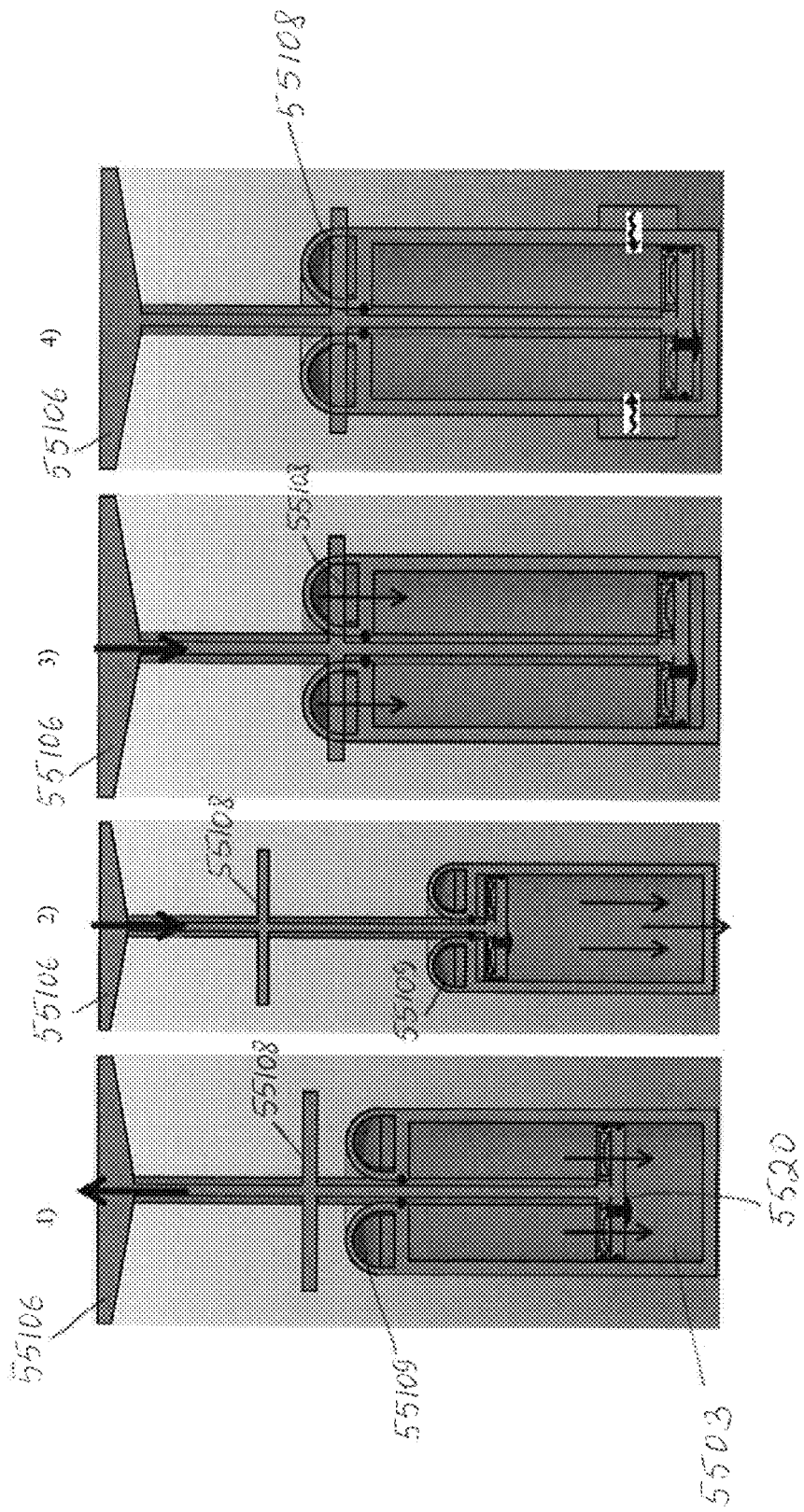
FIGS. 55D-G demonstrate a workflow for the assembly of FIG. 55A.

As shown in FIG. 55B, the filter and check valve assembly can be a separate attachment to the shaft. As shown in FIG. 55C, the plunger shaft 55107 can be a hollow tube capped at the top and exposed to the reservoir 5503 at the base to allow user to insert liquid sample or swab along the inside of the shaft The first step before processing sample within the container includes the insertion of the sample within the reservoir 5503. This insertion can be done through bulb pipetting through the channel located along the plunger shaft 55107 shown in FIG. 55B. Once the sample is inserted, the top of the plunger can be capped with a custom fitted hydrophobic filter cap.

The general workflow of this embodiment after a sample is inserted atop the filter 5521 would be as depicted in FIG. 55D-G:

1. Pull the plunger up to force the sample downward through the fusion 5 filter 5521 and check valve outlet 5520 so that waste specimen is below the filter/check valve assembly and the bacteria is trapped above the fusion 5 filter 5521, 2. Push the plunger downward to force the waste specimen to exit through the outlet channel 55110 on the bottom of the reservoir 5503, 3. Continue to push the plunger shaft 107 downward so the plate 55108 located above the blister 55109 will burst the blister 55109 to introduce wash/lysis solution above the filter, 4. Lyse the sample using heat (e.g. IR or Joule heating) introduced directly into the reservoir walls in the region above the filter 5521, 5. Steps one and two can be repeated to force the lysed solution outside the outlet channel 55110 or a secondary channel can be used to draw the lysed solution through negative pressure.

In one embodiment, a wedged blister crushing plate (instead of a fully cylindrical blister crushing plate as shown in FIG. 253-a) can be included on the shaft 55107 of the plunger to allow for the bursting of blisters with different reagent types (e.g. detergents or water). The user or instrument would rotate the shaft to target the wedged plate above the blister of interest followed by a downward press to burst the blister and force fluid into the reservoir and above the filter.

The system according to the current embodiment can be handled with very little user effort after adding sample and could potentially reduce sample preparation time. With the shortening of this time along with the option of providing the user with different kit configurations, the efficiency of the workflow could improve and the flexibility of design could be expanded.

Magnetic or Optical Labelling of Targets

In some embodiments of the present disclosure, enrichment of a sample could take the form of labeling the targets magnetically or optically. By way of example and without limitations, the targets can be labeled with fluorescent probes. Enrichment could be performed using inertial microfluidics. In another embodiment, enrichment could be a filtration process.

Figure 56:
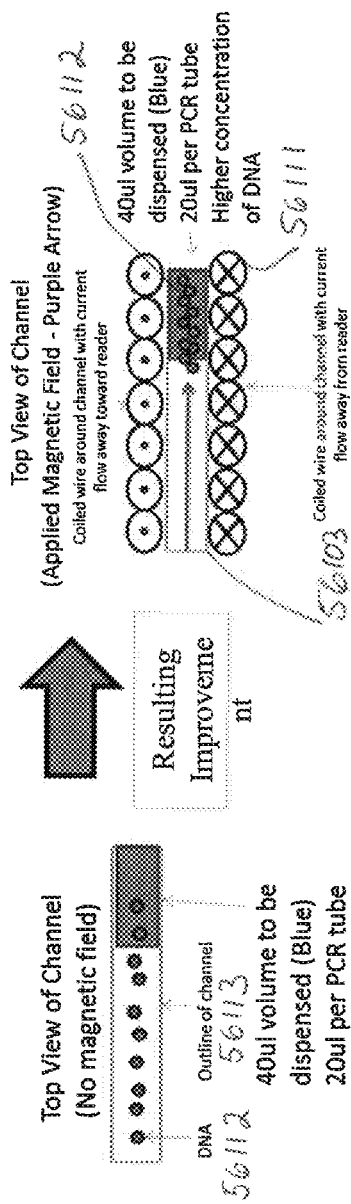
FIG. 56 demonstrates an improvement in target concentration process achieved by using magnetic labelling of targets.

In one embodiment, a solenoid (coil of wire) surrounding the main channel length (internal or external) is employed in conjunction with the cartridge. The images in FIG. 56 show a representative result of the applied magnetic field. A current running through the solenoid 56111 would create a magnetic field to force the DNA 56112 toward the portion of the fluid that is placed in PCR vessels, resulting in a higher concentration of initial DNA for amplification.

Due to the geometry of the tube, the coil 56111 could be inserted into the cartridge at the time of manufacture or implemented in the instrument. Electrical contacts would have to be available such that a current could be run through the coil 56111 which is provided by the instrument. Given that the instrument has a large power supply (by way of example, 24V, 12 A), there could be enough magnetic field to push the DNA along the channel 56113 and concentrating it in the portion of the fluid that will be placed into the PCR tubes. This higher concentration would reduce the turn-around-time (TAT) of a positive sample as well as the ability to detect low concentration of target samples.

Anchoring Tube for Lyophilization Process

In a cartridge system, it is very critical to keep a lyophilized reagent at a designed location or the bottom of a PCR tube where the rehydration occurs. With the larger PCR tube than the actual PCR reaction volume, the lyophilized reagent pellet or bead can be displaced into other locations during shipping or handling.

Figure 57A:
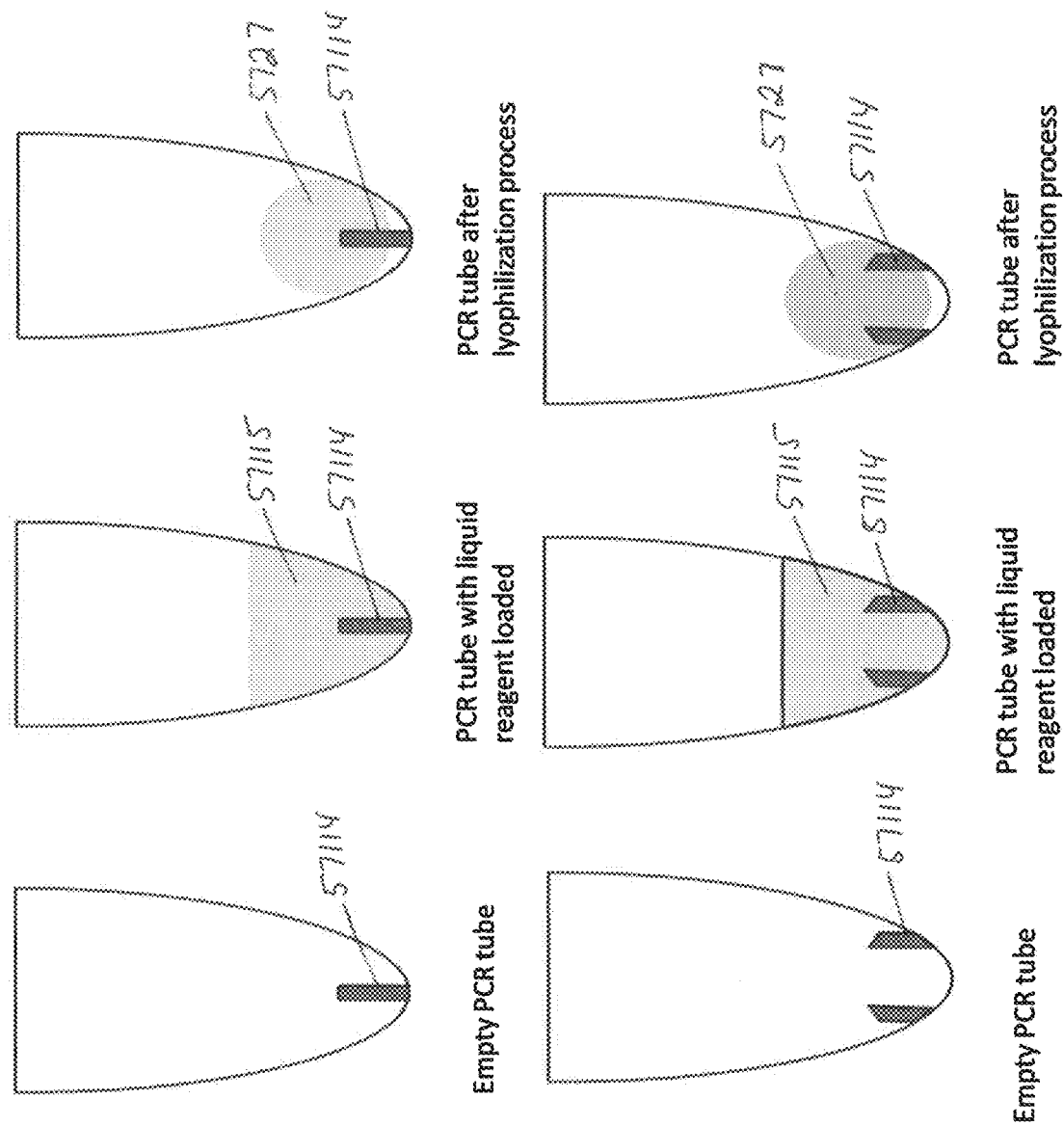
FIG. 57A demonstrates a PCR tube having an anchoring feature according one embodiment of the present invention.
Figure 57B:
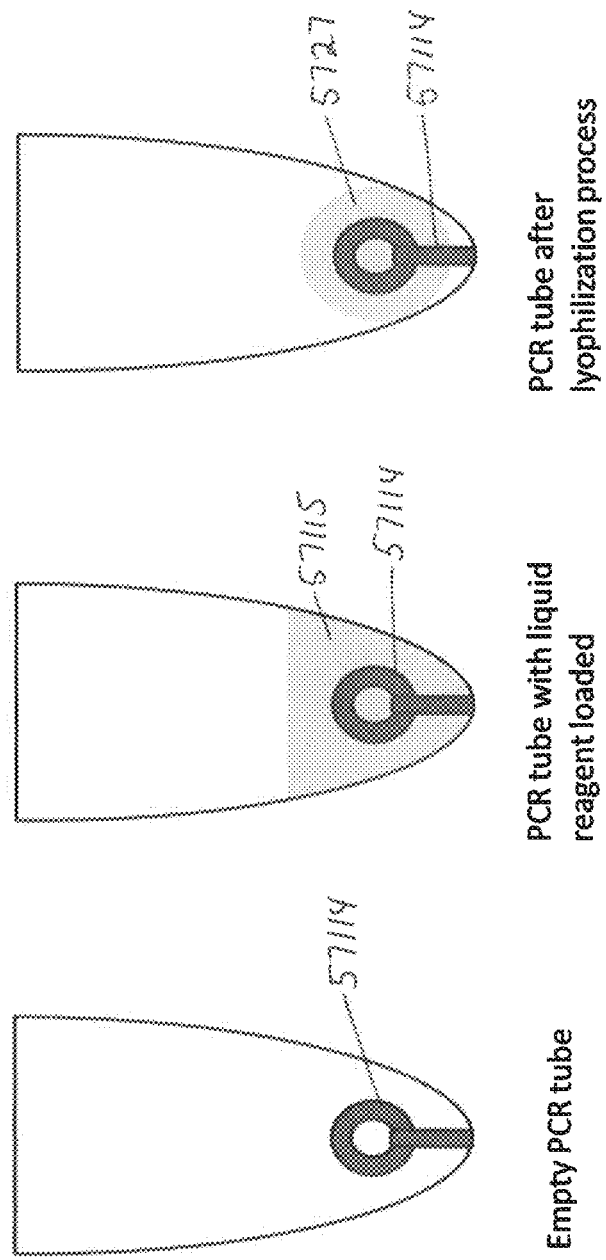
FIG. 57B demonstrates a PCR tube having an anchoring feature according another embodiment of the present invention.

In one embodiment of the present disclosure, a PCR tube that has an anchoring feature at the bottom of the tube is provided. As shown in FIGS. 57A-B, the pellet 5727 can be anchored during the lyophilization process and shipping/handling. Reagent mixture 57115 becomes pellet 5727 following lyophilization. The anchoring features 57114 are designed to be tall enough to provide enough anchoring structure but short enough that the optical access from the side is not interrupted. By way of example and without limitation, the anchoring features 57114 can be in the form of a single pillar or multiple pillars attached to the bottom of the PCR tube. The pillars can be differently shaped. With this approach, the lyophilization process should occur within the custom PCR tube.

Fluorescence Detection Through a Flow Guide

Fluorescence detection from the top of a reaction chamber, for example a PCR tube, for the cartridge of FIG. 6 can be challenging to implement because relatively busy fluidic design features for the aliquoting function are located such that they can interfere with the optical access from the top.

With respect to FIG. 58A, a new method for fluorescence detection is provided. Specifically, optical access from the top side of the tube is provided so that the optical module design might be decoupled from the heat block design. The new method is to use the solid flow guide feature 5826 as a light guide. In one embodiment, the flow guide 5826 can be designed as a solid cylinder with one side cut flat for the flow guide function while the solid core can serve as a light guide since this solid feature has a higher refractive index than the surrounding air.

The excitation light 5869 is focused from outside into the top end of the flow guide 5826, which channels the light through the center of the flow guide down to the PCR mix 58116 at the bottom in the reaction chamber or tube 5810. The same light guide is used to collect and channel the fluorescence emission, which will be directed into the photo detector 5885 with an integrated dichroic mirror 5895 and a lens 5879.

Figure 58B:
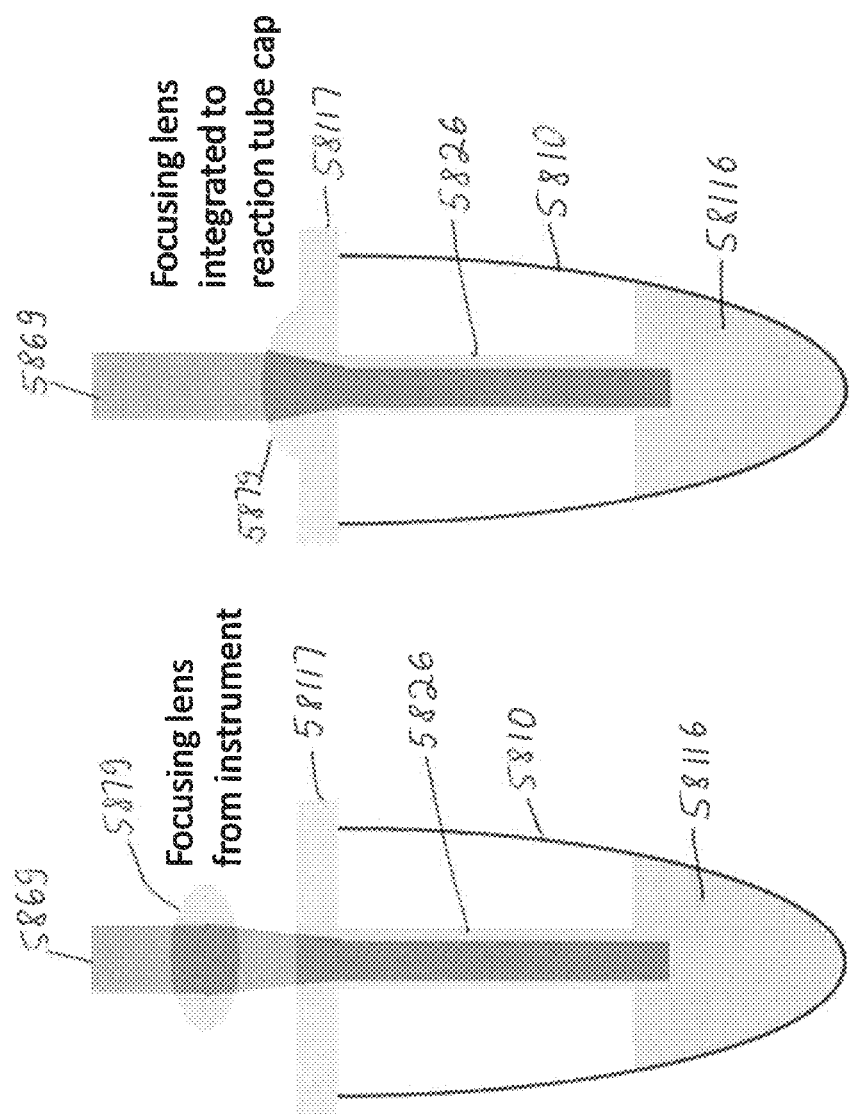
FIG. 58B demonstrates a focusing lens integrated to the capping part of a reaction tube.
Figure 58C:
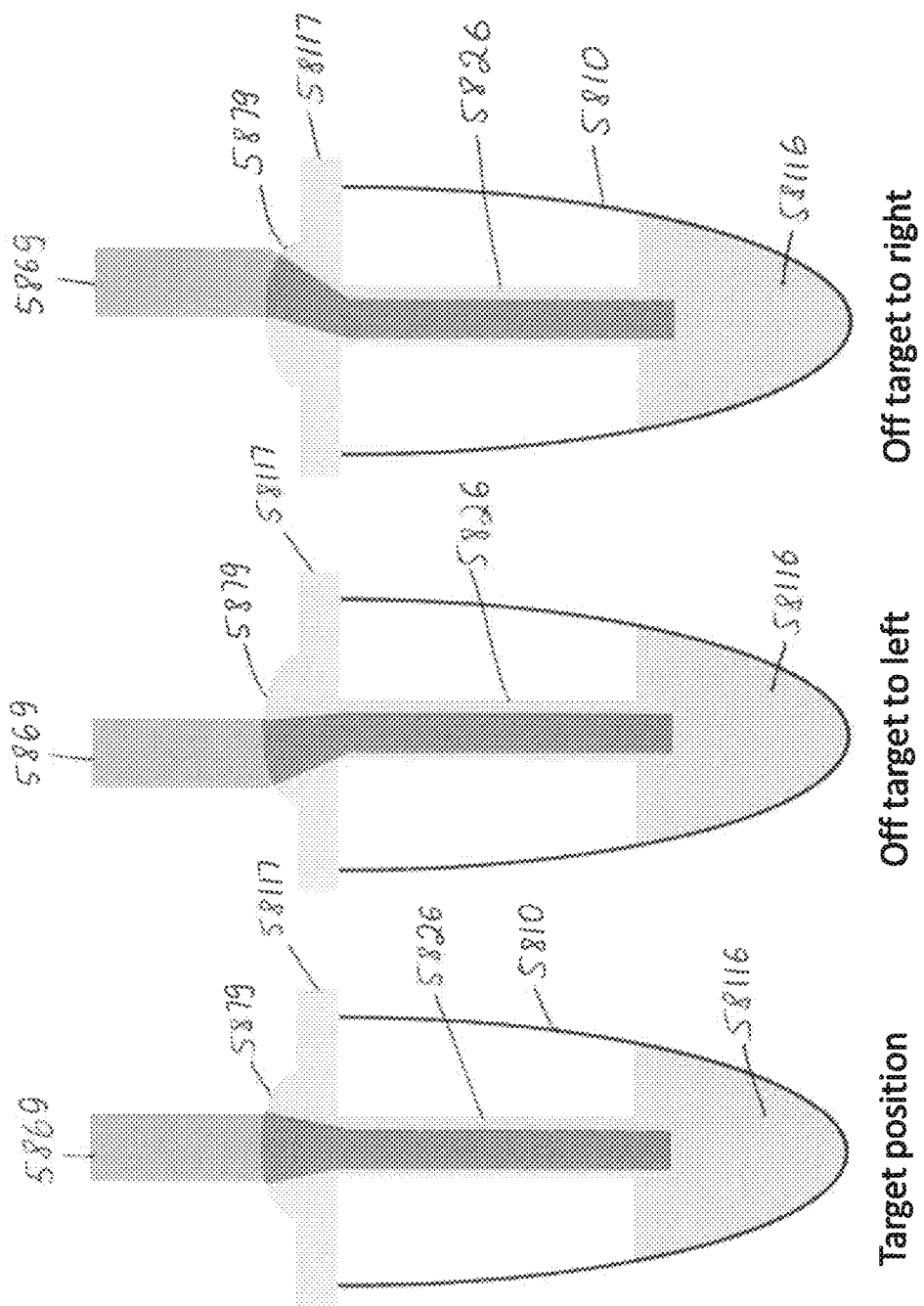
FIG. 58C demonstrates a focusing lens integrated to the capping part of a reaction tube so that slight off-target cartridge installation can be tolerated by the lens on the cartridge side.

In one embodiment, the focusing lens 5879 is integrated to the capping part 58117 of the reaction chamber or PCR tube 5810 as shown in FIGS. 58B-C so that slight off-target cartridge installation can be tolerated by the lens on the cartridge side.

Electric Field Lysing

According to one embodiment of the present disclosure, lysis is performed in the cartridge by rapid heating via cartridge heaters. These heaters require a separate heating block, as well as taking some time to lyse the sample.

In one embodiment of the current disclosure, a method of lysis using an electric field is provided. With an appropriate strength electric field, the field causes electroporation of cells, which allows the DNA to be removed from the cell for PCR analysis. Depending on the strength of the electric field, the time required to lyse the cells can be reduced to less than half a minute and use less power. This electric field can be created by two pins biased with a power supply (and supporting electronics). These pins would be placed across from each other in the instrument and the main channel of the cartridge as shown in FIG. 297-1 would be placed in between them when the cartridge is in the system. When ready to pull the sample to the PCR reaction tubes, the fluid could be pulled at controlled speed to lyse the sample that would be entering the tubes. In FIG. 297-1, the small channel provides a small target for the field, which gives the field a higher concentration. Further, instead of performing lysis in the lysis chamber, lysis could be performed while moving the lysate through the main channel with the electric field.

Microfluidic Positive Pressure Cut Off Valve

Figure 59A:
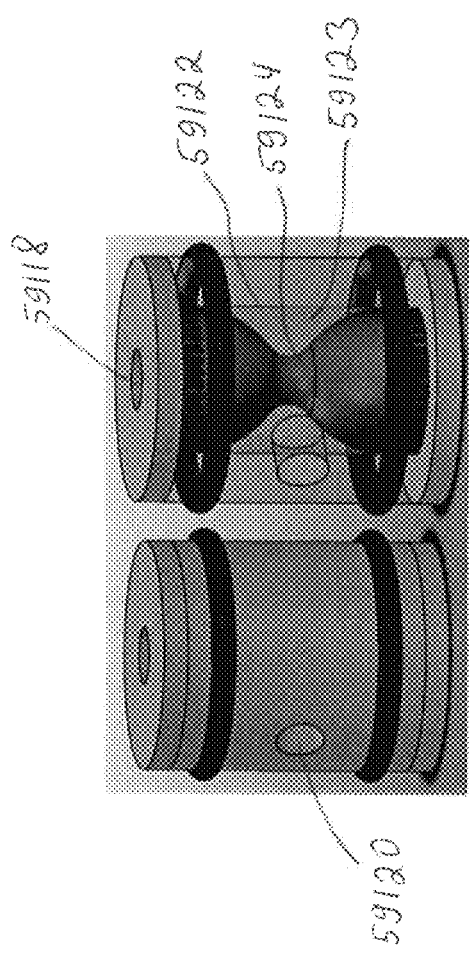
FIG. 59A demonstrates a regulated microchannel flow assembly.
Figure 59B:
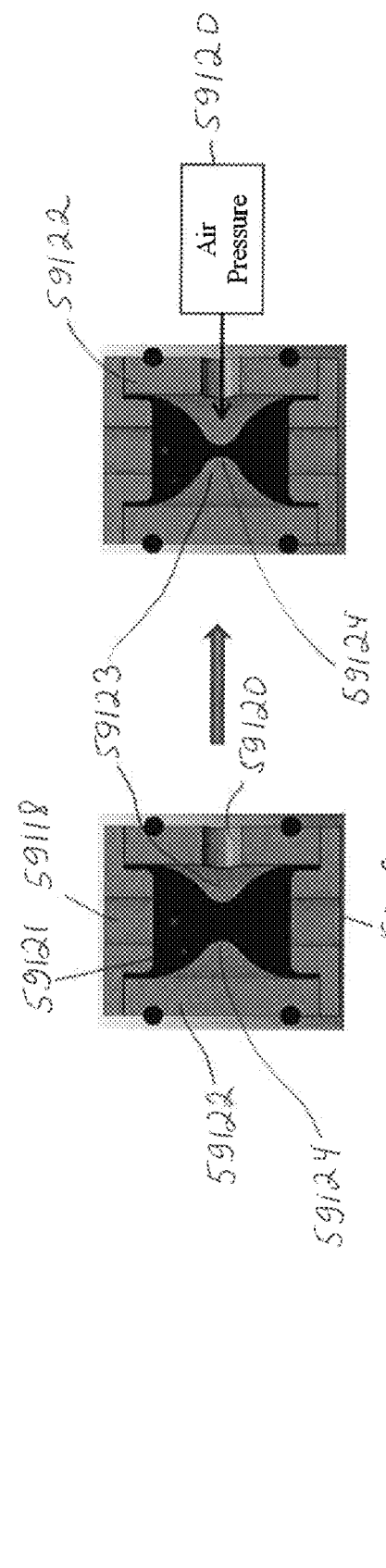
FIG. 59B demonstrates a process of regulation of continuous flow passing through a microchannel.

The use of different fluid flow valves in microfluidic applications can be useful in maintaining a controlled flow within a microchannel. Key factors to consider when choosing such valves includes reliability in control processes of fluid as well as overall cost of implementation at a large production scale. In one embodiment of the present disclosure, continuous flow passing through a microchannel is actively regulated as shown in FIG. 59A-B.

The inlet and outlet channels 59118 and 59119, respectively would be aligned axially to the flow, while the perpendicular port 59120 would be connected to an active pump which would force air into the closed space between the rubber 59121 and the inside walls of the valve mount 59122. As positive pressure is pumped into this cavity, the hourglass shaped rubber neck 59124 would narrow and eventually close from a buildup of pressure within the cavity 59123. The closing of this channel 59124 would allow for the separation of controlled fluid volumes from a larger fluid volume as could also ensure the closing of channels to allow an upstream process to occur.

Sample Processing Control

For a sample-to-answer system that uses a patient sample (e.g., vaginal swab sample, urine, etc.) to test for a microorganism of interest (e.g., CT/NG/TV/MG etc), controls are an important consideration. Having a sample processing control is a highly valued measure to ensure an assay cartridge properly prepares a patient sample to ready it for PCR, other amplification methods, or other downstream applications.

In one embodiment of the present disclosure, a sample processing control within a rapid filtration concentration and heat lysis preparation is provided. In this way, a sample can be prepared for PCR in a few minutes and the control will guarantee that the sample has been properly captured and lysed. The sample processing control (SPC) is achieved by subjecting the sample (whether provided in the form of potential host cells or as potential isolated pathogens) and the SPC to a capture step (capturing all targets of interest, for example, cells) followed by a lysis step (lysing all targets of interest) to release genetic material from within the targets of interest, which is then in turn followed by an amplification reaction for the target pathogen(s) and the SPC.

In one aspect, the SPC can be a dried micro-organism (e.g., fungus, bacteria, yeast, virus, parasite, etc.), plasmid construct, or polynucleotide (natural or synthetic). The SPC can be a human cell or DNA sequence. In one embodiment, the SPC can be dried down in the form of a lyophilized pellet, powder, or cake. The SPC can be impregnated into the capture filter (e.g., glass fiber mesh filter). The SPC can be pre-loaded into the cartridge such that it is re-suspended when sample is added. Alternatively, it can be stored in a liquid reagent (i.e., blister pack) that is introduced to the filter with a wash step. Alternatively, it can be stored in a sample transport tube such that it is introduced along with the sample. This approach would ensure the proper transport media was used for the test. In some embodiments, a pre-determined concentration of cells can be used as a SPC to seed the filter with sufficient particles to enhance capture efficiency.

In one embodiment, SPCs will have similar size as target organisms and be lysed at similar temperatures. Alternatively, the SPC can represent a worst case (smaller in size and therefore less likely to be capture, requiring higher temperature to lyse, or both).

Progressive Microfluidic Capillary Stop Valves

In one embodiment of the current disclosure, capillary stop valves can be incorporated into a microfluidic cartridge, including those as described herein. Capillary stop valves as shown in FIGS. 60A-C and FIG. 61 utilize surface tension at a boundary where an abrupt change in angular geometry changes the curvature of meniscus which creates a pressure barrier at that boundary. The barrier is great enough to overcome the positive pressure gradient which causes the movement of fluid.

One equation used to describe the pressure barrier at the boundary is as follows:

$$\Delta P = \frac{-dU_T}{dV_l} = \gamma_{la}\left(\cos\theta_c \frac{dA_{gl}}{dV_l} - \frac{dA_{la}}{dV_l}\right) \qquad \text{Equation 1}$$

where $U_T$ is the total interfacial energy of the system and $V_l$ is the volume of the liquid in the capillary system, γia is the surface tension at the air-liquid interface, θc is the contact angle, $A_{Sl}$ is the area of the wetted surface-liquid interface and $A_{la}$ is the area of the liquid-air interface.

The main goal of the stop valves is to create a large liquid-air interface so the last term on the right side of the equation 1 can dominate and make the pressure gradient negative to stop the flow of fluid.

FIGS. 60A-C and 61 provide an explanation of how the liquid wicks and stops at a stop valve using an abrupt increase in channel width, known as an expansion angle, represented as beta.

In FIG. 60A, the fluid is wicking through the channel due to capillary forces. FIG. 60B is known as the transition region where the fluid has reached the capillary stop valve and the meniscus is inverted going from concave to convex. FIG. 60C is known as the expansion region where the meniscus does not change and the x-position of the fluid changes. In each of these regions, the equation for the pressure gradient at the boundary is as follows:

$$\Delta p = 2\gamma_{la}\left[\frac{\cos(\theta_c + \beta)}{w} + \frac{\cos\theta_c}{h}\right] \qquad \text{Equation 2}$$

Equation 2 comes from the Young-Laplace equation which describes the interface of two fluids, in the present case the two fluids are liquid and air. Another example of a stop valve is shown in FIG. 61. The stop valve consists of an abrupt decrease in width followed by a 90 degree angle.

In one embodiment of the present disclosure, a flexible and robust capillary stop valve system that uses a progressive set of stop valves is provided. A set of capillary stop valves is placed in series, where each valve in the series is designed to stop a liquid using a different critical contact angle. The precise contact angle (e.g., hydrophobicity/hydrophilicity) does not need to be known. By way of example and without limitation, each valve in the series can change from the previous valve angle by approximately 5 degrees: if the one of the initial valves does not stop the liquid then it can be stopped further down the line by one with greater "stopping power."

Figure 62:
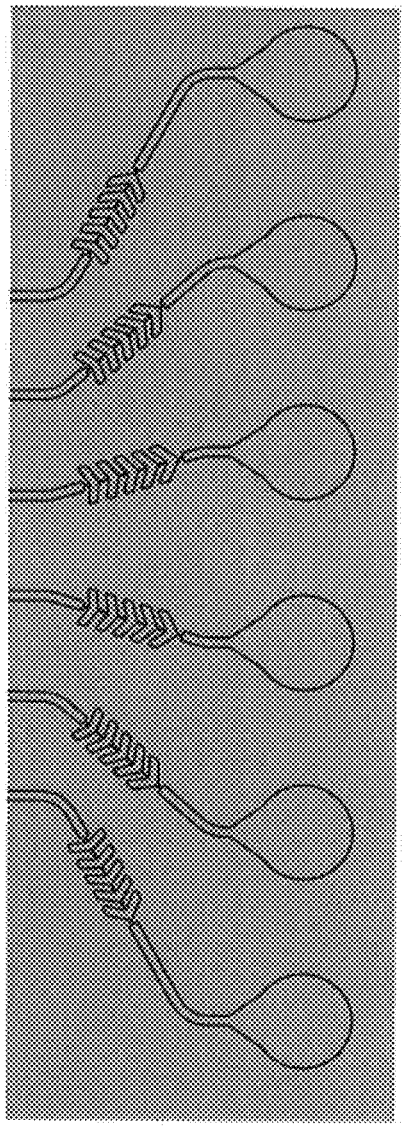
FIG. 62 demonstrates an expansion angle progressive stop valves system.

As seen from Equation 2, the cosine indicates that the pressure gradient is not linear, but parabolic. Therefore there is an ideal beta expansion angle that provides the largest pressure drop. If the beta expansion angle is too small, then the stop valve will fail and if the angle is too large, the stop valve will also fail. A successful valve needs to fall in between these limits. If the contact angle is unknown then these limits cannot be calculated. As shown in FIG. 62, a series of capillary stop valves with increasing beta expansion angles is employed for flow stopping. Multiple stop valves with different beta expansion angles one after another are beneficial because the probability that one of the stop valves will fall between the stopping limits is large. Therefore, a progressive series will be able to stop a solution whose contact angle is unknown (e.g., a patient sample which may present with variable fluid properties). The progressive stop valves also provide backup so if one valve fails, for example, due to extra stress put on the chip, then the next valve can potentially stop the fluid.

In one embodiment, the expansion angle of the stop valves can be increased. In another embodiment, the channel width can be decreased. In another embodiment, the depth of the channel can also be increased across the boundary of the valve in order to increase the pressure barrier created by the stop valve. In a further aspect, a regressive series can also be used, in which the geometric parameters listed above are varied in the opposite direction. In another embodiment, different channel geometries can be used and still benefit from the progressive concept. For example, rectangular, semi-circular, circular, trapezoidal, etc. channel geometries can be used.

Accordingly, a method of controlling fluid flow comprises providing a microfluidic channel having at least one series of capillary stop valves having different expansion angles and introducing fluid into the microfluidic channel, wherein the capillary stop valves prevent fluid flow past the stop valves. There is also provided a microfluidic system having a microfluidic channel comprising at least one series of capillary stop valves.

Figure 63:
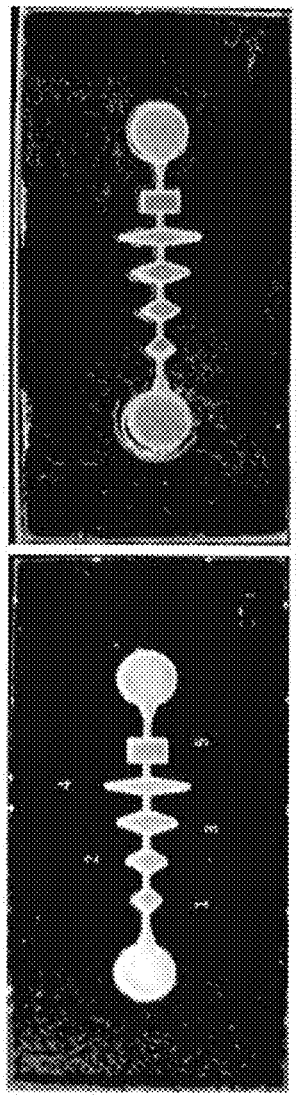
FIG. 63 demonstrates a progressive stop valve system in PMMA chip.

FIG. 63 shows a capillary stop valve chip made in PMMA and cut with a laser cutter. In one embodiment, the beta expansion angles are as follows from left to right: 50, 60, 70, 80, 90°. Yellow aqueous dye was inserted into the chip. Due to capillary forces, the dye wicked into the channel. As shown in FIG. 63, the first stop valve failed because the expansion angle was too small, while the second proved successful.

Figure 64:
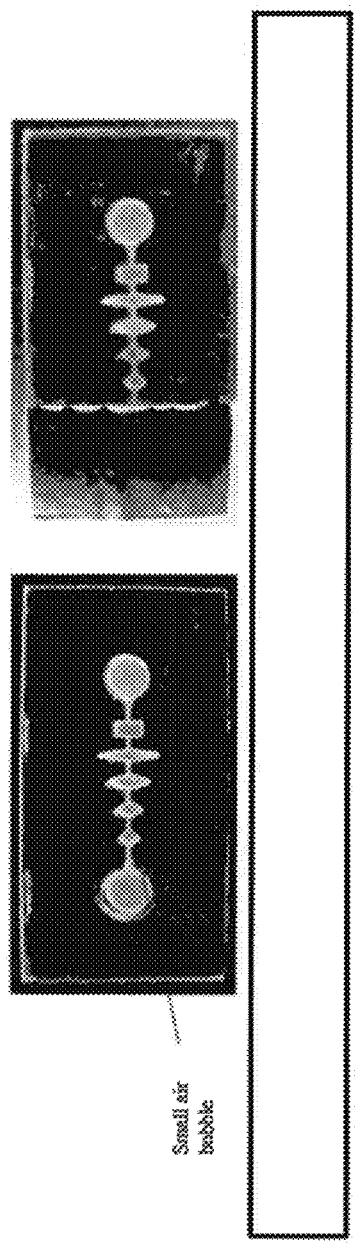
FIG. 64 (left) demonstrates progressive stop valves in a chip.

FIG. 64 show the progressive stop valve system under a "stress-test." As indicated in FIG. 64, an air bubble was trapped in the first stop valve when the dye was wicking in the channel. Adhesive foil was then placed over the inlet of the chip and the chip was placed on a hot plate and heated to 65° C. Due to thermal expansion of the bubble, the second stop valve failed and the sample continued to move until it reached the third valve which provided a large enough negative pressure gradient to stop the dye as can be seen in FIG. 64. By way of example and without limitation, the chip was left on the hot plate for 7 minutes and the third valve successfully stopped the dye for 5 minutes.

In one embodiment of the present invention, a channel having progressive stop valves can be used in the cartridge of FIG. 5. During the lysis process, the fluid in the lysis chamber 505 can tend to "escape" through the capture filter 521 and move into the main channel 512 as the pressures between lysis chamber 505 and main channel 512 are balanced. In such a case the sample that has not been lysed could enter the main channel 512, resulting in fluid being aliquoted into the reaction chamber that may not have genetic material available for an amplification or other process. To help avoid this scenario, channels having stop valves can be placed in main channel 512, so that any such movement of fluid entering the channel would be stopped by the stop valves.

High Speed High Density Digital PCR Devices

In one embodiment of the present disclosure, an ultra-fast digital PCR system is provided. The system comprises a thermally conductive chip, including a thin substrate with metal film heaters on one side and an array of nanoliter (nL) holes in the other side of the substrate. In one embodiment, the thermally conductive chip is preferably manufactured of glass, silica, or quartz. The system further comprises a flexible cover that allows liquid to flow over the array in a loading step. The cover supports an initial gap, but can be depressed to seal the well array in a sealing step. By way of example and without limitation, the initial gap can be 20-1000 µm. If an amplification master mix (e.g., PCR master mix) is used in the loading step, then following the sealing step, with the wells sealed off, the chip can be used for rapid thermal cycling enabling digital PCR.

Incorporating such a device in a cartridge that includes a sample preparation functionality could enable sample to answer diagnostics that offer the great advantage of sensitive DNA/RNA quantification. In one embodiment, where high throughput is desired, the cartridge 501a as shown in FIG. 5 can be used in conjunction with the digital PCR system described here. In one embodiment, following lysis, the lysate can travel through the main channel 512 to an aliquoter that will deposit the lysate into the array of nanoliter holes on the thermally conductive chip. In one embodiment, the aliquoter can flood the lysate over the array of nanoliter holes until they are filled, or alternatively, the aliquoter can be designed to deposit a particular number of aliquots at the same time, with the aliquoter and the thermally conductive chip being moved in relation to each other. Once the nanoliter holes are filled, the thermally conductive chip can then have the configuration, and be subjected to the processes, described herein.

The metal film heaters will allow for very rapid (<5 sec) thermal cycling like the chips previously described (WO 2011002749A1 to Hasson et al.) by using Joule heating. Suitable metals include but are not limited to platinum, nickel, titanium, chromium, gold, or various alloys (preferably a platinum film with a titanium adhesion layer). Alternatively, within the scope of the disclosure, the metal film can be replaced with another film capable of rapid Joule heating (e.g., Indium tin oxide).

The metal film heater(s) can be any pattern designed for thermal uniformity (e.g., serpentine, rectangular grid, concentric sections, grid of serpentines, etc.). Given a transparent substrate it can also be possible to do fluorescence excitation and/or detection through the backside (heater side) by viewing through gaps in the heater pattern. ("Nucleate Pool Boiling Characteristics From A Horizontal Microheater Array" Univ. of Maryland Dissertation, Christopher Henry 2005). The substrate should be thermally conductive to facilitate heating the wells using films that are separated from the wells by the nominal thickness of the substrate. Glass, silica, quartz, other oxides, and even silicon would be suitable. The thickness of the wafer will affect the heating rate and as such should remain relatively thin. In one embodiment, the thickness of the wafer is in the range of 100-1000 µm.

The array of nanoliter wells could be similar to those known in the art for other digital PCR devices. The holes could be produced for example using various etching techniques (wet etching such as HF, reactive ion etching, deep reactive ion etching) of any other well-known microfabrication technique. The wells could be hemispherical, pyramidal, cylindrical, rectangular, or any other suitable shape. The volume can be determined based on the particular application and the expected concentration of amplification targets. For example, wells in the range of 0.1-10 nL can be appropriate (most preferably about 1 nL).

The surfaces of the nanoliter well array can be treated to promote proper wetting. It is desired that the liquid fill the nanoliter wells without forming air gaps or bubbles, while the surfaces between the wells should minimize residual liquid that remains behind. So hydrophilic wells and hydrophobic inter-well surfaces are desired. Any well-known techniques for surface treatments can be employed including various chemical treatments as well as micro/nano texturing.

The layout of the array of nanoliter wells can be rectangular or otherwise. Layouts that improve thermal uniformity across the various wells are preferred. For example, the wells could be laid out in concentric circles, while the heater pattern is similarly laid out using concentric sections. In some embodiments, the heater pattern can extend beyond the extent of the well array, forming a thermal guard ring around the perimeter of the well array, improving the uniformity of temperature.

As described above, the flexible cover should allow the liquid to fill the well array in a loading step, so in its initial configuration it will be several microns above the free surface of the well array. However in the sealing step, the cover film and well array must be brought into intimate contact in order for the film to seal the wells. This could be achieved by moving the cover film, the substrate, or both.

In one embodiment, the flexible cover can be closed by inflating an air bladder which pushes the flexible film against the well array. With transparent covers and air bladders optical excitation and/or detection could also be done on this side. Other mechanisms of closure are possible (e.g., piston). In some embodiments, the closure can permanently seal the two surfaces (e.g., using a pressure sensitive adhesive).

Many suitable materials are available to use for the cover film including but not limited to PVC, polyethylene, polyurethane, COC, COP, PMMA, etc. A certain degree of compliance can be required for the cover film to seal the well array. Such compliance can be achieved by choice of material and film thickness.

The digital PCR chip preferably would be sealed within a disposable cartridge or pouch (preferably made substantially of plastic). The cartridge could include any necessary sample prep, target enrichment, cell lysis, sample purification, dilution, mixing, etc. Following the sample prep, prepared PCR mastermix can be loaded into the nL well array for quantification.

In one embodiment, the digital PCR chip is part of a system comprising a nanofluidic chip with a thermally conductive substrate including thin film heaters on one side and an array of nL holes in the other side, a flexible cover used to seal said array following the introduction of an amplification liquid, a means to bring said nanofluidic chip and cover into intimate contact to seal the amplification liquid in the nL holes, a means to detect the amplification products in said array of nL holes.

Further, while the term PCR has been used throughout, it is contemplated that such a device can be used in other amplification reactions (e.g., isothermal amplification) consistent with the aim of DNA/RNA quantification.

By way of example and without limitation, the high speed high density device could include an array of wells. For instance, the device could include a 10×15 mm chip with 50×50 array of 1 nL wells. The High Speed High Density digital PCR device according to the present disclosure offers a rapid solution for digital PCR. With this significant increase in speed, new possibilities featuring DNA/RNA quantification will be available in the realm of point of care diagnostics. Advantages of using glass construction include rapid heating, high precision possible for making the nanoliter wells, and low autofluorescence. Other advantages include that the presence of metal film on the outside surface of the substrate eliminates the need to passivate the reaction mixtures from the metal. Further, no glass to glass bonding is required because only a single wafer is used for the high density device.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein.

It will also be appreciated that although some embodiments have been grouped together under headings for ease of understanding, it is intended that any of the embodiments are applicable to the entire scope of the disclosure herein, and the inclusion of an embodiment in a particular section does not preclude it from being used in combination with elements provided in separate sections of the disclosure.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for analyzing a biological sample for the presence of a target of interest, the method comprising:
   providing a cartridge, wherein the cartridge comprises a sample chamber, a waste chamber, and at least one reaction chamber, wherein fluidic communication between the sample chamber, waste chamber and at least one reaction chamber is provided by one or more microfluidic channels;
   adding the biological sample to the sample chamber comprising a filter;
   enriching the biological sample;
   wherein the step of enriching the sample comprises:
   (a) filtering the biological sample through the filter in the sample chamber, wherein fluid passed through the filter is stored in a waste chamber and the remainder of the biological sample remains in the sample chamber; or,
   (b) magnetically labeling the targets of interest within the sample and subjecting the labelled sample to a magnetic field;
   washing the sample by releasing a washing fluid into the sample chamber;
   drawing the washing fluid through the filter by applying positive or negative pressure, wherein the washing fluid passed through the filter is stored in the waste chamber;
   releasing a lysis fluid into the sample chamber;
   producing a lysate by (a) applying heat to the filter and the biological sample or by (b) subjecting the biological sample to an electric field to cause electroporation;
   moving the lysate to the at least one reaction chamber by applying positive or negative pressure to the microfluidic channel;
   applying heat to the at least one reaction chamber;
   performing a reaction in the at least one reaction chamber; and
   monitoring the at least one reaction chamber to determine whether the target of interest is present in the biological sample.

2. The method of claim 1, wherein a magnetic field is created using a solenoid.

3. The method of claim 1, wherein the electric field is applied to a sample as it travels through a channel to the reaction chamber.

4. The method of claim 1, wherein the steps of adding a sample to a filter through obtaining a lysate comprises using a spin column filtration configuration or a syringe based cartridge.

5. The method of claim 1, wherein the method additionally includes prewetting the filter.

6. The method of claim 5, wherein prewetting comprises releasing a prewetting fluid.

7. The method of claim 5, wherein washing the sample comprises releasing a washing fluid.

8. The method of claim 5 wherein the sample is held in a first portion of the sample chamber until prewetting the filter occurs.

9. The method of claim 5 wherein a check valve is present in the sample chamber to separate the first portion of the chamber from a second portion.

10. The method of claim 9, wherein the second portion of the sample chamber contains the filter.

11. The method of claim 1, wherein the target of interest is selected from the group consisting of: *Trichomonas vaginalis, Chlamytha trachomatis*, and *Neisseria gonorrhoeae*.

12. The method of claim 1, wherein a sample processing control is additionally provided in the sample chamber with the biological sample.

13. The method of claim 1, wherein the biological sample is selected from the group consisting of: bronchoalveolar lavage, urine, blood, saliva, cerebrospinal fluid, endocervical, vaginal, buccal, nasal, tears, serum, plasma, biopsy sample, skin, stool, sweat, synovial fluid, wound fluid, dental scraping, and penile swab.

14. The method of claim 13, wherein the biological sample is a urine sample.

15. The method of claim 6, wherein the prewetting liquid is released by crushing a blister pack, or by using a plunger to burst a blister pack.

16. The method of claim 6, wherein the prewetting liquid is water.

17. The method of claim 1, wherein the biological sample is released for filtering by application of a negative pressure below a check valve crack pressure.

18. The method of claim 1, wherein the biological sample is filtered through the filter using a negative pressure from downstream of the filter.

19. The method of claim 1, wherein the biological sample is filtered through the filter using a positive pressure from upstream of the filter.

20. The method of claim 1, wherein a negative pressure is used to draw the washing liquid through the filter.

21. The method of claim 1, wherein the washing liquid is water.

22. The method of claim 1, wherein the lysis liquid is released onto the filter by crushing a blister pack or by using a plunger to burst a blister pack.

23. The method of claim 15 or 22 wherein the blister pack contains a frangible seal.

24. The method of claim 1, wherein at least one resistive heater are used to rapidly heat the filter and lyse the bacteria in the biological sample.

25. The method of claim 24, wherein the at least one resistive heater is attached to a heat block.

26. The method of claim 25, wherein the heat block is configured to have the same interior shape as the outer shape of the sample chamber.

27. The method of claim 1, wherein the lysate is drawn past a first Y-branch separating waste from reaction chambers.

28. The method of claim 27, wherein the lysate is drawn past a second Y-branch separating the lysate into at least one measured portions for at least one reaction.

29. The method of claim 1, wherein the lysate is dispensed into at least one reaction chamber.

30. The method of claim 29, wherein the reaction chamber contains dried reagents.

31. The method of claim 30 wherein the reaction chamber is heated to mix the dispensed lysate and the dried reagent.

32. The method of claim 29, wherein the at least one reaction chamber fills until a hydrophobic valve is sealed, corresponding to a desired reaction volume.

33. The method of claim 31, wherein heat is applied by a Peltier device.

34. The method of claim 1, wherein the reaction performed in the reaction chamber is an amplification reaction.

35. The method of claim 34, wherein the amplification reaction is PCR.

36. The method of claim 35, wherein monitoring the at least one reaction chamber comprises monitoring the reaction chamber for a detectable property.

37. The method of claim 36, wherein the detectable property is fluorescence.

38. The method of claim 37, wherein a fluorescence signal is monitored during a PCR reaction using two color channels.

39. The method of claim 38, wherein at least one color channel is used for a control signal.

40. The method of claim 38, wherein a quantification cycle is determined for each color and compared to cutoffs to return results for each assay.

41. The method of claim 12, wherein monitoring the reaction chamber for the sample processing control will confirm whether the sample has been captured and lysed.

42. The method of claim 41, wherein the sample processing control is selected from a dried micro-organism, a plasmid construct, or polynucleotide.

43. The method of claim 42, wherein the sample processing control is a human cell or DNA sequence.

44. A method for analyzing a biological sample for the presence of a target of interest, the method comprising:
  providing a cartridge, wherein the cartridge comprises a holding tank, a sample chamber, a waste chamber, and at least one reaction chamber, wherein fluidic communication between the holding tank, sample chamber, waste chamber and at least one reaction chamber is provided by one or more microfluidic channels and wherein the sample chamber comprises a filter;
  adding the biological sample to the holding tank,
  pre-wetting the filter by releasing a prewetting fluid onto the filter;
  adding the biological sample to pre-wetted filter;
  enriching the biological sample;
    wherein the step of enriching the sample comprises:
      (a) filtering the biological sample through the filter in the sample chamber, wherein fluid passed through the filter is stored in a waste chamber and the remainder of the biological sample remains in the sample chamber; or,
      (b) magnetically labeling the targets of interest within the sample and subjecting the labelled sample to a magnetic field;
  washing the sample by releasing a washing fluid into the sample chamber;
  drawing the washing fluid through the filter by applying positive or negative pressure, wherein the washing fluid passed through the filter is stored in the waste chamber;
  releasing a lysis fluid into the sample chamber;
  producing a lysate by (a) applying heat to the filter and the biological sample or by (b) subjecting the biological sample to an electric field to cause electroporation;
  moving the lysate to the at least one reaction chamber by applying positive or negative pressure to the microfluidic channel;
  applying heat to the at least one reaction chamber;
  performing a reaction in the at least one reaction chamber; and
  monitoring the at least one reaction chamber to determine whether the target of interest is present in the biological sample.

45. The method of claim 44, wherein the biological sample is retained in the holding tank until the step of pre-wetting the filter is complete.

* * * * *